(12) United States Patent
Karaborni et al.

(10) Patent No.: US 10,716,760 B2
(45) Date of Patent: Jul. 21, 2020

(54) ORAL DOSAGE FORMS OF METHYL HYDROGEN FUMARATE AND PRODRUGS THEREOF

(71) Applicant: XENOPORT, INC., Santa Clara, CA (US)

(72) Inventors: Sami Karaborni, Cupertino, CA (US); Sarina Grace Harris Ma, Santa Clara, CA (US); Chen Mao, Foster City, CA (US); Ching Wah Chong, Fremont, CA (US); Peter Robert Prinz Freed, Downingtown, PA (US); Mesut Ciper, Berlin (DE); Stefanie Krenzlin, Muenster (DE); David J. Wustrow, Los Gatos, CA (US); Peter A. Virsik, Portola Valley, CA (US)

(73) Assignee: Arbor Pharmaceuticals, LLC, Atlanta, GA (US)

( * ) Notice: Subject to any disclaimer, the term of this patent is extended or adjusted under 35 U.S.C. 154(b) by 0 days.

(21) Appl. No.: 14/990,582

(22) Filed: Jan. 7, 2016

(65) Prior Publication Data
US 2016/0113879 A1 Apr. 28, 2016
US 2017/0157056 A9 Jun. 8, 2017

Related U.S. Application Data

(62) Division of application No. 13/973,456, filed on Aug. 22, 2013, now Pat. No. 9,597,292.

(60) Provisional application No. 61/841,513, filed on Jul. 1, 2013, provisional application No. 61/837,796, filed on Jun. 21, 2013, provisional application No. 61/769,513, filed on Feb. 26, 2013, provisional application No. 61/733,234, filed on Dec. 4, 2012, provisional application No. 61/713,897, filed on Oct. 15, 2012, provisional application No. 61/713,961, filed on Oct. 15, 2012, provisional application No. 61/692,168, filed on Aug. 22, 2012, provisional application No. 61/692,174, filed on Aug. 22, 2012, provisional application No. 61/692,179, filed on Aug. 22, 2012.

(51) Int. Cl.
| | | |
|---|---|---|
| A61K 9/28 | (2006.01) | |
| A61K 9/16 | (2006.01) | |
| A61K 9/20 | (2006.01) | |
| A61K 31/225 | (2006.01) | |
| A61K 31/215 | (2006.01) | |
| A61K 31/27 | (2006.01) | |
| A61K 31/5375 | (2006.01) | |
| A61K 9/14 | (2006.01) | |
| A61K 9/48 | (2006.01) | |

(52) U.S. Cl.
CPC ........... *A61K 9/2886* (2013.01); *A61K 9/146* (2013.01); *A61K 9/1652* (2013.01); *A61K 9/2054* (2013.01); *A61K 9/2095* (2013.01); *A61K 9/284* (2013.01); *A61K 9/2826* (2013.01); *A61K 9/2866* (2013.01); *A61K 9/4808* (2013.01); *A61K 9/4866* (2013.01); *A61K 31/215* (2013.01); *A61K 31/225* (2013.01); *A61K 31/27* (2013.01); *A61K 31/5375* (2013.01); *Y02A 50/414* (2018.01)

(58) Field of Classification Search
None
See application file for complete search history.

(56) References Cited

U.S. PATENT DOCUMENTS

| | | |
|---|---|---|
| 3,139,395 A | 6/1964 | Griffin |
| 3,336,364 A | 8/1967 | Dill |
| 4,851,439 A | 7/1989 | Speiser et al. |
| 4,863,916 A | 9/1989 | Habich et al. |
| 4,959,389 A | 9/1990 | Speiser et al. |
| 5,073,641 A | 12/1991 | Bundgaard et al. |
| 5,145,684 A | 9/1992 | Liversidge et al. |
| 5,149,695 A | 9/1992 | Speiser et al. |
| 5,424,332 A | 6/1995 | Speiser et al. |
| 5,451,667 A | 9/1995 | Speiser et al. |
| 5,534,250 A | 7/1996 | Klaveness et al. |
| 6,130,248 A | 10/2000 | Nudelman et al. |
| 6,277,882 B1 | 8/2001 | Joshi et al. |
| 6,355,676 B1 | 3/2002 | Joshi et al. |
| 6,359,003 B1 | 3/2002 | Joshi et al. |
| 6,379,697 B1 | 4/2002 | Gregoriadis et al. |
| 6,436,992 B1 | 8/2002 | Joshi et al. |
| 6,509,376 B1 | 1/2003 | Joshi et al. |
| 6,613,800 B1 | 9/2003 | Smith |
| 6,709,868 B2 | 3/2004 | Law et al. |
| 6,723,508 B2 | 4/2004 | Sprenger et al. |

(Continued)

FOREIGN PATENT DOCUMENTS

| | | |
|---|---|---|
| CN | 1616400 | 5/2005 |
| CN | 101318901 | 12/2008 |

(Continued)

OTHER PUBLICATIONS

Rostami et al., "Pharmacokinetics of anti-psoriatic fumaric acid esters in psoriasis patients", 2010, Arch Dermatol Res, vol. 302, pp. 531-538.*

O'Donnell et al., "Remington The Science and Practice of Pharmacy" 21st Edition, 2005, Chapter 52, pp. 1025-1036.

Bhattacharya et al., Polymorphism in Pharmaceutical Solids: Thermoanalytical and Crystallographic Methods 334 (Brittain H. ed., 2d ed. Informa Healthcare USA, Inc. 2009) (1999), 20 pp.

Ivanisevic et al., "Uses of X-Ray Powder Diffraction in the Pharmaceutical Industry," Pharmaceutical Formulation & Quality, 32 (2011), pp. 30-33.

(Continued)

*Primary Examiner* — Robert A Wax
*Assistant Examiner* — Randeep Singh
(74) *Attorney, Agent, or Firm* — King & Spalding

(57) ABSTRACT

Improved oral dosage forms of methyl hydrogen fumarate and prodrugs thereof are disclosed. Methods of treating diseases such as multiple sclerosis and psoriasis using such dosage forms are also disclose.

18 Claims, 16 Drawing Sheets

(56) References Cited

U.S. PATENT DOCUMENTS

| | | | |
|---|---|---|---|
| 6,858,750 B2 | 2/2005 | Joshi et al. |
| 7,157,423 B2 | 1/2007 | Joshi et al. |
| 7,320,999 B2 | 1/2008 | Joshi et al. |
| 7,432,240 B2 | 10/2008 | Joshi et al. |
| 7,612,110 B2 | 11/2009 | Joshi et al. |
| 7,619,001 B2 | 11/2009 | Joshi et al. |
| 7,638,118 B2 | 12/2009 | Flachsmann et al. |
| 7,790,916 B2 | 9/2010 | Joshi et al. |
| 7,803,840 B2 | 9/2010 | Joshi et al. |
| 7,906,659 B2 | 3/2011 | Joshi et al. |
| 7,915,310 B2 | 3/2011 | Joshi et al. |
| 8,067,467 B2 | 11/2011 | Joshi et al. |
| 8,148,414 B2 | 4/2012 | Gangakhedkar et al. |
| 8,399,514 B2 | 3/2013 | Lukashev et al. |
| 8,524,773 B2 | 9/2013 | Joshi et al. |
| 8,669,281 B1 | 3/2014 | Zeidan et al. |
| 8,759,393 B2 | 6/2014 | Joshi et al. |
| 8,778,991 B2 | 7/2014 | Gangakhedkar et al. |
| 8,785,443 B2 | 7/2014 | Gangakhedkar et al. |
| 8,906,420 B2 | 12/2014 | Nilsson et al. |
| 8,952,006 B2 | 2/2015 | Cundy et al. |
| 2003/0018072 A1 | 1/2003 | Joshi et al. |
| 2004/0054001 A1 | 3/2004 | Joshi et al. |
| 2004/0102525 A1 | 5/2004 | Kozachuk |
| 2005/0095292 A1 | 5/2005 | Benjamin et al. |
| 2005/0096369 A1 | 5/2005 | Hoang |
| 2005/0101779 A1 | 5/2005 | Sagi et al. |
| 2005/0112193 A1* | 5/2005 | Phillips ............... A61K 9/5026 424/464 |
| 2005/0148664 A1 | 7/2005 | Joshi et al. |
| 2005/0208133 A1* | 9/2005 | Tsutsumi ............. A61K 9/209 424/472 |
| 2005/0281876 A1* | 12/2005 | Li ....................... A61K 9/2013 424/473 |
| 2006/0205659 A1 | 9/2006 | Joshi et al. |
| 2006/0269925 A1 | 11/2006 | Nunes et al. |
| 2007/0009475 A1 | 1/2007 | Flachsmann et al. |
| 2007/0027076 A1 | 2/2007 | Joshi et al. |
| 2007/0213300 A1 | 9/2007 | Liu et al. |
| 2007/0231382 A1 | 10/2007 | Karnachi et al. |
| 2007/0248663 A1 | 10/2007 | Joshi et al. |
| 2007/0253902 A1 | 11/2007 | Lobb et al. |
| 2008/0004344 A1 | 1/2008 | Nilsson et al. |
| 2008/0033199 A1 | 2/2008 | Lai et al. |
| 2008/0089861 A1 | 4/2008 | Went et al. |
| 2008/0089896 A1 | 4/2008 | Wang et al. |
| 2008/0227847 A1 | 9/2008 | Nilsson et al. |
| 2008/0233185 A1 | 9/2008 | Joshi et al. |
| 2008/0299196 A1 | 12/2008 | Nilsson et al. |
| 2008/0300217 A1 | 12/2008 | Nilsson |
| 2009/0011620 A1 | 1/2009 | Joshi et al. |
| 2009/0181085 A1 | 7/2009 | Joshi et al. |
| 2009/0182047 A1 | 7/2009 | Joshi et al. |
| 2009/0304790 A1 | 12/2009 | Nilsson et al. |
| 2010/0048651 A1 | 2/2010 | Gangakhedkar et al. |
| 2010/0099907 A1 | 4/2010 | Raillard et al. |
| 2010/0105784 A1 | 4/2010 | Remon et al. |
| 2010/0130607 A1 | 5/2010 | Gold |
| 2010/0144651 A1 | 6/2010 | Nilsson et al. |
| 2010/0226981 A1 | 9/2010 | Karaborni et al. |
| 2010/0247642 A1 | 9/2010 | Wu et al. |
| 2010/0260755 A1 | 10/2010 | Gammans et al. |
| 2011/0112196 A1 | 5/2011 | Lukashev |
| 2011/0124615 A1 | 5/2011 | Joshi et al. |
| 2011/0212169 A1 | 9/2011 | Bae et al. |
| 2011/0293711 A1 | 12/2011 | Joshi et al. |
| 2012/0034274 A1 | 2/2012 | Nilsson et al. |
| 2012/0034303 A1 | 2/2012 | Nilsson et al. |
| 2012/0095003 A1 | 4/2012 | Gangakhedkar et al. |
| 2012/0157523 A1 | 6/2012 | Gangakhedkar et al. |
| 2012/0165404 A1 | 6/2012 | Lukashev |
| 2013/0065909 A1 | 3/2013 | Milne et al. |
| 2013/0172391 A1 | 7/2013 | Kahrs |
| 2013/0203753 A1 | 8/2013 | Cundy et al. |
| 2013/0259856 A1 | 10/2013 | Kaye |
| 2013/0259906 A1 | 10/2013 | Joshi et al. |
| 2013/0295169 A1 | 11/2013 | Goldman et al. |
| 2013/0302410 A1 | 11/2013 | Gold |
| 2013/0317103 A1 | 11/2013 | Lukashev |
| 2013/0324539 A1 | 12/2013 | Virsik et al. |
| 2014/0051705 A1 | 2/2014 | Cundy et al. |
| 2014/0056973 A1 | 2/2014 | Ma et al. |
| 2014/0056978 A1 | 2/2014 | Karaborni et al. |
| 2014/0057917 A1 | 2/2014 | Cundy et al. |
| 2014/0057918 A1 | 2/2014 | Wustrow et al. |
| 2014/0065211 A1 | 3/2014 | Karaborni et al. |
| 2014/0066505 A1 | 3/2014 | Joshi et al. |
| 2014/0099364 A2 | 4/2014 | Nilsson et al. |
| 2014/0163100 A1 | 6/2014 | Dawson et al. |
| 2014/0179778 A1 | 6/2014 | Mao et al. |
| 2014/0179779 A1 | 6/2014 | Chao |
| 2014/0193386 A1 | 7/2014 | Preiss-Bloom et al. |
| 2014/0193387 A1 | 7/2014 | Gruskin et al. |
| 2014/0193388 A1 | 7/2014 | Velders et al. |
| 2014/0193390 A1 | 7/2014 | Valenzano et al. |
| 2014/0193392 A1 | 7/2014 | Annunziata et al. |
| 2014/0193393 A1 | 7/2014 | Gulati |
| 2014/0193495 A1 | 7/2014 | Nilsson |
| 2014/0194427 A1 | 7/2014 | Chao |
| 2014/0200272 A1 | 7/2014 | Nilsson et al. |
| 2014/0200273 A1 | 7/2014 | Nilsson et al. |
| 2014/0200363 A1 | 7/2014 | Guzowski et al. |
| 2014/0205659 A1 | 7/2014 | Nilsson et al. |
| 2014/0275048 A1 | 9/2014 | Zeidan et al. |
| 2014/0275250 A1 | 9/2014 | Cundy et al. |
| 2014/0284245 A1 | 9/2014 | Karaborni et al. |
| 2014/0323570 A1 | 10/2014 | Gold |
| 2014/0329818 A1 | 11/2014 | Gangakhedkar et al. |
| 2014/0336151 A1 | 11/2014 | Chao |
| 2014/0364604 A1 | 12/2014 | Raillard et al. |
| 2014/0378542 A1 | 12/2014 | Mao et al. |
| 2015/0038499 A1 | 2/2015 | Virsik |
| 2015/0073049 A1 | 3/2015 | Mao et al. |
| 2015/0079180 A1 | 3/2015 | Karaborni et al. |
| 2015/0190360 A1 | 7/2015 | Cundy |
| 2015/0265707 A1 | 9/2015 | Manthati et al. |

FOREIGN PATENT DOCUMENTS

| | | |
|---|---|---|
| CN | 101774913 A | 7/2010 |
| DE | 1165586 | 3/1964 |
| DE | 10360869 A1 | 4/2005 |
| EP | 2692344 A1 | 2/2014 |
| GB | 1153927 A | 6/1969 |
| GB | 1404989 A | 9/1975 |
| GB | 2285805 A | 7/1995 |
| JP | S60181047 | 9/1985 |
| JP | H03294245 | 12/1991 |
| JP | 2001158760 | 6/2001 |
| JP | 2002-027998 A | 1/2002 |
| PL | 153592 | 10/1991 |
| WO | WO 1996/036613 | 11/1996 |
| WO | WO 1998/029114 | 7/1998 |
| WO | WO 1998/052549 | 11/1998 |
| WO | WO 1998/053803 | 12/1998 |
| WO | WO99/21559 | 5/1999 |
| WO | WO 1999/049858 | 10/1999 |
| WO | WO 1999/051191 A1 | 10/1999 |
| WO | WO 1999/062973 A1 | 12/1999 |
| WO | WO 2000/010560 A1 | 3/2000 |
| WO | WO 2000/012072 A2 | 3/2000 |
| WO | WO 2002/055063 | 7/2002 |
| WO | WO 2002/055066 | 7/2002 |
| WO | WO 2002/055067 | 7/2002 |
| WO | WO 2003/087174 | 10/2003 |
| WO | WO 2005/023241 | 3/2005 |
| WO | WO 2005/027899 | 3/2005 |
| WO | WO 2006/037342 | 4/2006 |
| WO | WO 2006/050730 | 5/2006 |
| WO | WO 2006/122652 | 11/2006 |
| WO | WO 2007/006307 | 1/2007 |
| WO | WO 2007/006308 | 1/2007 |
| WO | WO 2007/042034 | 4/2007 |
| WO | WO 2007/042035 | 4/2007 |

(56) References Cited

FOREIGN PATENT DOCUMENTS

| WO | WO 2008/096271 | 8/2008 |
|---|---|---|
| WO | WO 2008/097596 | 8/2008 |
| WO | WO 2010/022177 | 2/2010 |
| WO | WO 2010/079221 | 7/2010 |
| WO | WO 2010/079222 | 7/2010 |
| WO | WO 2010/126605 | 11/2010 |
| WO | WO 2011/080344 | 7/2011 |
| WO | WO 2011/100589 | 8/2011 |
| WO | WO 2012/162669 | 11/2012 |
| WO | WO 2012/170923 | 12/2012 |
| WO | WO 2013/022882 | 2/2013 |
| WO | WO 2013/076216 | 5/2013 |
| WO | WO 2013/119677 | 8/2013 |
| WO | WO 2013/119791 | 8/2013 |
| WO | WO 2014/020156 | 2/2014 |
| WO | WO 2014/031894 | 2/2014 |
| WO | WO 2014/031897 | 2/2014 |
| WO | WO 2014/071371 | 5/2014 |
| WO | WO 2014/096425 | 6/2014 |
| WO | WO 2014/100728 | 6/2014 |
| WO | WO 2014/190056 | 11/2014 |
| WO | WO 2015/028472 | 3/2015 |
| WO | WO 2015/028473 | 3/2015 |

OTHER PUBLICATIONS

Gogas et al., "Comparison of the efficacy and tolerability of a novel methyl hydrogen fumarate prodrug with dimethyl fumarate in rodent EAE and GI irritation models," Multiple Sclerosis, 2010, vol. 16, No. 10 Supplement, pp. S230-S231.
Dow, "Methocel Cellulose Technical Handbook", <http://www.dow.com/dowwolff/en/pdf/192-01062.pdf>, 2002, 32 pages.
Carter et al., Chemotherapy of Cancer, 2nd ed., 1981, pp. 362-365.
Altmeyer et al., Antipsoriatic effect of fumaric acid derivatives, J. Amer. Acad. Derm. (1994), 30(6): 977-981.
Altschul et al., "Gapped BLAST and PSI-BLAST: a new generation of protein database search programs," Nucleic Acids Research, 1997, vol. 25, No. 17, pp. 3389-3402.
ASHE, Learning and memory in transgenic mice modeling Alzheimer's disease. Learning & Memory (2001), 8, 301-308.
Associated Press; FDA mulls drug to slow late-stage Alzheimer's [online]; [retrieved on Sep. 24, 2003]; retrieved from the internet, <http://www.cnn.com/2003/HEALTH/conditions/09/24/alzheimers.drug.ap/index.html>; Sep. 24, 2003; 2 pages.
Atreya et al., "NF-κB in inflammatory bowel disease," Journal of Internal Medicine (2008), 263(6), pp. 591-596.
Author Unknown, BG 00012, BG 12/oral fumarate, FAG-201, second-generation fumarate derivative—Fumapharm/Biogen Idec, Drugs RD (2005), 6(4): 229-230.
Bar-Or et al., "Clinical efficacy of BG-12 (dimethyl fumarate) in patients with relapsing-remitting multiple sclerosis: subgroup analyses of the DEFINE study," J. Neurol, 2013, vol. 260, pp. 2297-2305.
Bardgett et al., NMDA receptor blockade and hippocampal neuronal loss impair fear conditioning and position habit reversal in C57B1/6 mice. Brain Res Bull (2003), 60, 131-142.
Barnes, "Mediators of chronic obstructive pulmonary disease," Pharmacological Reviews (2004), 56(4), pp. 515-548.
Behari et al., Baseline characteristics of a subpopulation of Indian patients enrolled in two phase 3 trials for oral BG-12 in relapsing-remitting multiple sclerosis, 62nd Ann Mtg. Amer. Acad. Neurol. (2010), poster, 2 pages.
Benoit et al., Etude Clinique de L'ester B-Morpholinoethylique de L'Acide Niflumique en Stomatologie Infantile, Rev. Odontostomatol Midi Fr. (1975), 4: 249-261.
Bertone, "Prevalence of Gastric Ulcers in Elite, Heavy Use Western Performance Horses," AAEP Proceedings (2000). 46: 256-259.
Bhagavathula et al., 7-Chloro-5-(4-hydroxyphenyl)-1-methyl-3-(naphthalen-2-ylmethyl)-4,5-dihydro-1H-benzo[b][1,4]diazepin-2(3H)-one (Bz-423), a benzodiazepine, suppresses keratinocyte proliferation and has antipsoriatic activity in the human skin-severe, combined immunodeficient mouse transplant model. J Pharmacol Expt'l Therapeutics (2008), 324(3), 938-947.
Blad, et al., "Biological and Pharmacological Roles of HCA Receptors", Advances in Pharmacology, 2011, 62: 219-250.
Blandini, et al., "Glutamate and Parkinson's disease," Molecular Neurobiology (1996), 12(1), pp. 73-94.
Boehncke, "Animal Models of T Cell-Mediated Skin Diseases, Chapter 12: The Psoriasis SCID Mouse Model: A Tool for Drug Discovery?" Ernst Schering Res Found Workshop 50, Zollner et al., eds. New York: Springer (2005) pp. 213-234.
Brewer, et al., "Fumaric acid esters in the management of severe psoriasis", Clinical Experimental Dermatology, 2007, 32: 246-249.
Brown et al., "Goodman & Gilman's The Pharmacological Basis of Therapeutics, Tenth Edition: Chapter 7, Muscarinic Receptor Agonists and Antagonists," A. Gilman, J. Hardman and L. Limbird, eds., Mc-Graw Hill Press, 2001, pp. 155-173.
Bruhn et al., "Concordance between enzyme activity and genotype of glutathione S-transferase theta (GSTT1)," Biochemical Pharmacology, 1998, vol. 56, pp. 1189-1193.
Bundgaard et al., Esters of N,N-Disubstituted 2-Hydroxyacetamides as a Novel Highly Biolabile Prodrug Type for Carboxylic Acid Agents, J. Med. Chem. (1987), 30(3): 451-454.
Bundgaard et al., Glycolamide esters as a novel biolabile prodrug type for non-steroidal anti-inflammatory carboxylic acid drugs, Int. J. Pharm. (1988) 43: 101-110.
Büyükcoskun, Central Effects of Glucagon-like Peptide-1 on Cold Restraint Stress-induced Gastric Mucosal Lesions, Turk J. Gastroenterol (2007), 18(3): 150-156.
Büyükcoskun, Role of Intracerebroventricular Vasopressin in the Development of Stress-Induced Gastric Lesions in Rats, Physiol. Res. (1999), 48: 451-455.
Caira, "Crystalline Polymorphism of Organic Compounds," Topics in Current Chemistry, Springer, Berlin, DE (1998), vol. 198, pp. 163-208.
Camandola et al., "NF-kB as a therapeutic target in neurodegenerative diseases," Expert Opinion Therapeutic Targets (2007), 11(2), pp. 123-132.
Capello, et al., "Marburg type and Balo's concentric sclerosis: Rare and acute variants of multiple sclerosis", Neurological Sciences 200411 IT, vol. 25, No. Suppl. 4, Nov. 2004, pp. S361-S363.
Cavarra et al., Effects of cigarette smoke in mice with different levels of α1-proteinase inhibitor and sensitivity to oxidants. Am J Respir Crit Care Med (2001), 164, 886-890.
Champion, et al., "Flushing and Flushing Syndromes, Rosacea and Perioral Dermatitis", Rook Wilkinson Ebling Textbook of Dermatology, 6th ed. vol. 3, Oxford, UK: Blackwell Scientific, 1998, pp. 2099-2104.
Chaudhary et al., "Enhancement of solubilization and bioavailability of poorly soluble drugs by physical and chemical modifications: A recent review," Journal of Advanced Pharmacy Education & Research (2012), 2(1), pp. 32-67.
Chen et al., "Nanonization strategies for poorly water-soluble drugs," Drug Discovery Today, 2010, pp. 1-7.
Cockcroft et al., Bronchial reactivity to inhaled histamine: a method and clinical survey. Clin Allergy (1977), 7, 235-243.
Cross, et al. Dimethyl Fumarate, an Immune Modulator and Inducer of the Antioxidant Response, Suppresses HIV Replication and Macrophage-Mediated Neurotoxicity: A Novel Candidate for HIV Neuroprotection. The Journal of Immunology, (2011), 187(10): 5015-5025.
D'Acquisto et al., Inhibition of nuclear factor kappa B (NF-κB): an emerging theme in anti-inflammatory therapies. Molecular Interventions (2002), 2(1), 22-35.
Damasio; "Alzheimer's Disease and Related Dementias;" Cecil Textbook of Medicine; 1996; 20th Edition, vol. 2; pp. 1992-1996.
Dawson et al., "Bioequivalence of BG-12 (Dimethyl Fumarate) Administered as a Single 240 mg Capsule and Two 120 mg Capsules: Findings from a Randomized, Two-period Crossover Study", Poster P913 presented at the 28th Congress of the European Committee for Treatment and Research in Multiple Sclerosis, Oct. 10-13, 2012, Lyon France, 1 page.

(56) References Cited

OTHER PUBLICATIONS

De Jong et al., Selective stimulation of T helper 2 cytokine responses by the anti-psoriasis agent monomethylfunarate, Eur. J. Immunol. (1996), 26: 2067-2074.

Dibbert, et al.,: "Detection of fumarate-glutathione adducts in the portal vein blood of rats: Evidence for rapid dimethyl fumarate metabolism", Archives of Dermatological Research 2013 Springer Verlag Deu, vol. 305, No. 5, Jul. 2013 (Jul. 2013), pp. 447-451.

Dymicky, Preparation of Monomethyl Fumarate, Organic Preparations and Procedures International, vol. 15 No. 4 (1983), pp. 233-238.

Eberle, et al. Fumaric Acid Esters in Severe Ulcerative Necrobiosis Lipoidica: A Case Report and Evaluation of Current Therapies. Acta Dermato-Venereologica (2010) 90(1): 104-106.

Ellrichmann et al., Efficacy of fumaric acid esters in the R6/2 and YAC128 models of Huntington's disease, PLOS One (2011), 6(1): 11 pages.

Etter et al., "The Use of Cocrystallization as a Method of studying Hydrogen Bond Preferences of 2-Aminopyrimidine," Journal of the Chemical Society (1990), No. 8, pp. 589-591.

Etter et al., "Graph Set Analysis of Hydrobgen-Bond Patterns in Organic Crystals," Acta Crystallogr., Sect. B, Struct. Sci. (1990), B46, pp. 256-262.

Etter et al., "Hydrogen Bond Directed Cocrystallization and Molecular Recognition Properties of Diarylureas," Journal of the Chemical Society (1990), No. 112, pp. 8415-8426.

Eugster et al., Superantigen overcomes resistance of IL-6 deficient mice towards MOG-induced EAE by a TNFR1 controlled pathway. Eur J Immunol (2001), 31, 2302-2312.

European Commission Health & Consumer Protection Directorate-General, Report of the scientific committee on animal nutrition on the safety of fumaric acid, adopted Jan. 22, 2003: 18 pages.

Feinstein et al., Anti-inflammatory and prometabolic effects of BG-12 in glial cells, 26th Congress Eur. Cmtee. Treat. Res. Mult. Scler. (2010), poster: 1 page.

Fits et al., Imiquimod-Induced Psoriasis-Like Skin Inflammation in Mice Is Mediated via the IL-23/IL-17 Axis, J. Immunol. (2009), 182: 5836-5845.

Food and Drug Administration—Department of Health and Human Services; "International Conference on Harmonisation; Guidelines for the Photostability Testing of New Drug Substances and Products; Availability; Notice," Federal Register, vol. 62, No. 95; May 16, 1997, pp. 27115-27122.

Fox et al., Baseline characteristics of patients in a randomized, multicenter, placebo-controlled and active comparator trial evaluating efficacy and safety of BG-12 in relapsing-remitting multiple sclerosis: the CONFIRM trial, 62nd Ann Mtg. Amer. Acad. Neurol. (2010), poster, 2 pages.

Fox et al., Placebo-controlled phase 3 study of oral BG-12 or glatiramer in multiple sclerosis, N Engl J Med. Sep. 20, 2012;367(12):1087-97. Erratum in: N Engl J Med. Oct. 25, 2012;367(17):1673.

Frycak et al., Evidence of covalent interaction of fumaric acid esters with sulfhydryl groups in peptides, J. Mass. Spectrom. (2005), 40: 1309-1318.

Gadad et al., Synthesis, spectral studies and anti-inflammatory activity of glycolamide esters of niflumic acid as potential prodrugs, Arzneim Forsch Drug Res. (2002), 52(11): 817-821.

Gambichler, et al. Clearance of Necrobiosis lipoidica with Fumaric Acid Esters. Dermatology (2003), 207(4): 422-424.

Gesser et al., Dimethylfumarate specifically inhibits the mitogen and stress-activated kinases 1 and 2 (MSK1/2): Possible role for its anti-psoriatic effect. J Investigative Dermatology (2007), 127, 2129-2137.

Goke et al., Effect of a Specific Serine Protease Inhibitor on the Rat Pancreas: Systemic Administration of Camostate and Exocrine Pancreatic Secretion, Digestion (1984) 30: 171-178.

Gogas et al., Comparison of the efficacy and tolerability of a novel methyl hydrogen fumarate prodrug with dimethyl fumarate in rodent EAE and GI irritation models, XenoPort, Inc.; 26th Congress of the European Committee for Treatment and Research in Multiple Sclerosis (ECTRIMS), 2010 (Poster #671), 1 page.

Gold et al., Baseline characteristics of patients in the DEFINE trial: a randomized, multicenter, double blind, placebo-controlled, phase 3 study of BG-12 in relapsing-remitting multiple sclerosis, 62nd Ann Mtg. Amer. Acad. Neurol. (2010), poster, 2 pages.

Gold et al., Placebo-controlled phase 3 study of oral BG-12 for relapsing multiple sclerosis, N Engl J Med. Sep. 20, 2012;367(12):1098-107, Erratum in: N Engl J Med. Dec. 13, 2012;367(24):2362.

Gorbitz et al., "On the inclusion of solvent molecules in the crystal structures of organic compounds," Acta Cryst. (2000), B56, pp. 526-534.

Ghoreschi Kamran, et al., "Furmarates improve psoriasis and multiple sclerosis by inducing type II dendritic cells", The Journal of Experimental Medicine, Rockefeller University Press, US, vol. 208, No. 11, Oct. 24, 2011 (Oct. 24, 2011), pp. 2291-2303.

Griffin, et al., The Chemistry of Photodimers of Maleic and Fumaric Acid Derivatives. I. Dimethyl Fumarate Dimer; J. Am. Chem. Soc. (1961), 83: pp. 2725-2728.

Grigorian et al., Control of T-cell mediated autoimmunity by metabolite flux to N-glycan biosynthesis, J. Bio. Chem. (2007), 282(27): 20027-20035.

Guenther, et al., Macular Exanthema Due to Fumaric Acid Esters. Annals of Pharmacotherapy (2003), 37(2): 234-236.

Gurney et al., Motor neuron degeneration in mice that express a human Cu,Zn superoxide dismutase mutation. Science (1994), 264, 1772-1775.

Hanson et al., Nicotinic acid- and monomethyl funarate-induced flushing involves GPR109A expressed by keratinocytes and COX-2-dependent prostanoid formation in mice, J. Clin. Invest. (2010), 120(8): 2910-2919.

Heiligenhaus, et al. Influence of dimethylfumarate on experimental HSV-1 necrotizing keratitis. Graefe's Archive for Clinical and Experimental Ophthalmology (2004), 242(10): 870-877.

Heiligenhaus, et al. Improvement of herpetic stromal keratitis with fumaric acid derivate is associated with systemic induction of T helper 2 cytokines. Clinical and Experimental Immunology (2011), 142(1): 180-187.

Hiraku et al., Absorption and Excretion of Camostat Orally Administered to Male Rabbit and Healthy Subject, Iyakuhin Kenkyu (1982) 13(3): 756-765.

Hoefnagel, et al., "Long-term safety aspects of systemic therapy with fumaric acid esters in severe psoriasis", British Journal of Dermatology, 2003, 149: 363-369.

Horig et al., From bench to clinic and back: Perspective on the 1st IQPC Translational Research Conference, J. Transl. Med. (2004), 2(44), 8 pages.

Hoxtermann et al., Fumaric acid esters suppress peripheral CD4- and CD8-positive lymphocytes in psoriasis, Dermatology (1998), 196: 223-230.

Hurd et al., Vinylation and the Formation of Acylals:, J. Am. Chem. Soc.; vol. 78; Jan. 5, 1956; pp. 104-106.

Iyer et al., Synthesis of iodoalkylacylates and their use in the preparation of S-alkyl phosphorothiolates. Synth Commun (1995), 25(18), 2739-2749.

Jamil, et al., "Studies of Photostability of Reserpine in Parenteral Solutions," Die Pharmazie (1983), 38: pp. 467-469.

Jennings, Squamous cell carcinoma as a complication of fumaric acid ester immunosuppression, J. Eur. Acad. Dermatol. Venereol. (2009), DOI: 10.1111/j.1468-3083.2009.03234.x, 1 page.

Jurjus et al., Animal models of inflammatory bowel disease. J Pharmacol Toxicol Methods (2004), 50, 81-92.

Kappos et al., Efficacy and safety of oral fumarate in patients relapsing-remitting multiple sclerosis: a multicentre, randomised, double-blind, placebo controlled phase IIb study, Lancet (2008), 372: 1463-1472.

Kamimura et al., "Stereoselective formation of optically active 2-oxy-1,3-oxazolidin-4-ones from chiral O-acylmandelamides or lactamides", Tetrahedron 58, 2002, 8763-8770.

Khan et al., Synthesis and biological evaluation of glycolamide esters as potential prodrugs of some non-steroidal anti-inflammatory drugs, Ind. J. Chem. (2002) 41B: 2172-2175.

(56) References Cited

OTHER PUBLICATIONS

Killestein, et al., "Oral treatment for multiple sclerosis," Lancet Neurology, Lancet Publishing Group, London, GB, vol. 10, No. 11, Nov. 2011, pp. 1026-1034.

Klein, et al. Off-label use of fumarate therapy for granulomatous and inflammatory skin diseases other than psoriasis vulgaris: a retrospective study. (2012), Journal of the European Academy of Dermatology and venereology (2012), 26(11): 1400-1406 (also on-line ref: Klein, et al., (2011), J Eur Acad Dermatol Venereol doi: 10.1111/j.1468-3083.2011.04303.x).

Kreuter et al., Fumaric acid esters in necrobiosis lipoidica: results of a prospective noncontrolled study. British Journal of Dermatology (2005) 153(4): 802-807.

Kumar et al., "Molecular Complexes of Some Mono- and Dicarboxylic Acids with trans-1,4-Dithiane-1,4-dioxide," American Chemical Society, Crystal Growth & Design (2002), 2(4), pp. 313-318.

Layzer; "Section Five—Degenerative Diseases of the Nervous System"; Cecil Textbook of Medicine; 1996; 20th Edition, vol. 2; pp. 2050-2057.

Lee et al., Spotlight on fumarates, Int. MS J. (2008), 15: 12-18.

Lehmann et al., Fumaric acid esters are potent immunosuppressants: inhibition of acute and chronic rejection in rat kidney transplantation models by methyl hydrogen fumarate. Arch Dermatol Res (2002), 294, 399-404.

Lehmann et al., Dimethylfumarate induces immunosuppression via glutathione depletion and subsequent induction of heme oxygenase 1. J Investigative Dermatology (2007), 127, 835-845.

Lei et al., "Novel Technology of Dimethyl Fumarate Synthesis," Ziyuan Kaifa Yu Shichang (2011), 27(9), pp. 787-789.

Linker et al., Identification and development of new therapeutics for multiple sclerosis, Treds. Pharm. Sci. (2008), DOI 10.1016/j.tips.2008.07.012, 8 pages.

Linker et al., Fumaric acid esters exert neuroprotective effects in neuroinflammation via activation of the Nrf2 antioxidant pathway, Brain (2011), 134: 678-692.

Litjens e al., Monomethylfumarate affects polarization of monocyte-derived dendritic cells resulting in down-regulated Th1 lymphocyte responses, Eur. J. Immunol. (2004), 34: 565-575.

Litjens et al., Pharmacokinetics of oral fumarates in healthy subjects, Br. J. Clin. Pharmacol. (2004), 58(4): 429-432.

Litjens et al., Effects of monomethylfumarate on dendritic cell differentiation, Br. J. Dermatol. (2006), 154: 211-217.

Loewe et al., "Dimethylfumarate inhibits TNF-induced nuclear entry of NF-κB/p65 in human endothelial cells," The Journal of Immunology (2002), 168, pp. 4781-4787.

Loewe et al., Dimethylfumarate impairs melanoma growth in metastasis, Cancer Res. (2006), 66(24): 11888-11896.

Lopez-Diego et al., Novel therapeutic strategies for multiple sclerosis—a multifaceted adversary, Nat. Review. Drug Disc. (2008), 7:909-925.

Los et al., Nuevos Estered De Acidos Anilinonicotinicos Y N-Fenilantranilicos Sustituidos, II Farmaco—Ed. Sc. (1980), 36(5): 372-85.

Lukashev et al., Activation of Nrf2 and modulation of disease by BG00012 (dimethyl fumarate) suggest a dual cytoprotective and anti-inflammatory mechanism of action, 62nd Ann Mtg. Amer. Acad. Neurol. (2010), poster, 4 pages.

Mandhane, et al., Adenosine A2 receptors modulate haloperidol-induced catalepsy in rats. Eur. J. Pharmacol (1997), 328, 135-141.

Martin, "Molecular basis of the neurodegenerative disorders," The New England Journal of Medicine (1999), 340(25), pp. 1970-1980.

Martorana et al., Roflumilast fully prevents emphysema in mice chronically exposed to cigarette smoke. Am J Respir Crit Care Med (2005), 172, 848-853.

Meissner et al., "Dimethyl fumarate—only an anti-psoriatic medication?", Journal Der Deutschen Demrmatologischen Gesellschaft (2012), vol. 10, pp. 793-801.

Menter et al., Guidelines of care for the management of psoriasis and psoriatic arthritis, J. Am. Acad. Dermatol. (2009), doi:10.1016/j.jaad.2009.03.027, 35 pages.

Merisko-Liversidge et al., "Nanosizing: a formulation approach for poorly-water-soluble compounds," European Journal of Pharmaceutical Sciences, 18 (2003), pp. 113-120.

Miller et al., Experimental Autoimmune Encephalomyelitis in the Mouse, Current Protocols in Immunology (2007), Supp. 78: 15.1.1-15.1.18.

Milo, et al., "Combination therapy in multiple sclerosis", Journal of Neuroimmunology, vol. 231, No. 1, 2011, pp. 23-31.

Mosmann et al., TH1 and TH2 cells: different patterns of lymphokine secretion lead to different functional properties, Ann. Rev. Immunol. (1989), 7: 145-73.

Mrowietz, et al., "Dimethylfumarate for psoriasis: more than a dietary curiosity," Trends in Molecular Medicine (2005), 11(1), pp. 43-48.

Mrowietz, et al., "Treatment of Psoriasis with Fumaric Acid Esters: Results of a prospective Multicenter Study," British Journal of Dermatology (1998), 138: 456-460.

Mrowietz et al., "Treatment of severe psoriasis with fumaric acid esters: scientific background and guidelines for therapeutic use," British Journal of Dermatology (1999), 141, pp. 424-429.

Mrowietz et al., Treatment of psoriasis with fumaric acid esters (Fumaderm®), JDDG (2007), DOI: 10.1111/j.1610-0387.2007.06346.x, 2 pages.

Muller et al., "High-performance liquid chromatography/fluorescence detection of S-methylglutathione formed by glutathione-S-transferase T1 in vitro," Arch Toxicol, 2001, vol. 74, pp. 760-767.

Murakami et al., Suppression of a dextran sodium sulfate-induced colitis in mice by zerumbone, a subtropical ginger sesquiterpene, and nimesulide: separately and in combination. Biochemical Pharmacol (2003), 66, 1253-1261.

Naldi et al., Psoriasis (chronic plaque), Clin. Evid. (2009), 1(1706): 50 pages.

Nelson, et al., Effect of Dietary Inducer Dimethylfumarate on Glutathione in Cultured Human Retinal Pigment Epithelial Cells. Investigative Ophthalmology and Visual Science (1999), 40(9): 1927-1935.

Neymotin et al., Neuroprotective effect of Nrf2/AFE activators, CDDO ethylamide and CDDO trifluoroethylamide, in a mouse model of amyotrophic lateral sclerosis, Free Rad. Bio. Med (2011), 51: 88-96.

Nibbering et al., Intracellular signalling by binding sites for the antipsoriatic agent monomethylfumarate on human granulocytes, Br. J. Dermatol. (1997), 137: 65-75.

Nielsen, et al., "Glycolamide Esters as Biolabile Prodrugs of Carboxylic Acid Agents: Synthesis, Stability, Bioconversion, and Physicochemical Properties", Journal of Pharmaceutical Sciences, vol. 77, No. 4, Apr. 1988, pp. 285-298.

Offermans, The nicotinic acid receptor GPR109A (HM74A or PUMA-G) as a new therapeutic agent, Trends Pharm. Sci. (2006), 27(7): 384-390.

O'Toole, et al., Treatment of Carcinoid Syndrome: A Prospective Crossover Evaluation of Lanreotide versus Octreotide in Terms of Efficacy, Patient Acceptability, and Tolerance, American Cancer Society, Feb. 15, 2000, 88(4), 770-776.

Panagiotou et al., "Form Nanoparticles via Controlled Crystallization," Chemical Engineering Progress; Oct. 2008, 104, 10, pp. 33-39.

Pathak et al., "Supercritical fluid technology for enhanced drug delivery," Expert Opin. Drug Deliv. (2005) 2(4):747-761.

Peeters et al., Fumaric acid therapy for psoriatic arthritis. A randomized, double-blind, placebo-controlled study, Br. J. Rheumatol. (1992), 31(7): 502-504.

Pemble et al., "Human glutathione S-transferase Theta (GSTT1): cDNA cloning and the characterization of a genetic polymorphism," Biochem. J., 1994, vol. 300, pp. 271-276.

Rantanen, The cause of the Chinese sofa/chair dermatitis epidemic is likely to be contact allergy to dimethylfumarate, a novel potent contact sensitizer, Br. J. Dermatol. (2008), 159: 218-221.

Reddingius, Bioanalysis and pharmacokinetics of fumarates in humans, Ph.D. dissertation ETH No. 12199, Swiss Fed. Inst. Tech. Zurich (1997), 82 pages.

(56) References Cited

OTHER PUBLICATIONS

Reich et al., Efficacy and safety of fumaric acid esters in the long-term treatment of psoriasis—a retrospective study (Future), JDDG (2009), DOI: 10.1111/j.1610-0387.2009.07120.x, 8 pages.
Richman et al., Nicotinic acid receptor agonists differentially activate downstream effectors, J. Bio. Chem. (2007), 282(25): 18028-18036.
Roll et al., Use of fumaric acid esters in psoriasis, Indian J. Dermatol. Ven. Lep. (2007), 73: 133-137.
Rostami-Yazdi, et al., "Detection of Metabolites of Fumaric Acid Esters in Human Urine: Implications for their mode of action", Journal of Investigative Dermatology, 2008, pp. 1-3.
Rostami-Yazdi et al., Pharmacokinetics of antipsoriatic fumaric acid esters in psoriasis patients, Arch. Dermatol. Res. (2010), 302: 531-538.
Rowland et al., "Amyotrophic lateral sclerosis," The New England Journal of Medicine (2001), 344(22), pp. 1688-1700.
Rubant et al., Dimethylfumarate reduces leukocyte rolling in vivo through modulation of adhesion molecule expression, J. Invest. Dermatol. (2007), 128: 326-331.
Sawant et al., "Necessity of Establishing Chemical Integrity of Polymorphs of Drug Substance Using a Combination of NMR, HPLC, Elemental Analysis, and Solid-State Characterization Techniques: Case Studies," Organic Process Research & Development (2013), vol. 17, No. 3, pp. 519-532.
Schafer et al., "Failure is an option: learning from unsuccessful proof-of-concept trials", Drug Discovery Today, vol. 13, Nos. 21/22; Nov. 2008; pp. 913-916.
Schilling, et al., "Fumaric acid esters are effective in chronic experimental autoimmune encephalomyelitis and suppress macrophage infiltration", Clinical and Experimental Immunology, 2006, 145: pp. 101-107.
Schimrigk, et al., "Oral fumaric acid esters for the treatment of active multiple sclerosis: an open-label, baseline-controlled pilot study," European Journal of Neurology (2006), vol. 13, pp. 604-610.
Schmidt, et al., "Reactivity of dimethyl fumarate and methylhydrogen fumarate towards glutathione and N-acetyl-1-cysteine-Preparation of S-substituted thiosuccinic acid esters", Bioorganic & Medicinal Chemistry, Pergamon, GB, vol. 15, No. 1 Nov. 15, 2006 (Nov. 15, 2006), pp. 333-342.
Seder et al., Acquisition of lymphokine-producing phenotype by CD4+ T-cells, Ann. Rev. Immunol. (1994), 12: 635-73.
Shan et al., "The role of cocrystals in pharmaceutical science," Drug Discovery Today (2008), 13(9/10), pp. 440-446.
Sharma et al., Distal effect on mass spectral fragmentations of glycolamide esters of 6-methoxy-2-naphthylacetic acid (6-MNA) and the crystal structure of N,N'-dimethyl-glycolamide ester of 6-MNA, Ind. J. Chem. (2004) 43B: 1758-1764.
Sheikh, et al., "Safety Tolerability and Pharmacokinetics of BG-12 Administered with and without Aspirin, Key Findings from a Randomized, Double-blind, placebo-controlled trial in healthy volunteers", Poster P04.136 presented at the 64th Annual Meeting of the American Academy of Neurology, Apr. 21-28, 2012, New Orleans, LA, 1 page.
Soelberg Sorensen et al., Oral fumarate for relapsing-remitting multiple sclerosis, Lancet (2008), 372: 1447-1448.
Spatz, et al., Methyl Hydrogen Fumarate, Journal of Organic Chemistry, 1958, 23 (10), 1559-1560.
Spencer et al., Induction of glutathione transferases and NAD(P)H:quinone reductase by fumaric acid derivatives in rodent cells and tissues, Cancer Res. (1990), 50: 7871-7875.
Spencer, "Tecfidera: an approach for repurposing," Pharmaceutical Patent Analyst, 2014, vol. 3(2), pp. 183-198.
Sprenger et al., "Characterization of the glutathione S-transferase GSTT1 deletion: discrimination of all genotypes by polymerase chain reaction indicates a trimodular genotype-phenotype correlation," Pharmacogenetics, 2000, vol. 10, pp. 557-565.
Stoof et al., The antipsoriatic drug dimethylfumarate strongly suppresses chemokine production in human keratinocytes and peripheral blood mononuclear cells, Br. J. Dermatol. (2001), 144: 1114-1120.
Tabruyn et al., NF-κB: a new player in angiostatic therapy. Angiogenesis (2008), 11, 101-106.
Talath et al., Stability studies of some glycolamide ester prodrugs of niflumic acid in aqueous buffers and human plasma by HPLC with UV detection, Arz. Forsch Drug Res. (2006), 56(9): 631-639.
Talath et al., Synthesis, stability studies, anti-inflammatory activity and ulcerogenicity of morpholinoalkyl ester prodrugs of niflumic acid, Arz. Forsch Drug Res. (2006), 56(11): 744-752.
Tang et al., The psoriasis drug monomethylfumarate is a potent nicotinic acid receptor agonist, Biochem. Biophys. Res. Comm. (2008), doi:10.1016/j.bbrc.2008.08.041, 4 pages.
Thing et al., "Prolonged naproxen joint residence time after intra-articular injection of lipophilic solutions comprising a naproxen glycolamide ester prodrug in the rat", International Journal of Pharmaceutics 451; Apr. 2013; pp. 34-40.
Thomson et al., FK 506: a novel immunosuppressant for treatment of autoimmune disease: rationale and preliminary clinical experience at the University of Pittsburgh, Springer Semin. Immunopathol. (1993), 14(4): 323-344.
Tracey et al., "Tumor necrosis factor antagonist mechanisms of action: a comprehensive review," Pharmacology & Therapeutics (2008), 117, pp. 244-279.
Treumer et al., Dimethylfumarate is a potent inducer of apoptosis in human T cells. J Invest Dermatol (2003), 121, 1383-1388.
Van Schoor et al., Effect of inhaled fluticasone on bronchial responsiveness to neurokinin A in asthma. Eur Respir J (2002), 19, 997-1002.
Van Schoor et al., The effect of the NK2 tachykinin receptor antagonist SR 48968 (saredutant) on neurokinin A-induced bronchoconstriction in asthmatics, Eur Respir J (1998) 12: 17-23.
Vandermeeren et al., Dimethylfumarate is an inhibitor of cytokine-induced E-selectin, VCAM-1, and ICAM-1 expression in human endothelial cells. Biochem Biophys Res Commun (1997), 234, 19-23.
Villegas et al., A new flavonoid derivative, dosmalfate, attenuates the development of dextran sulphate sodium-induced colitis in mice. Int'l Immunopharmacol (2003), 3, 1731-1741.
Virley, "Developing therapeutics for the treatment of multiple sclerosis," NeuroRx: The Journal of the American Society for Experimental NeuroTherapeutics (2005), vol. 2, pp. 638-649.
Vishweshwar et al., "Pharmaceutical Co-Crystals," Journal of Pharmaceutical Sciences (2006), 95(3), pp. 499-516.
Wadhwa et al., Glycolamide esters of 6-methoxy-2-naphthylacetic acid as potential prodrugs—Synthetic and spectral studies, Ind. J. Chem. (1995), 34B: 408-415.
Wain et al., Treatment of severe, recalcitrant, chronic plaque psoriasis with fumaric acid esters: a prospective study, Br. J. Dermatol. (2009), DOI 10.1111/j.1365-2133.2009.09267.x, 8 pages.
Wakkee et al., "Drug evaluation: BG-12, an immunomodulary dimethylfumarate," Current Opinion in Investigational Drugs (2007), 8(11), pp. 955-962.
Wang, et al., Evidence-Based Treatment of Chronic Leg Ulcers in a Patient with Necrobiosis Lipoidica Deabeticorum. Chinese Journal of Evidence-Based Medicine (2007), 7(11): 830-835.
Weber et al., Synthesis, In Vitro Skin Permeation Studies, and PLS-Analysis of New Naproxen Derivatives, Pharm. Res. (2001) 18(5): 600-607.
Weber et al., Treatment of disseminated granuloma annulare with low-dose fumaric acid, Acta Derm. Venereol. (2009), 89: 295-298.
Werdenberg et al., Presystemic metabolism and intestinal absorption of antipsoriatic fumaric acid esters, Biopharm. Drug. Dispos. (2003), 24: 259-273.
Whiteley et al., Models of Inflammation: Measuring Gastrointestinal Ulceration in the Rat, Curr. Protocol. Pharm. (1998): 10.2.1-10.2.4.
Wingerchuk et al., "Multiple sclerosis: current pathophysiological concepts," Laboratory Investigation (2001), 81(3), pp. 263-281.
Winkler, et al., Oxidative damage and age-related macular degeneration. Molecular vision, (1999), 5:32, 11 pages.

(56) References Cited

OTHER PUBLICATIONS

Woodworth et al., Oral BG-12 in combination with interferon beta or glatiramer acetate: pharmacokinetics, safety and tolerability, 26th Congress Eur. Cmtee. Treat. Res. Mult. Scler. (2010), poster: 1 page.
Woodworth et al., "Pharmacokinetics of Oral BG-12 Alone Compared with BG-12 and Interferon B-1a or Glatiramer Acetate Administered Together, Studied in Healthy Volunteers", Poster P04.207 presented at the 62nd Annual Meeting of the American Academy of Neurology, Apr. 10-17, 2010, Toronto, Ontario, Canada, 2 pages.
Wu et al., "Regulatory perspectives of Type II prodrug development and time-dependent toxicity management: Nonclinical Pharm/Tox analysis and the role of comparative toxicology", Science Direct, Toxicology 236; Apr. 2007; pp. 1-6.
Wustrow et al., Comparison of the efficacy and tolerability of a novel methyl hydrogenfumarate prodrug with dimethylfumarate in rodent EAE and GI irritation models, XenoPort, Inc., Oct. 13-16, 2010, 1 page.
Xenoport, Inc., XenoPort announces presentation of preclinical data for novel fumarate analog XP23829 at ECTRIMS, Press Release dated Oct. 13, 2010, 3 pages.
Yamada et al., "Synthesis and Polymerization of Unsaturated Dibasic Acid Derivatives," Yuki Gosei Kagaku Kyokaishi (1965), 23(2), 19 pages.
Yang et al., Neuroprotective effects of the triterpenoid, CDDO methyl amide, a potent inducer of Nrf2-mediated transcription, PLOS One (2009), 4(6) doi:10.1371/journal.pone.0005757: 13 pages.
Yazdi et al., Fumaric acid esters. Clinics Dermatology (2008), 26, 522-526.
Zhang et al., "Synthesis of Dimethyl Fumarate with Orthogonal Test," Jingxi Huagong Zhongjianti (2006), 36(6), pp. 71-72.
Zhao et al., "Synthesis and antimicrobial active of monomethyl fumarate," Shipin Gongye Keji (2008), 29(6), pp. 259-262.
Zheng et al., "Improved Preparation of Monomethyl Fumarate," Huaxue Shijie (2004), 45(4), pp. 207-208, 217.
Zhu et al., Inhibition of dendritic cell differentiation by fumaric acid esters, J. Invest. Dermatol. (2001), 116: 203-208.
The Engineering Tool Box, "Acids—pH Values," <http://www.engineeringtoolbox.com/acids-ph-d_401.html>, published Feb. 24, 2006, pp. 1-2.
Steckel et al., "The extrusion and speronization of chitosan," Pharmaceutical Technology Europe, <http://www.pharmtech.com/extrusion-and-spheronization-chitosan>, published Jul. 2, 2007, pp. 1-12.
Mannervik et al., "Identification of three classes of cytosolic glutathione transferase common to several mammalian species: Correlation between structural data and enzymatic properties," Proc. Natl. Acad. Sci., USA, Nov. 1985, vol. 82, pp. 7202-7206.
General pharmaceutics (5th edition), 1997, 5 pages, published in Japan.
Tammara et al., "Morpholinoalkyl Ester Prodrugs of Diclofenac: Synthesis, In Vitro and In Vivo Evaluation," Journal of Pharmaceutical Sciences, 1994 vol. 83, No. 5, pp. 644-648.
General pharmaceutics (5th edition) with partial translation of pp. 208-209, 1997, 5 pages, published in Japan.
Compound (CAS RN 473669-27-1) entered STN chemical database on Nov. 15, 2002 by Ambinter, 4 pp.
Booth et al., "Regulation of dimethyl-fumarate toxicity by proteasome inhibitors," Cancer Biology & Therapy, Dec. 2014, vol. 15(12), pp. 1646-1657.
Silhavy et al., "Fumaric Acid Esters Can Block Pro-Inflammatory Actions of Human CRP and Ameliorate Metabolic Disturbances in Transgenic Spontaneously Hypertensive Rats," PLOS One, Jul. 2014, vol. 9, Issue 7, e101906, pp. 1-9.
Maag et al., Prodrugs of Carboxylic Acids: Prodrugs, Challenges and Rewards Part 2, edited by Valentino J. Stella, Ronald T. Borchardt, Michael J. Hageman, Reza Oliyai, Hans Maag, Jefferson W. Tilley, chapter 3.1 by Hans Maag, 2007, 27 pages.
Litjens, N.H, et al., "In vitro pharmacokinetics of anti-psoriatic fumaric acid esters", BMC Pharmacology 2004, 4:22.

\* cited by examiner

Large API crystals on the surface of the pellet

ORAL DOSAGE FORMS OF METHYL HYDROGEN FUMARATE AND PRODRUGS THEREOF

This application is a divisional application of U.S. patent application Ser. No. 13/973,456, filed Aug. 22, 2013, which claims the benefit under 35 U.S.C. § 119(e) of U.S. Provisional Application Ser. No. 61/692,179 filed Aug. 22, 2012, 61/692,168, filed Aug. 22, 2012, 61/713,897 filed Oct. 15, 2012, 61/733,234 filed Dec. 4, 2012, 61/769,513 filed Feb. 26, 2013, 61/841,513 filed Jul. 1, 2013, 61/692,174 filed Aug. 22, 2012, and 61/713,961 filed Oct. 15, 2012, 61/837,796 filed Jun. 21, 2013 the contents of each of which are incorporated by reference in their entirety.

TECHNICAL FIELD

The present disclosure relates to oral dosage forms of methyl hydrogen fumarate (MHF) and prodrugs of MHF which are useful in treating conditions such as multiple sclerosis (MS) and/or psoriasis.

BACKGROUND

Fumaric acid esters, i.e., dimethylfumarate (DMF) in combination with salts of ethylhydrogenfumarate, have been used in the treatment of psoriasis for many years. The combination product, marketed under the tradename Fumaderm®, is in the form of oral tablets and is available in two different dosage strengths (Fumaderm® initial and Fumaderm®):

| Fumarate Compound | Fumaderm ® Initial (mg) | Fumaderm ® (mg) |
|---|---|---|
| Dimethylfumarate | 30 | 120 |
| Ethyl hydrogen fumarate, calcium salt | 67 | 87 |
| Ethyl hydrogen fumarate, magnesium salt | 5 | 5 |
| Ethyl hydrogen fumarate, zinc salt | 3 | 3 |

The two strengths are intended to be applied in an individually based dosing regimen starting with Fumaderm® initial in an escalating dose, and then after, e.g., three weeks of treatment, switching to Fumaderm®. Both Fumaderm® initial and Fumaderm® are enteric coated tablets.

Another marketed composition is Fumaraat 120® containing 120 mg of DMF and 95 mg of calcium monoethyl fumarate (TioFarma, Oud-Beijerland, Netherlands). The pharmacokinetic profile of Fumaraat 120® in healthy subjects is described in Litjens et al., Br. J. Clin. Pharmacol., 2004, vol. 58:4, pp. 429-432. The results show that a single oral dose of Fumaraat 120® is followed by a rise in serum MHF concentration and only negligible concentrations of DMF and fumaric acid is observed. Thus, DMF is thought to be a precursor or prodrug of MHF.

U.S. Pat. Nos. 6,277,882 and 6,355,676 disclose respectively the use of alkyl hydrogen fumarates and the use of certain fumaric acid monoalkyl ester salts for preparing microtablets for treating psoriasis, psoriatic arthritis, neurodermatitis and enteritis regionalis Crohn. U.S. Pat. No. 6,509,376 discloses the use of certain dialkyl fumarates for the preparation of pharmaceutical preparations for use in transplantation medicine or the therapy of autoimmune diseases in the form of microtablets or micropellets. U.S. Pat. No. 4,959,389 discloses compositions containing different salts of fumaric acid monoalkyl esters alone or in combination with a dialkyl fumarate. GB 1,153,927 relates to medical compositions comprising dimethyl maleic anhydride, dimethyl maleate and/or DMF.

Biogen Idec's BG12, an oral dosage form of DMF that is an enteric coated capsule containing DMF in micropellet form, has been in human clinical testing for the treatment of MS and has shown promising results in reducing MS relapses and MS disability progression. Unfortunately, DMF is highly irritating to the skin and mucosal membranes with the result that oral administration of DMF tends to cause serious digestive tract irritation with attendant nausea, vomiting, abdominal pain and diarrhea. This irritation problem is particularly problematic with the mucosal tissue lining the stomach. For this reason, products such as Fumaderm® and BG12 are made with enteric coatings that prevent the DMF from being released from the dosage form until after the dosage form passes out of the stomach and into the small intestine.

More recently, MHF prodrugs including (N,N-Diethylcarbamoyl)methyl methyl (2E)but-2-ene-1,4-dioate and (N,N-Dimethylcarbamoyl)methyl methyl (2E)but-2-ene-1,4-dioate are disclosed in Gangakhedkar et al. U.S. Pat. No. 8,148,414. Additional MHF prodrugs are disclosed in Cundy et al. U.S. Patent Application 61/595,835 filed Feb. 7, 2012. Both of these disclose the use of MHF prodrugs for treating a number of medical conditions, including MS and psoriasis.

SUMMARY

Disclosed herein are orally administered enteric coated tablet dosage forms of methyl hydrogen fumarate, or a prodrug of methyl hydrogen fumarate, having improved prodrug stability and shelf-life. The dosage forms are useful for treating conditions such as multiple sclerosis and psoriasis.

Fumaric acid esters such as methyl hydrogen fumarate and prodrugs of methyl hydrogen fumarate, e.g., dimethyl fumarate, have certain physical and chemical properties that cause problems when such compounds are used as therapeutic agents, particularly when administered orally to a patient. First, such compounds have been shown to cause skin irritation. Second, such compounds exhibit degrees of chemical instability upon exposure to light, including ultra violet light. Third, such compounds have been shown to cause flushing in certain patients and/or at certain dosages. Fourth, certain fumarate compounds (i.e., dimethyl fumarate) have been shown to cause adverse interactions with the endothelial tissues lining the stomach, causing severe tissue damage and attendant gastrointestinal distress and symptoms such as nausea and abdominal pain and diarrhea. Fifth such compounds tend to be chemically less stable at low pH levels (e.g., pH≤2), compared to near neutral pH levels (e.g., pH of 3 to 6) with the result that the compounds can chemically break down into non-therapeutic metabolites in the low pH environs of the stomach. While enteric coatings have previously been proposed for certain fumarate dosage forms, it has now been discovered that these fumarate compounds tend to exhibit poor chemical stability in the presence of such enteric coating materials.

These and other problems are solved by an oral dosage form containing a therapeutically effective amount of a compound selected from (i) methyl hydrogen fumarate (MHF), (ii) a prodrug of MHF, pharmaceutically acceptable salts thereof and combinations thereof. The dosage form has a core containing the compound, and an enteric coating surrounding the core. The enteric coating is comprised of an enteric polymer having carboxylic acid moieties, the enteric polymer (i) being soluble in aqueous solutions having a pH above 7.5, and (ii) starting to become soluble in an aqueous solution at a pH in the range of 4.5 to 7.5.

A barrier layer is disposed between the compound-containing core and the enteric coating to prevent direct contact between the compound-containing core and the enteric coating. In various aspects, the barrier layer is composed of a material that is either (i) a weakly acidic (proton-donating) material having a pKa of greater than 8, (ii) a weakly basic (proton-accepting) material having a pKa of less than 2, (iii) a natural gum or polysaccharide, (iv) a neutral polymer salt, (v) a sugar, or (vi) a lipid.

In further aspects, the barrier layer comprises a polymer that is either (i) weakly acidic (proton-donating) having a pKa of greater than 10, or (ii) weakly basic (proton-accepting) having a pKa of less than 0.

In certain embodiments, the barrier layer material is a non-ionizable polymer. In other embodiments, the barrier layer material is selected from non-ionizable cellulosic polymers, non-ionizable vinyl polymers, and non-ionizable non-vinyl, non-cellulosic polymer and/or sugars. In various other aspects, the barrier layer can comprise a natural gum or polysaccharide, neutral polymer salts, readily ionizable polymers lacking carboxylic acid moieties, sugars, or lipids. In certain embodiments, the barrier layer comprises at least 5 wt % of the coated core for cores having a size of 2 mm or less. In other embodiments, the barrier layer comprises at least 1 wt % of the coated core for cores having a size greater than 6 mm. In certain embodiments, the barrier layer has an average thickness of at least 5 μm. In other embodiments, the barrier layer has an average thickness of at least 15 μm. In still other embodiments, the barrier layer material is either (i) a weakly acidic (proton-donating) material having a pKa of greater than 10, or (ii) a weakly basic (proton-accepting) material having a pKa of less than 0.

In various embodiments, the barrier layer material can be substantially free of carboxylic acid moieties.

In certain embodiments, the fumarate compound comprises methyl hydrogen fumarate. In other embodiments, the fumarate compound comprises a prodrug of methyl hydrogen fumarate. In still other embodiments, the fumarate compound is a prodrug of methyl hydrogen fumarate selected from dimethyl fumarate, (N,N-Diethylcarbamoyl)methyl methyl (2E)but-2-ene-1,4-dioate, (N,N-Dimethylcarbamoyl)methyl methyl (2E)but-2-ene-1,4-dioate, and combinations thereof.

In certain embodiments, the core is a compressed tablet and the barrier layer and enteric coating are each a coating on the tablet. In other embodiments, the dosage form is a capsule containing a multiplicity of said enteric coated cores.

In certain embodiments, the core comprises an immediate release dosage form. In other embodiments, the core comprises a sustained release dosage form.

The enteric polymer can be selected from methacrylic acid polymers, cellulose acetate phthalate polymers, hydroxypropylmethyl cellulose acetate succinate polymers, hydroxypropylmethyl cellulose phthalate polymers and polyvinyl acetate phthalate polymers.

Also provided is a method of treating a disease in a patient, comprising orally administering to a patient in need thereof a dosage form as described above. The dosage forms are particularly useful for treating multiple sclerosis and/psoriasis.

Also provided is a method of making (N,N-Diethylcarbamoyl)methyl methyl (2E)but-2-ene-1,4-dioate-containing pharmaceutical pellets. The method includes providing the (N,N-Diethylcarbamoyl)methyl methyl (2E)but-2-ene-1,4-dioate in an aqueous medium containing acetic acid while maintaining the aqueous medium at a pH at or below 3.8 so that the acetic acid remains in a predominantly non-ionized state. In certain embodiments, the aqueous medium is maintained at a pH at or below 3.5. Upon drying, the pellets demonstrate a greatly reduced tendency to agglomerate.

DEFINITIONS

Figure 1:
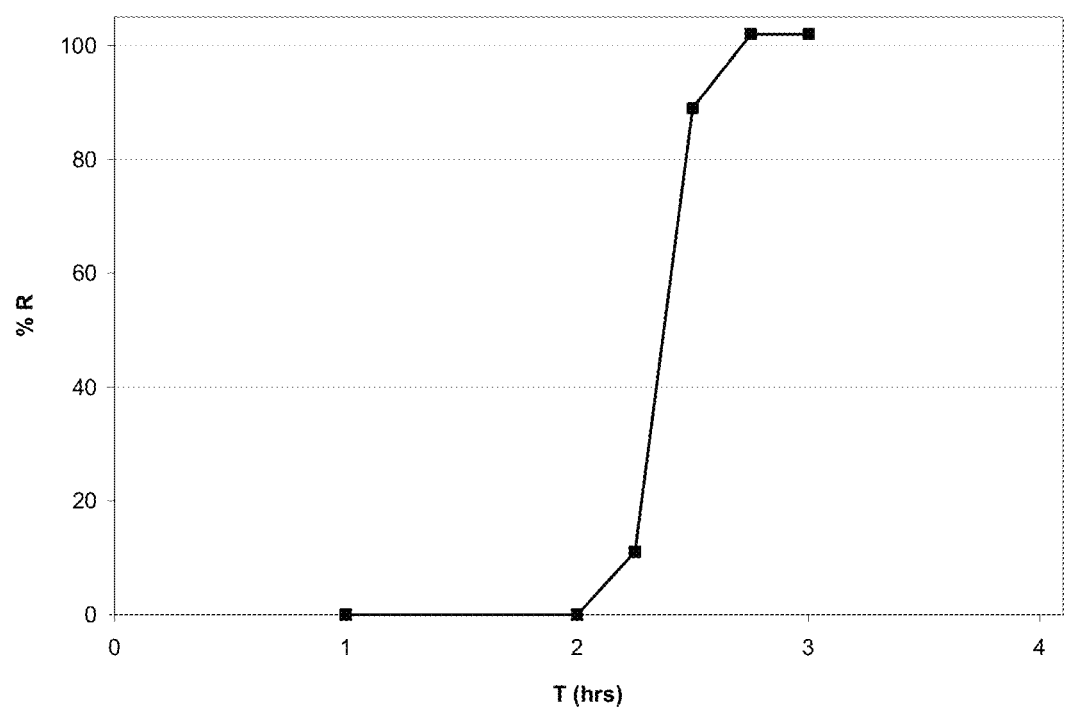
FIG. 1 is a graph showing the in vitro MHF prodrug release profile (percent MHF prodrug released over time) for the dosage forms of Example 1, tested in accordance with Example 3.

A dash ("-") that is not between two letters or symbols is used to indicate a point of attachment for a moiety or substituent. For example, —CONH$_2$ is bonded through the carbon atom.

"Alkyl" refers to a saturated or unsaturated, branched, cyclic, or straight-chain, monovalent hydrocarbon radical derived by the removal of one hydrogen atom from a single carbon atom of a parent alkane, alkene, or alkyne. Examples of alkyl groups include, for example, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, cyclopropyl, cyclobutyl, cyclopentyl, etc.; and the like.

The term "alkyl" includes groups having any degree or level of saturation, i.e., groups having exclusively single carbon-carbon bonds, groups having one or more double carbon-carbon bonds, groups having one or more triple carbon-carbon bonds, and groups having combinations of single, double, and triple carbon-carbon bonds. Where a specific level of saturation is intended, the terms alkanyl, alkenyl, or alkynyl are used. The term "alkyl" includes cycloalkyl and cycloalkylalkyl groups. In certain embodiments, an alkyl group can have from 1 to 10 carbon atoms ($C_{1-10}$), in certain embodiments, from 1 to 6 carbon atoms ($C_{1-6}$), in certain embodiments from 1 to 4 carbon atoms ($C_{1-4}$), in certain embodiments, from 1 to 3 carbon atoms ($C_{1-3}$), and in certain embodiments, from 1 to 2 carbon atoms ($C_{1-2}$). In certain embodiments, alkyl is methyl, in certain embodiments, ethyl, and in certain embodiments, n-propyl or isopropyl.

"Arylalkyl" refers to an acyclic alkyl radical in which one of the hydrogen atoms bonded to a carbon atom, typically a terminal or sp$^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl, or arylalkynyl is used. In certain embodiments, an arylalkyl group is $C_{7-30}$ arylalkyl, e.g., the alkanyl, alkenyl or alkynyl moiety of the arylalkyl group is $C_{1-10}$ and the aryl moiety is $C_{6-20}$, in certain embodiments, an arylalkyl group is $C_{6-18}$ arylalkyl, e.g., the alkanyl, alkenyl or alkynyl moiety of the arylalkyl group is $C_{1-8}$ and the aryl moiety is $C_{6-10}$. In certain embodiments, an arylalkyl group is $C_{7-12}$ arylalkyl.

"AUC" refers to the area under a curve on which time is plotted on the X-axis and concentration of a substance (e.g., MHF) in blood or blood plasma is plotted on the Y-axis over a particular period of time (e.g., time zero to 24 hours). AUC is commonly expressed in units of mg-hr/ml.

"Compounds" include MHF and MHF prodrugs. MHF products include DMF and the compounds of Formula (I) or Formula (II) including any specific compounds within these formulae. Compounds may be identified either by their chemical structure and/or chemical name. Compounds are named using Chemistry 4-D Draw Pro, version 7.01c (ChemInnovation Software, Inc., San Diego, Calif.). When the chemical structure and chemical name conflict, the chemical structure is determinative of the identity of the compound. The compounds described herein may comprise one or more chiral centers and/or double bonds and therefore may exist as stereoisomers such as double bond isomers (i.e., geometric isomers), enantiomers, or diastereomers. Accordingly, any chemical structures within the scope of the specification depicted, in whole or in part, with a relative configuration are deemed to encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to those skilled in the art. Compounds of Formula (I) or Formula (II) include, for example, optical isomers of compounds of Formula (I) or Formula (II), racemates thereof, and other mixtures thereof. In such embodiments, a single enantiomer or diastereomer, i.e., optically active form, can be obtained by asymmetric synthesis or by resolution of the racemates. Resolution of the racemates may be accomplished, for example, by methods such as crystallization in the presence of a resolving agent, or chromatography using, for example, chiral stationary phases. Notwithstanding the foregoing, in compounds of Formula (I) or Formula (II) the configuration of the illustrated double bond is only in the E configuration (i.e., trans configuration).

MHF and MHF prodrug compounds also include isotopically labeled compounds where one or more atoms have an atomic mass different from the atomic mass conventionally found in nature. Examples of isotopes that may be incorporated into the compounds disclosed herein include, for example, $^2$H, $^3$H, $^{11}$C, $^{13}$C, $^{14}$C, $^{15}$N, $^{18}$O, $^{17}$O, etc. Compounds may exist in unsolvated forms as well as solvated forms, including hydrated forms and as N oxides. In general, compounds disclosed herein may be free acid, hydrated, solvated, or N oxides. Certain compounds may exist in multiple crystalline, co-crystalline, or amorphous forms. Compounds of Formula (I) or Formula (II) include pharmaceutically acceptable salts thereof or pharmaceutically acceptable solvates of the free acid form of any of the foregoing, as well as crystalline forms of any of the foregoing.

MHF and MHF prodrug compounds also include solvates. A solvate refers to a molecular complex of a compound with one or more solvent molecules in a stoichiometric or non-stoichiometric amount. Such solvent molecules include those commonly used in the pharmaceutical art, which are known to be innocuous to a patient, e.g., water, ethanol, and the like. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules are water.

Further, when partial structures of the compounds are illustrated, an asterisk (*) indicates the point of attachment of the partial structure to the rest of the molecule.

"Controlled-release" refers to release of a drug from a dosage form in which the drug release is controlled or modified over a period of time. Controlled can mean, for example, sustained, delayed, or pulsed-release at a particular time. Controlled can also mean that release of the drug from the dosage form is extended for longer than it would be in an immediate-release dosage form, i.e., at least over several hours. In some embodiments, in vivo release of the compound occurs over a period of at least 2 hours, in some embodiments, over a period of at least about 4 hours, in some embodiments, over a period of at least about 8 hours, in some embodiments over a period of at least about 12 hours, in some embodiments, over a period of at least about 16 hours, in some embodiments, over a period of at least about 20 hours, and in some embodiments, over a period of at least about 24 hours.

"Cycloalkyl" refers to a saturated or partially unsaturated cyclic alkyl radical. Where a specific level of saturation is intended, the nomenclature cycloalkanyl or cycloalkenyl is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, $C_{3-12}$ cycloalkyl, and in certain embodiments, $C_{3-8}$ cycloalkyl.

"Cycloalkylalkyl" refers to an acyclic alkyl radical in which one of the hydrogen atoms bonded to a carbon atom, typically a terminal or $sp^3$ carbon atom, is replaced with a cycloalkyl group. Where specific alkyl moieties are intended, the nomenclature cycloalkylalkanyl, cycloalkylalkenyl, or cycloalkylalkynyl is used. In certain embodiments, a cycloalkylalkyl group is $C_{4-30}$ cycloalkylalkyl, e.g., the alkanyl, alkenyl, or alkynyl moiety of the cycloalkylalkyl group is $C_{1-10}$ and the cycloalkyl moiety is $C_{3-20}$, and in certain embodiments, a cycloalkylalkyl group is $C_{3-20}$ cycloalkylalkyl, e.g., the alkanyl, alkenyl, or alkynyl moiety of the cycloalkylalkyl group is $C_{1-8}$ and the cycloalkyl moiety is $C_{3-12}$. In certain embodiments, a cycloalkylalkyl group is $C_{4-12}$ cycloalkylalkyl.

"Dosage form" refers to a form of a formulation that contains an amount of active agent or prodrug of an active agent, e.g. the compounds described herein, which can be administered to a patient to achieve a therapeutic effect. An oral dosage form is intended to be administered to a patient via the mouth and swallowed. A dose of a drug may include one or more dosage forms administered simultaneously or over a period of time.

"Disease" refers to a disease, disorder, condition, or symptom of any of the foregoing.

"Drug" as defined under 21 U.S.C. § 321 (g)(1) means "(A) articles recognized in the official United States Pharmacopoeia, official Homeopathic Pharmacopoeia of the United States, or official National Formulary, or any supplement to any of them; and (B) articles intended for use in the diagnosis, cure, mitigation, treatment, or prevention of disease in man or other animals; and (C) articles (other than food) intended to affect the structure or any function of the body of man or other animals . . . ."

"Heteroalkyl" by itself or as part of another substituent refer to an alkyl group in which one or more of the carbon atoms (and certain associated hydrogen atoms) are independently replaced with the same or different heteroatomic groups. Examples of heteroatomic groups include, but are not limited to, —O—, —S—, —O—O—, —S—S—, —O—S—, —NR$^{13}$, =N—N=, —N=N—, —N=N—NR$^{13}$—, —PR$^{13}$—, —P(O)$_2$—, —POR$^{13}$—, —O—P(O)$_2$—, —SO—, —SO$_2$—, —Sn(R$^{13}$)$_2$—, and the like, where each $R^{13}$ is independently chosen from hydrogen, $C_{1-6}$ alkyl, substituted $C_{1-6}$ alkyl, $C_{6-12}$ aryl, substituted $C_{6-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-6}$ heteroalkyl, substituted $C_{1-6}$ heteroalkyl, $C_{6-12}$ heteroaryl, substituted $C_{6-12}$ heteroaryl, $C_{7-18}$ heteroarylalkyl, or substituted $C_{7-18}$ heteroarylalkyl. Reference to, for example, a $C_{1-6}$ heteroalkyl, means a $C_{1-6}$ alkyl group in which at least one of the carbon atoms (and certain associated hydrogen atoms) is replaced with a heteroatom. For example $C_{1-6}$ heteroalkyl includes groups having five carbon atoms and one heteroatom, groups having four carbon atoms and two heteroatoms, etc. In certain embodiments, each $R^{13}$ is independently chosen from hydrogen and $C_{1-3}$ alkyl. In certain embodiments, a heteroatomic group is chosen from —O—, —S—, —NH—, —N(CH$_3$)—, and —SO$_2$—; and in certain embodiments, the heteroatomic group is —O—.

"Heteroaryl" refers to a monovalent heteroaromatic radical derived by the removal of one hydrogen atom from a single atom of a parent heteroaromatic ring system. Heteroaryl encompasses multiple ring systems having at least one heteroaromatic ring fused to at least one other ring, which can be aromatic or non-aromatic. For example, heteroaryl encompasses bicyclic rings in which one ring is heteroaromatic and the second ring is a heterocycloalkyl ring. For such fused, bicyclic heteroaryl ring systems wherein only one of the rings contains one or more heteroatoms, the radical carbon may be at the aromatic ring or at the heterocycloalkyl ring. In certain embodiments, when the total number of N, S, and O atoms in the heteroaryl group exceeds one, the heteroatoms are not adjacent to one another. In certain embodiments, the total number of heteroatoms in the heteroaryl group is not more than two.

"Heterocycloalkyl" refers to a saturated or unsaturated cyclic alkyl radical in which one or more carbon atoms (and certain associated hydrogen atoms) are independently replaced with the same or different heteroatom; or to a parent aromatic ring system in which one or more carbon atoms (and certain associated hydrogen atoms) are independently replaced with the same or different heteroatom such that the ring system no longer contains at least one aromatic ring. Examples of heteroatoms to replace the carbon atom(s) include, but are not limited to, N, P, O, S, Si, etc. Examples of heterocycloalkyl groups include, but are not limited to, groups derived from epoxides, azirines, thiiranes, imidazolidine, morpholine, piperazine, piperidine, pyrazolidine, pyrrolidine, quinuclidine, and the like. In certain embodiments, a heterocycloalkyl group is $C_{4-10}$ heterocycloalkyl, $C_{4-8}$ heterocycloalkyl, and in certain embodiments, $C_{4-6}$ heterocycloalkyl.

"Immediate release" refers to formulations or dosage forms that rapidly dissolve in vitro and in vivo and are intended to be completely dissolved and absorbed in the stomach or upper gastrointestinal tract. Immediate release formulations can release at least 90% of the active ingredient or precursor thereof within about 15 minutes, within about 30 minutes, within about one hour, or within about two hours of administering an immediate release dosage form.

"Leaving group" has the meaning conventionally associated with it in synthetic organic chemistry, i.e., an atom or a group capable of being displaced by a nucleophile and includes halogen such as chloro, bromo, fluoro, and iodo; acyloxy, such as acetoxy and benzoyloxy, alkoxycarbonylaryloxycarbonyl, mesyloxy, tosyloxy, and trifluoromethanesulfonyloxy; aryloxy such as 2,4-dinitrophenoxy, methoxy, N,O-dimethylhydroxylamino, p-nitrophenolate, imidazolyl, and the like.

"MHF" refers to methyl hydrogen fumarate, a compound having the following chemical structure:

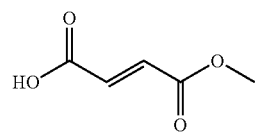

This compound is also sometimes referred to as monomethyl fumarate.

"MHF Prodrug" refers to a prodrug that is metabolized in vivo to form methyl hydrogen fumarate as a pharmacologically active metabolite.

"Parent heteroaromatic ring system" refers to an aromatic ring system in which one or more carbon atoms (and any associated hydrogen atoms) are independently replaced with the same or different heteroatom in such a way as to maintain the continuous π-electron system characteristic of aromatic systems and a number of out-of-plane π-electrons corresponding to the Hickel rule (4n+2). Examples of heteroatoms to replace the carbon atoms include, for example, N, P, O, S, and Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, for example, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, oxazolidine, and the like.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound that possesses the desired pharmacological activity of the parent compound. Such salts include acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N methylglucamine, and the like. In certain embodiments, a pharmaceutically acceptable salt is the hydrochloride salt. In certain embodiments, a pharmaceutically acceptable salt is the sodium salt.

"Pharmaceutically acceptable excipient" refers to a pharmaceutically acceptable diluent, a pharmaceutically acceptable adjuvant, a pharmaceutically acceptable vehicle, a pharmaceutically acceptable carrier, or a combination of any of the foregoing with which a compound provided by the present disclosure may be administered to a patient, which does not destroy the pharmacological activity thereof and which is non-toxic when administered in doses sufficient to provide a therapeutically effective amount of the compound or a pharmacologically active metabolite thereof.

"Prodrug" refers to a compound administered in a pharmacologically inactive (or significantly less active) form. Once administered, the compound is metabolized in vivo into an active metabolite. Prodrugs may be designed to improve oral bioavailability, particularly in cases where the metabolite exhibits poor absorption from the gastrointestinal tract. Prodrugs can be used to optimize the absorption, distribution, metabolism, and excretion (ADME) of the active metabolite.

A composition or material that is "substantially free of carboxylic acid moieties" is a composition or material that has less than 2% w/w of carboxylic acid moieties. In some embodiments, a composition or material that is "substantially free of carboxylic acid moieties" is a composition or material that has less than 1% w/w of carboxylic acid moieties. In other embodiments, a composition or material that is "substantially free of carboxylic acid moieties" is a composition or material that has less than 0.01% w/w of carboxylic acid moieties.

"Substituent" refers to a group in which one or more hydrogen atoms are independently replaced (or substituted) with the same or substituent group(s). In certain embodiments, each substituent group is independently chosen from halogen, —OH, —CN, —CF$_3$, =O, —NO$_2$, benzyl, —C(O)NH$_2$, —R$^{11}$, —OR$^{11}$, —C(O)R$^{11}$, —COOR$^{11}$, and —NR$^{11}_2$ wherein each R$^{11}$ is independently chosen from hydrogen and C$_{1-4}$ alkyl. In certain embodiments, each substituent group is independently chosen from halogen, —OH, —CN, —CF$_3$, —NO$_2$, benzyl, —R$^{11}$, —OR$^{11}$, and —NR$^{11}_2$ wherein each R$^{11}$ is independently chosen from hydrogen and C$_{1-4}$ alkyl. In certain embodiments, each substituent group is independently chosen from halogen, —OH, —CN, —CF$_3$, =O, —NO$_2$, benzyl, —C(O)NR$^{11}_2$, —R$^{11}$, —OR$^{11}$, —C(O)R$^{11}$, —COOR$^{11}$, and —NR$^{11}_2$ wherein each R$^{11}$ is independently chosen from hydrogen and C$_{1-4}$ alkyl. In certain embodiments, each substituent group is independently chosen from —OH, C$_{1-4}$ alkyl, and —NH$_2$.

"Sustained-release" refers to release of a drug from a dosage form in which the drug release occurs over a period of time. Sustained release can mean that release of the drug from the dosage form is extended for longer than it would be in an immediate-release dosage form, i.e., at least over several hours. In some embodiments, in vivo release of the compound occurs over a period of at least 2 hours, in some embodiments, over a period of at least about 4 hours, in some embodiments, over a period of at least about 8 hours, in some embodiments over a period of at least about 12 hours, in some embodiments, over a period of at least about 16 hours, in some embodiments, over a period of at least about 20 hours, and in some embodiments, over a period of at least about 24 hours.

"Treating" or "treatment" of any disease refers to reversing, alleviating, arresting, or ameliorating a disease or at least one of the clinical symptoms of a disease, reducing the risk of acquiring at least one of the clinical symptoms of a disease, inhibiting the progress of a disease or at least one of the clinical symptoms of the disease or reducing the risk of developing at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter that may or may not be discernible to the patient. In certain embodiments, "treating" or "treatment" refers to protecting against or delaying the onset of at least one or more symptoms of a disease in a patient.

"Therapeutically effective amount" refers to the amount of a compound that, when administered to a subject for treating a disease, or at least one of the clinical symptoms of a disease, is sufficient to effect such treatment of the disease or symptom thereof. The "therapeutically effective amount" may vary depending, for example, on the compound, the disease and/or symptoms of the disease, severity of the disease and/or symptoms of the disease, the age, weight, and/or health of the patient to be treated, and the judgment of the prescribing physician. An appropriate amount in any given compound may be ascertained by those skilled in the art and/or is capable of determination by routine experimentation.

"Therapeutically effective dose" refers to a dose that provides effective treatment of a disease in a patient. A therapeutically effective dose may vary from compound to compound and/or from patient to patient, and may depend upon factors such as the condition of the patient and the severity of the disease. A therapeutically effective dose may be determined in accordance with routine pharmacological procedures known to those skilled in the art.

Reference is now made in detail to certain embodiments of compounds, dosage forms, compositions, and methods. The disclosed embodiments are not intended to be limiting of the claims. To the contrary, the claims are intended to cover all alternatives, modifications, and equivalents.

DETAILED DESCRIPTION

The dosage forms disclosed herein have a core containing a therapeutically effective amount of a compound selected from (i) methyl hydrogen fumarate (MHF), (ii) a prodrug of MHF, pharmaceutically acceptable salts of (i) or (ii), and combinations of any of the foregoing. In various embodiments, the dosage form can be a compound-containing pharmaceutical tablet or a plurality of compound-containing pellets or granules contained in a capsule or further compressed into a tablet. In either case, the core is surrounded by a barrier layer that prevents direct contact between the core and an enteric coating. It will be understood that additional layers and/or materials optionally may be disposed between the tablet core and the barrier layer. It will also be understood that additional layers and/or materials optionally may be disposed between the barrier layer and the tablet core.

Surprisingly, the fumarate compounds disclosed herein have been found to exhibit varying degrees of chemical instability when in direct contact with ionizable polymers of the type conventionally found in enteric coatings. Without wishing to be held to a particular theory or mechanism of action, the degree of fumarate prodrug chemical instability can correspond to the carboxylic acid moiety content of the enteric polymer. By introducing a barrier layer between the tablet core and the enteric coating, the instability of the fumarate compounds is surprisingly reduced.

A. Barrier Layer

In various embodiments, the barrier layer disposed between the tablet core and the enteric coating layer comprises a material that is (i) a weakly acidic (proton-donating) material having a pKa of greater than 8, (ii) a weakly basic (proton-accepting) material having a pKa of less than 2, (iii) a natural gum or polysaccharide, (iv) a neutral polymer salt, (v) a sugar, or (vi) a lipid. The pKa values for various compounds may be calculated or measured as understood in the art. A carboxylic acid enteric coating surrounds the barrier layer such that the barrier layer prevents contact between the core and the enteric coating.

The barrier layer comprises one or more materials that will not cause premature breakdown of the fumarate compound during product shelf life.

Surprisingly, MHF and MHF prodrugs have been found to have poor stability when placed in contact with ionizable polymers having carboxylic acid moieties of the type that are commonly used in enteric coatings. Thus, in certain embodiments the barrier layer is substantially free of ionizable polymers having carboxylic acid moieties of the types mentioned above.

1. Non-Ionizable Polymers

In various aspects, the barrier layer can comprise one or more non-ionizable polymers. As used herein, non-ionizable polymers are materials that are either (i) proton-donating acidic materials having a pKa of greater than 8, (ii) proton-accepting basic materials having a pKa of less than 2. Examples of suitable non-ionizable polymers include non-ionizable cellulosic polymers, non-ionizable vinyl and polyvinyl alcohol polymers, and/or non-ionizable polymers that are not cellulose or vinyl-based.

In various embodiments, non-ionizable polymers are substantially free of carboxylic acid moieties.

a. Non-Ionizable Cellulosic Polymers

In some variations, the barrier layer comprises a non-ionizable cellulosic polymer. Specific examples of non-ionizable cellulosic polymers include methylcellulose, ethylcellulose, propylcellulose, butylcellulose, cellulose acetate, cellulose propionate, cellulose butyrate, cellulose acetate butyrate, cellulose acetate propionate, methyl cellulose, methyl cellulose acetate, methyl cellulose propionate, methyl cellulose butyrate, ethyl cellulose acetate, ethyl cellulose propionate, ethyl cellulose butyrate, hydroxymethyl cellulose, hydroxyethyl cellulose, hydroxyethyl methyl cellulose, hydroxypropyl cellulose, hydroxybutyl cellulose, hydroxyethyl cellulose acetate, hydroxyethyl ethyl cellulose, low-substituted hydroxypropyl cellulose, hydroxypropyl methylcellulose, hydroxypropyl methylcellulose acetate, hydroxypropyl methylcellulose propionate, hydroxypropyl methylcellulose butyrate, and corresponding salts and esters.

b. Non-Ionizable Vinyl-Based Polymers

In some variations, the barrier layer comprises a non-ionizable vinyl-based polymer. Exemplary vinyl-based polymers include polyvinyl alcohol, polyvinvyl acetate, polyvinylpyrrolidone, and crospovidone (polymers of N-vinyl-2-pyrrolidone). Exemplary vinyl-containing polymers further include vinyl polymers and copolymers having hydroxyl-containing repeat units, alkylacyloxy-containing repeat units, or cyclicamido-containing repeat units. Further exemplary vinyl-containing polymers also include polyvinyl alcohols that have at least a portion of their repeat units in the unhydrolyzed (vinyl acetate) form, polyvinylhydroxyethyl ether, polyvinyl alcohol polyvinyl acetate copolymers, polyvinyl pyrrolidone, polyvinylpyrrolidone-polyvinvylacetate copolymers, polyethylene polyvinyl alcohol copolymers, and polyoxyethylene-polyoxypropylene copolymers. In alternate embodiments, vinyl copolymers can include a second polymer can having (1) substantially carboxy-free hydroxyl-containing repeat units and (2) hydrophobic repeat units.

In certain embodiments, the non-ionizable polyvinyl materials show no degradation as an excipient. Non-limiting examples of such materials include polyvinylpyrrolidone and crospovidone.

c. Non-Ionizable Polymer that is Neither Cellulose Nor Vinyl Based

In some variations, the barrier layer comprises non-cellulosic non-vinyl-based non-ionizable polymers. Examples of such polymers included poly(lactide) poly (glycolide), poly(ε-caprolactone), poly(lactide-co-glycolide), poly(lactide-co-ε-caprolactone), poly(ethylene oxide-co-ε-caprolactone), poly(ethylene oxide-co-lactide), poly(ethylene oxide-co-lactide-co-glycolide), poly(isobutyl) cyanoacrylate, and poly(hexyl)cyanoacrylate, polyethylene glycol, polyethylene glycol, polypropylene glycol copolymers, polyoxyethylene-polyoxypropylene block copolymers, polyethylene oxide, poly(ethyl acrylate-co-methyl methacrylate) 2:1 (Eudragit NE), polyethylene glycol, polyethylene glycol polypropylene glycol copolymers, and polyoxyethylene-polyoxypropylene block copolymers (i.e. poloaxamers). In some variations, non-ionizable polymers such as polyoxyethylene-polyoxypropylene block copolymers show no degradation as an excipient. In certain variations, the non-cellulosic non-vinyl based non-ionizable polymers do not contain carboxylic acid moieties, or are substantially free of carboxylic acid moieties.

2. Natural Gums and Polysaccharides

In some variations, the barrier layer comprises a natural gum or polysaccharide. Suitable examples of such natural gums and polysaccharides include starch, chitin, guar gum, tara gum, locust bean gum, carrageenan, gellan gum, alginate, and xanthan gum.

In certain embodiments, the natural gums and polysaccharides contain carboxylic acid moieties, including salts thereof. Non-limiting examples of such materials include gellan gum, Alginate, and xanthan gum.

In various embodiments, natural gum or polysaccharides are substantially free of carboxylic acid moieties. Non-limiting examples of such materials include starch, chitin, guar gum, tara gum, locust bean gum, and carrageenan, among others.

3. Neutral Polymer Salts

In some variations, the barrier layer comprises a neutral polymer salt. Non-limiting examples of such neutral polymer salts include poly(ethyl acrylate-co-methyl methacrylate-co-trimethylammonioethyl methacrylate chloride) 1:2:0.1, Poly(ethyl acrylate-co-methyl methacrylate-co-trimethylammonioethyl methacrylate chloride) 1:2:0.2, crosslinked sodium carboxymethyl cellulose (croscarmellose sodium), crosslinked sodium carboxymethyl cellulose (sodium starch glycolate), salts of carboxymethyl cellulose, salts of carboxyethyl cellulose, salts of carboxypropyl cellulose, salts of carboxybutyl cellulose, salts of carboxymethyl starch, and salts of carboxyethyl starch. In certain embodiments, the neutral polymer salts do not include a carboxylate group.

In certain embodiments, the neutral polymer salts do not degrade as excipients. Non-limiting examples of such materials include poly(ethyl acrylate-co-methyl methacrylate-co-trimethylammonioethyl methacrylate chloride) 1:2:0.1, poly (ethyl acrylate-co-methyl methacrylate-co-trimethylammonioethyl methacrylate chloride) 1:2:0.2, and croscarmellose sodium.

In certain embodiments, certain neutral polymer salts do not include carboxyl groups. These materials include poly (ethyl acrylate-co-methyl methacrylate-co-trimethylammonioethyl methacrylate chloride) 1:2:0.1 and poly(ethyl acrylate-co-methyl methacrylate-co-trimethylammonioethyl methacrylate chloride) 1:2:0.2

In certain embodiments, certain neutral polymer salts include a carboxyl group that is neutralized with a counterion. Such compounds include crosslinked croscarmellose, crosslinked sodium carboxymethyl cellulose (sodium starch glycolate), salts of carboxymethyl cellulose, salts of carboxyethyl cellulose, salts of carboxypropyl cellulose, salts of carboxybutyl cellulose, salts of carboxymethyl starch, and salts of carboxyethyl starch.

In certain other embodiments, the ionizable polymers do not contain carboxylic acid groups. Such materials include poly(butyl methacylate-co-(2-dimethylaminoethyl) methacrylate-co-methyl methacrylate) 1:2:1 (Eudragit E), chitosan, and methyl methacrylate diethylaminoethyl methacrylate copolymer. Eudragit E has polymer free amino groups, and is neutral at pH>5 and prontonated at pH<5.

4. Sugars

In some variations, the barrier layer comprises a sugar. Examples of suitable sugars include lactose, mannitol, sorbitol, sucrose, and trehalose.

5. Lipids

In some variations, the compression coating layer comprises a lipid. Examples of suitable lipids are glyceryl behenate, castor oil, hydrogenated vegetable oil, hydrogenated carnauba wax and microcrystalline wax. In certain variations, the lipids are substantially free of carboxylic acid moieties.

In various aspects, the barrier layer is sufficiently thick and sufficiently continuous to prevent direct contact between the enteric coating and the core. Typically this can be accomplished by coating the cores to a target weight percent range. For cores having a size (e.g., diameter) of 2 mm or less, the barrier layer can comprise at least 5 wt % of the coated core. For cores having a size (e.g., diameter) greater than 6 mm, the barrier layer comprises at least 0.5 wt % of the coated core.

Alternatively, the barrier layer can be applied to a specified average thickness. For example, the barrier layer can have an average thickness of at least 5 μm. In other embodiments, the barrier layer has an average thickness of at least 15 μm.

B. Enteric Coatings

Once the cores have been coated with the barrier layer, an enteric coating is then applied. In various embodiments, the enteric coating comprises an enteric polymer that is substantially insoluble in aqueous solutions having a pH level below 4.5 but which starts to become soluble at a pH between 4.5 and 7.5 and is soluble in aqueous solutions having a pH above 7.5. The enteric coating remains intact while the oral dosage form is in the low pH environs of the stomach, which means that the fumarate compound remains in the core while the dosage form is in the stomach.

Suitable enteric polymers include methacrylic acid polymers, cellulose acetate phthalate polymers, hydroxypropylmethyl cellulose acetate succinate polymers, hydroxypropylmethyl cellulose phthalate polymers and polyvinyl acetate phthalate polymers. Other examples of pH-sensitive polymers that can be used in the enteric coating include methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers and shellac. Specific examples of enteric polymers include hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, carboxymethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

C. Tablet Cores

As noted herein, the tablet cores can be in the form of compressed tablets, or a plurality of compound-containing pellets or granules contained in a capsule.

1. Cores in the Form of Compressed Tablets

Compressed tablet cores containing a fumarate compound can be made using well known techniques such as those described in Remington: The Science and Practice of Pharmacy, 21$^{st}$ Edition, University of the Sciences in Philadelphia Ed. (2005). Such tablets can contain one or more known tableting excipients such as binders, fillers, disintegrants, glidants, lubricants, surfactants, plasticizers, anti-adherents, buffers, wetting agents, emulsifying agents, thickening agents, coloring agents, or combinations of any of the foregoing.

Binders may be included in the tablet core to hold the components of the core together. Examples of binders useful in the present disclosure include, for example, polyvinylpyrrolidone, hydroxypropyl cellulose, hydroxypropyl methylcellulose, methylcellulose, hydroxyethyl cellulose, sugars, dextran, cornstarch, and combinations of any of the foregoing. In certain embodiments, the binder is hydroxypropyl cellulose.

Fillers may be added to increase the bulk to make dosage forms. Examples of fillers useful in the present disclosure include dibasic calcium phosphate, dibasic calcium phosphate dihydrate, calcium sulfate, dicalcium phosphate, tricalcium phosphate, lactose, cellulose including microcrystalline cellulose, mannitol, sodium chloride, dry starch, pregelatinized starch, compressible sugar, mannitol, and combinations of any of the foregoing. In certain embodiments, a filler is lactose monohydrate. Fillers may be water insoluble, water soluble, or combinations thereof. Examples of useful water insoluble fillers include starch, dibasic calcium phosphate dihydrate, calcium sulfate, dicalcium phosphate, tricalcium phosphate, powdered cellulose, microcrystalline cellulose, and combinations of any of the foregoing. Examples of water-soluble fillers include water soluble sugars and sugar alcohols, such as lactose, glucose, fructose, sucrose, mannose, dextrose, galactose, the corresponding sugar alcohols and other sugar alcohols, such as mannitol, sorbitol, xylitol, and combinations of any of the foregoing. In certain embodiments wherein the filler is lactose, a tablet dosage form may comprise an amount of filler ranging from about 25 wt % to about 60 wt %, and in certain embodiments, from about 30 wt % to about 55 wt %.

Glidants may be included in the tablet core to reduce sticking effects during processing, film formation, and/or drying. Examples of useful glidants include talc, magnesium stearate, glycerol monostearate, colloidal silicon dioxide, precipitated silicon dioxide, fumed silicon dioxide, and combinations of any of the foregoing. In certain embodiments, a glidant is colloidal silicon dioxide. Tablet dosage forms may comprise less than about 3 wt % of a glidant, in certain embodiments, less than about 1 wt % of a glidant as a flow aid. In certain embodiments, a glidant is colloidal silicon dioxide.

Lubricants and anti-static agents may be included in a pharmaceutically acceptable coating to aid in processing. Examples of lubricants useful in coatings provided by the present disclosure include calcium stearate, glycerol behenate, glyceryl monostearate, magnesium stearate, mineral oil, polyethylene glycol, sodium stearyl fumarate, sodium lauryl sulfate, stearic acid, talc, vegetable oil, zinc stearate, and combinations of any of the foregoing. In certain embodiments, the lubricant is magnesium stearate. In certain embodiments, coatings may comprise an amount of lubricant ranging from about 0.5 wt % to about 3 wt % based on the total solids weight of the coating.

Disintegrants may be included in the tablet core to cause a tablet core to break apart, for example, by expansion of a disintegrants when exposed to water. Examples of useful disintegrants include water swellable substances such as croscarmellose sodium, sodium starch glycolate, cross-linked polyvinyl pyrrolidone, and combinations of any of the foregoing. In various embodiments, the disintegrants can be selected to be substantially free of carboxylic acid moieties.

2. Cores in the Form of Pellets/Powders/Granules

Cores can be in the form of pellets, powders, or granules. Pellets, powders, and granules are known in the art.

a. Pharmaceutical Pellet Making

Also provided is a method of making (N,N-Diethylcarbamoyl)methyl methyl (2E)but-2-ene-1,4-dioate-containing pharmaceutical pellets. Pharmaceutical pellets are conventionally made using either an extrusion/spheronization process, or a process called roto-pellitization. In both processes, a drug is mixed with a binder, commonly microcrystalline cellulose, and a solvent, typically water.

Thus, in the method, (N,N-Diethylcarbamoyl)methyl methyl (2E)but-2-ene-1,4-dioate is mixed with water and a binder to form a wet mass. The improvement disclosed herein is to add acetic acid to the wet mass and maintain the mass at a pH at or below 3.8 so that the acetic acid is predominantly in a non-ionizable state. In certain embodiments, the wet mass is buffered at a pH at or below 3.5. When acetic acid is added within the above mentioned pH ranges, one-dimensional crystal growth of (N,N-Diethylcarbamoyl)methyl methyl (2E)but-2-ene-1,4-dioate during the pellet drying step is reduced or eliminated, which prevents the pellets from agglomerating.

The method can be used in pellet making via either (i) an extrusion/spheronization process, or (ii) a roto-pelletization process as described in more detail below.

In a further alternative embodiment, the present disclosure is directed to a method of improving the yield of MHF-containing or MHF produg-containing pellets within a predetermined pellet size range during pellet manufacturing. The MHF or MHF prodrug is combined with water, an extrusion aid, and a binder, and optionally a disintegrant to form a wet mixture. The mixture is then passed through a screen or die (i.e., the mixture is extruded) to form an extrudate. The extrudate is then spheronized to form pellets. The addition of a binder and optionally a disintegrant to the mixture results in a significantly higher percent of pellets within a specific target size being formed. For example, extrusion dies for pharmaceutical pellet making typically have an opening ranging in size from 1 to 2 mm. The method described herein is effective at improving the yield of pellets within the size of the die opening+/−0.3 mm. An example of increasing the pellet size predictability is described in Example 11.

In various embodiments, the MHF prodrug is a prodrug described herein, such as (N,N-Diethylcarbamoyl)methyl methyl (2E)but-2-ene-1,4-dioate. In various further embodiments, the extrusion aid is microcrystalline cellulose, for example in amounts ranging from about 10 to 90 wt % of the wet mixture. In yet further embodiments the binder is hydroxypropyl cellulose, for example in amounts ranging from about 2 to 10 wt % of the wet mixture. In additional embodiments, the disintegrant is croscarmellose sodium, for example in amounts ranging from about 0.5 to 10 wt % of the wet mixture.

(i) Extrusion/Spheronization

In the extrusion/spheronization process, the MHF prodrug, binder, filler and water are generally mixed in either a high-shear granulator or a planetary mixer. Next, the wet mass (also referred to as a wet dough) is extruded to form cylindrical extrudates of a constant diameter (e.g., 0.6 to 1.2 mm). The wet mass is passed through the screen forming soft, pliable extrudates (similar to pasta) which break by their own weight into shorter units. The size of the final pellets (spheres) is principally determined by the hole diameter of the screen used in the extrusion step. Alternatively, the wet dough can be extruded through a die, i.e, a plate with holes. For example, in order to obtain spheres with a diameter of 1 mm, a 1 mm screen or die is used on the extruder, although spheres with a distribution of 0.8 to 1.2 mm may often be obtained. Next, the extrudates are charged to a spheronizer which includes a spinning friction plate. During the first contact of the cylindrical granules with the friction plate, the extrudates are cut into segments with a length ranging from 1 to 1.2 times their diameter. These segments then collide with the bowl wall and they are thrown back to the inside of the friction plate. Centrifugal force sends the material to the outside of the disc. The action of the material being moved causes the extrudate to be broken down into pieces of approximately equal length related to the diameter of the extrudate. These cylindrical segments are gradually rounded by the collisions with the bowl wall and the plate and each other. The ongoing action of particles colliding with the wall and being thrown back to the inside of the plate creates a "twisting rope movement" of product along the bowl wall. The continuous collision of the particles with the wall and with the friction plate gradually converts the cylindrical segments into spheres, provided that the extrudates are sufficiently pliable to allow the deformation without being destroyed or sticking together. When the particles have reached the desired level of sphericity, they are then discharged from the spheronizer. Finally, the wet pellets are collected and dried in a vertical fluid bed drier, or in some instances a tray hot with a flow of hot air over the pellets.

(ii) Roto-Pelletization

In the roto-pelletization process, the powdered mixture of MHF prodrug, filler and binder is introduced into the spheronizer and mixed in situ with an aqueous/water spray to form pellets that are rounded in a similar manner by contact with the spinning friction plate and the side walls of the spheronizer. A more detailed description of roto-pellitization is found in Vertommen et al., "Influence of five selected processing and formulation variables on the particle size, particle size distribution, and friability of pellets produced in a rotary processor", Drug Dev Ind Pharm. 1997; 23:39-46; Holm et al., "Pelletization by granulation in a roto-processor RP-2. Part 1. Effects of process and product variables on granule growth", Pharm Technol Eur. 1996; 8:22-36; and Kristensen et al., "Direct pelletization in a rotary processor controlled by torque measurements. I: Influence of process variables", Pharm Dev Technol. 2000; 5:247-256, the disclosures of which are incorporated herein by reference.

b. Powders and Granules

Alternatively, the formulation can be made as a powder or granule. Powders and granules can be made by conventional formulation methods understood in the art.

c. Drug Layering

In another variation, the formulation can be suspended or dissolved in a binder solution and sprayed onto an inert substrate such as nonpareil seeds. Such methods are performed as known in the art.

Compounds; MHF and MHF Prodrugs

In certain embodiments, the active ingredient in the dosage forms disclosed herein is methyl hydrogen fumarate or a pharmaceutically acceptable salt thereof.

Alternatively, the active ingredient in the dosage forms disclosed herein can be an MHF prodrug. One suitable MHF prodrug is dimethyl fumarate. Other suitable MHF prodrugs are the compounds of Formula (I):

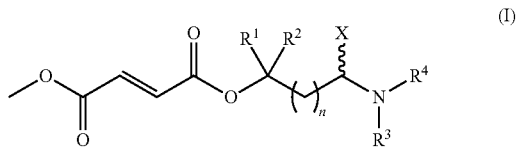

or a pharmaceutically acceptable salt thereof, wherein:

$R^1$ and $R^2$ are independently chosen from hydrogen, $C_{1-6}$ alkyl, and substituted $C_{1-6}$ alkyl;

$R^3$ and $R^4$ are independently chosen from hydrogen, $C_{1-6}$ alkyl, substituted $C_{1-6}$ alkyl, $C_{1-6}$ heteroalkyl, substituted $C_{1-6}$ heteroalkyl, $C_{3-11}$ cycloalkyl, substituted $C_{3-11}$ cycloalkyl, $C_{4-12}$ cycloalkylalkyl, substituted $C_{4-12}$ cycloalkylalkyl, $C_{7-12}$ arylalkyl, and substituted $C_{7-12}$ arylalkyl; or $R^3$ and $R^4$ together with the nitrogen to which they are bonded form a ring chosen from a $C_{4-10}$ heteroaryl, substituted $C_{4-10}$ heteroaryl, $C_{4-10}$ heterocycloalkyl, and substituted $C_{4-10}$ heterocycloalkyl;

n is an integer from 0 to 4; and

X is independently chosen from a single oxygen atom and a pair of hydrogen atoms;

wherein each substituent group is independently chosen from halogen, —OH, —CN, —CF$_3$, =O, —NO$_2$, benzyl, —C(O)NR$^{11}$$_2$, —R$^{11}$, —OR$^{11}$, —C(O)R$^{11}$, —COOR$^{11}$, and —NR$^{11}$$_2$ wherein each R$^{11}$ is independently chosen from hydrogen and $C_{1-4}$ alkyl;

and wherein when X is a single oxygen atom, the oxygen atom is connected to the carbon to which it is bonded by a double bond to form a carboxyl group and when X is a pair of hydrogen atoms, each hydrogen atom is connected to the carbon to which it is bonded to by single bond.

Compounds of Formula I are disclosed in (i) Gangakhedkar et al., U.S. Pat. No. 8,148,414; and (ii) Virsik et al. U.S. Ser. No. 61/653,375, filed May 30, 2012, the disclosures of which are incorporated herein by reference. The methods and schemes of synthesis disclosed in Gangakhedkar et al., U.S. Pat. No. 8,148,414 are incorporated herein by reference.

In other embodiments, the MHF prodrug is dimethyl fumarate.

In other embodiments, the MHF prodrug is a compound of Formula (II):

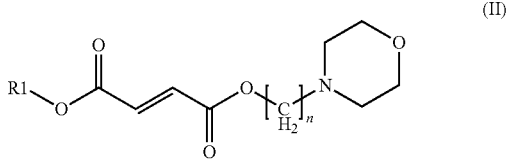

or a pharmaceutically acceptable salt thereof, wherein:
n is an integer from 2 to 6; and
$R^1$ is methyl.

Compounds of Formula (II) are disclosed in Cundy et al., U.S. Patent Application No. 61/595,835 filed Feb. 7, 2012, the disclosures of which are incorporated herein by reference.

Therapeutic Uses

The dosage forms disclosed herein may be administered to a patient suffering from any disease including a disorder, condition, or symptom for which MHF is known or hereafter discovered to be therapeutically effective. Indications for which MHF has been prescribed, and hence for which a dosage form disclosed herein is also expected to be effective, include psoriasis. Other indications for which the disclosed dosage forms may be therapeutically effective include multiple sclerosis, an inflammatory bowel disease, asthma, chronic obstructive pulmonary disease, and arthritis.

Methods of treating a disease in a patient provided by the present disclosure comprise administering to a patient in need of such treatment a dosage form disclosed herein. The dosage forms disclosed herein may provide therapeutic or prophylactic plasma and/or blood concentrations of MHF following administration to a patient.

The dosage forms disclosed herein may be administered in an amount and using a dosing schedule as appropriate for treatment of a particular disease. For example, daily doses of MHF or a MHF prodrug may range from about 0.01 mg/kg to about 50 mg/kg, from about 0.1 mg/kg to about 50 mg/kg, from about 1 mg/kg to about 50 mg/kg, and in certain embodiments, from about 5 mg/kg to about 25 mg/kg. In certain embodiments, the MHF or MHF prodrug may be administered at a dose over time from about 1 mg to about 5 g per day, from about 10 mg to about 4 g per day, and in certain embodiments from about 20 mg to about 2 g per day. An appropriate dose of MHF or a MHF prodrug may be determined based on several factors, including, for example, the body weight and/or condition of the patient being treated, the severity of the disease being treated, the incidence and/or severity of side effects, the manner of administration, and the judgment of the prescribing physician. Appropriate dose ranges may be determined by methods known to those skilled in the art.

MHF or a MHF prodrug may be assayed in vitro and in vivo for the desired therapeutic or prophylactic activity prior to use in humans. In vivo assays, for example using appropriate animal models, may also be used to determine whether administration of MHF or a MHF prodrug is therapeutically effective.

In certain embodiments, a therapeutically effective dose of MHF or a MHF prodrug may provide therapeutic benefit without causing substantial toxicity including adverse side effects. Toxicity of MHF or a MHF prodrug and/or metabolites thereof may be determined using standard pharmaceutical procedures and may be ascertained by those skilled in the art. The dose ratio between toxic and therapeutic effect is the therapeutic index. A dose of MHF or a MHF prodrug may be within a range capable of establishing and maintaining a therapeutically effective circulating plasma and/or blood concentration of MHF or a MHF prodrug that exhibits little or no toxicity.

The dosage forms disclosed herein may be used to treat diseases, disorders, conditions, and symptoms of any of the foregoing for which MHF is known to provide or is later found to provide therapeutic benefit. MHF is known to be effective in treating psoriasis, multiple sclerosis, an inflammatory bowel disease, asthma, chronic obstructive pulmonary disease, and arthritis. Hence, the dosage forms disclosed herein may be used to treat any of the foregoing diseases and disorders. The underlying etiology of any of the foregoing diseases being treated may have a multiplicity of origins. Further, in certain embodiments, a therapeutically effective amount of MHF and/or a MHF prodrug may be administered to a patient, such as a human, as a preventative measure against various diseases or disorders. Thus, a therapeutically effective amount of MHF or a MHF prodrug may be administered as a preventative measure to a patient having a predisposition for and/or history of immunological, autoimmune, and/or inflammatory diseases including psoriasis, asthma and chronic obstructive pulmonary diseases, cardiac insufficiency including left ventricular insufficiency, myocardial infarction and angina pectoris, mitochondrial and neurodegenerative diseases such as Parkinson's disease, Alzheimer's disease, Huntington's disease, retinopathia pigmentosa and mitochondrial encephalomyopathy, transplantation rejection, autoimmune diseases including multiple sclerosis, ischemia and reperfusion injury, AGE-induced genome damage, inflammatory bowel diseases such as Crohn's disease and ulcerative colitis; and NF-κB mediated diseases.

Psoriasis

Psoriasis is characterized by hyperkeratosis and thickening of the epidermis as well as by increased vascularity and infiltration of inflammatory cells in the dermis. Psoriasis vulgaris manifests as silvery, scaly, erythematous plaques on typically the scalp, elbows, knees, and buttocks. Guttate psoriasis occurs as tear-drop size lesions.

Fumaric acid esters are recognized for the treatment of psoriasis and dimethyl fumarate is approved for the systemic treatment of psoriasis in Germany (Mrowietz and Asadullah, Trends Mol Med 2005, 11(1), 43-48; and Mrowietz et al., Br J Dermatology 1999, 141, 424-429).

Efficacy of MHF or a MHF prodrug for treating psoriasis can be determined using animal models and in clinical trials.

Inflammatory Arthritis

Inflammatory arthritis includes diseases such as rheumatoid arthritis, juvenile rheumatoid arthritis (juvenile idiopathic arthritis), psoriatic arthritis, and ankylosing spondylitis, each of which produce joint inflammation. The pathogenesis of immune-mediated inflammatory diseases including inflammatory arthritis is believed to involve TNF and NK-κB signaling pathways (Tracey et al., Pharmacology & Therapeutics 2008, 117, 244-279). DMF has been shown to inhibit TNF and inflammatory diseases including inflammatory arthritis, which are believed to involve TNF and NK-κB signaling and therefore may be useful in treating inflammatory arthritis (Lowewe et al., J Immunology 2002, 168, 4781-4787).

The efficacy of MHF or a MHF prodrug for treating inflammatory arthritis can be determined using animal models and in clinical trials.

Multiple Sclerosis

Multiple sclerosis (MS) is an inflammatory autoimmune disease of the central nervous system caused by an autoimmune attack against the isolating axonal myelin sheets of the central nervous system. Demyelination leads to the breakdown of conduction and to severe disease with destruction of local axons and irreversible neuronal cell death. The symptoms of MS are highly varied with each individual patient exhibiting a particular pattern of motor, sensible, and sensory disturbances. MS is typified pathologically by multiple inflammatory foci, plaques of demyelination, gliosis, and axonal pathology within the brain and spinal cord, all of which contribute to the clinical manifestations of neurological disability (see e.g., Wingerchuk, Lab Invest 2001, 81, 263-281; and Virley, NeuroRx 2005, 2(4), 638-649). Although the causal events that precipitate MS are not fully understood, evidence implicates an autoimmune etiology together with environmental factors, as well as specific genetic predispositions. Functional impairment, disability, and handicap are expressed as paralysis, sensory and octintive disturbances, spasticity, tremor, a lack of coordination, and visual impairment, which impact on the quality of life of the individual. The clinical course of MS can vary from individual to individual, but invariably the disease can be categorized in three forms: relapsing-remitting, secondary progressive, and primary progressive.

Studies support the efficacy of FAEs for treating MS and are undergoing phase II clinical testing (Schimrigk et al., Eur J Neurology 2006, 13, 604-610; and Wakkee and Thio, Current Opinion Investigational Drugs 2007, 8(11), 955-962).

Assessment of MS treatment efficacy in clinical trials can be accomplished using tools such as the Expanded Disability Status Scale and the MS Functional as well as magnetic resonance imaging lesion load, biomarkers, and self-reported quality of life. Animal models of MS shown to be useful to identify and validate potential therapeutics include experimental autoimmune/allergic encephalomyelitis (EAE) rodent models that simulate the clinical and pathological manifestations of MS and nonhuman primate EAE models.

Inflammatory Bowel Disease (Crohn's Disease, Ulcerative Colitis)

Inflammatory bowel disease (IBD) is a group of inflammatory conditions of the large intestine and in some cases, the small intestine that includes Crohn's disease and ulcerative colitis. Crohn's disease, which is characterized by areas of inflammation with areas of normal lining in between, can affect any part of the gastrointestinal tract from the mouth to the anus. The main gastrointestinal symptoms are abdominal pain, diarrhea, constipation, vomiting, weight loss, and/or weight gain. Crohn's disease can also cause skin rashes, arthritis, and inflammation of the eye. Ulcerative colitis is characterized by ulcers or open sores in the large intestine or colon. The main symptom of ulcerative colitis is typically constant diarrhea with mixed blood of gradual onset. Other types of intestinal bowel disease include collagenous colitis, lymphocytic colitis, ischaemic colitis, diversion colitis, Behcet's colitis, and indeterminate colitis.

FAEs are inhibitors of NF-κB activation and therefore may be useful in treating inflammatory diseases such as Crohn's disease and ulcerative colitis (Atreya et al., J Intern Med 2008, 263(6), 59106).

The efficacy of MHF or a MHF prodrug for treating inflammatory bowel disease can be evaluated using animal models and in clinical trials. Useful animal models of inflammatory bowel disease are known.

Asthma

Asthma is reversible airway obstruction in which the airway occasionally constricts, becomes inflamed, and is lined with an excessive amount of mucus. Symptoms of asthma include dyspnea, wheezing, chest tightness, and cough. Asthma episodes may be induced by airborne allergens, food allergies, medications, inhaled irritants, physical exercise, respiratory infection, psychological stress, hormonal changes, cold weather, or other factors.

As an inhibitor of NF-κB activation and as shown in animal studies (Joshi et al., US 2007/0027076) FAEs may be useful in treating pulmonary diseases such as asthma and chronic obstructive pulmonary disorder.

The efficacy of MHF or a MHF prodrug for treating asthma can be assessed using animal models and in clinical trials.

Chronic Obstructive Pulmonary Disease

Chronic obstructive pulmonary disease (COPD), also known as chronic obstructive airway disease, is a group of diseases characterized by the pathological limitation of airflow in the airway that is not fully reversible, and includes conditions such as chronic bronchitis, emphysema, as well as other lung disorders such as asbestosis, pneumoconiosis, and pulmonary neoplasms (see, e.g., Barnes, Pharmacological Reviews 2004, 56(4), 515-548). The airflow limitation is usually progressive and associated with an abnormal inflammatory response of the lungs to noxious particles and gases. COPD is characterized by a shortness of breath that can last for months or years, possibly accompanied by wheezing, and a persistent cough with sputum production. COPD is most often caused by tobacco smoking, although it can also be caused by other airborne irritants such as coal dust, asbestos, urban pollution, or solvents. COPD encompasses chronic obstructive bronchiolitis with fibrosis and obstruction of small airways, and emphysema with enlargement of airspaces and destruction of lung parenchyma, loss of lung elasticity, and closure of small airways.

The efficacy of administering MHF or a MHF prodrug for treating chronic obstructive pulmonary disease may be assessed using animal models of chronic obstructive pulmonary disease and in clinical studies. For example, murine models of chronic obstructive pulmonary disease are known.

Neurodegenerative Disorders

Neurodegenerative diseases such as Parkinson's disease, Alzheimer's disease, Huntington's disease and amyoptrophic lateral sclerosis are characterized by progressive dysfunction and neuronal death. NF-κB inhibition has been proposed as a therapeutic target for neurodegenerative diseases (Camandola and Mattson, Expert Opin Ther Targets 2007, 11(2), 123-32).

Parkinson's Disease

Parkinson's disease is a slowly progressive degenerative disorder of the nervous system characterized by tremor when muscles are at rest (resting tremor), slowness of voluntary movements, and increased muscle tone (rigidity).

In Parkinson's disease, nerve cells in the basal ganglia, e.g., substantia nigra, degenerate, and thereby reduce the production of dopamine and the number of connections between nerve cells in the basal ganglia. As a result, the basal ganglia are unable to properly control smooth muscle movements and coordinate changes in posture as normal, leading to tremor, incoordination, and slowed, reduced movement (bradykinesia) (Blandini, et al., Mol. Neurobiol. 1996, 12, 73-94).

The efficacy of MHF or a MHF prodrug for treating Parkinson's disease may be assessed using animal and human models of Parkinson's disease and in clinical studies.

Alzheimer's Disease

Alzheimer's disease is a progressive loss of mental function characterized by degeneration of brain tissue, including loss of nerve cells and the development of senile plaques and neurofibrillary tangles. In Alzheimer's disease, parts of the brain degenerate, destroying nerve cells and reducing the responsiveness of the maintaining neurons to neurotransmitters. Abnormalities in brain tissue consist of senile or neuritic plaques, e.g., clumps of dead nerve cells containing an abnormal, insoluble protein called amyloid, and neurofibrillary tangles, twisted strands of insoluble proteins in the nerve cell.

The efficacy of MHF or a MHF prodrug for treating Alzheimer's disease may be assessed using animal and human models of Alzheimer's disease and in clinical studies.

Huntington's Disease

Huntington's disease is an autosomal dominant neurodegenerative disorder in which specific cell death occurs in the neostriatum and cortex (Martin, N Engl J Med 1999, 340, 1970-80). Onset usually occurs during the fourth or fifth decade of life, with a mean survival at age of onset of 14 to 20 years. Huntington's disease is universally fatal, and there is no effective treatment. Symptoms include a characteristic movement disorder (Huntington's chorea), cognitive dysfunction, and psychiatric symptoms. The disease is caused by a mutation encoding an abnormal expansion of CAG-encoded polyglutamine repeats in the protein, huntingtin.

The efficacy of MHF or a MHF prodrug for treating Huntington's disease may be assessed using animal and human models of Huntington's disease and in clinical studies.

Amyotrophic Lateral Sclerosis

Amyotrophic lateral sclerosis (ALS) is a progressive neurodegenerative disorder characterized by the progressive and specific loss of motor neurons in the brain, brain stem, and spinal cord (Rowland and Schneider, N Engl J Med 2001, 344, 1688-1700). ALS begins with weakness, often in the hands and less frequently in the feet that generally progresses up an arm or leg. Over time, weakness increases and spasticity develops characterized by muscle twitching and tightening, followed by muscle spasms and possibly tremors. The average age of onset is 55 years, and the average life expectancy after the clinical onset is 4 years. The only recognized treatment for ALS is riluzole, which can extend survival by only about three months.

The efficacy MHF or a MHF prodrug for treating ALS may be assessed using animal and human models of ALS and in clinical studies.

Other Diseases

Other diseases and conditions for which MHF or a MHF prodrug such as DMF or a compound of Formulae (I) or (II) can be useful in treating include acute disseminated encephalomyelitis, Addison's disease, adrenal leukodystrophy, Alexanders Disease, alopecia areata, Alper's Disease, ankylosing spondylitis, antiphospholipid antibody syndrome, autoimmune hemolytic anemia, autoimmune hepatitis, autoimmune inner ear disease, autoimmune carditis, balo concentric sclerosis, bullous pemphigoid, Behcet's disease, Canavan disease, celiac disease, central nervous system vasculitis, Chagas disease, Charcott-Marie-Tooth Disease, childhood ataxia with central nervous system hypomyelination, dermatomyositis, diabetes mellitus type I, eczema, endometriosis, Goodpasture's syndrome, granuloma annulare, Graves' disease, Guillain-Barre syndrome, Hashimoto's disease, hepatitis C viral infection, herpes simplex viral infection, hidradenitis suppurativea, human immunodeficiency viral infection, Kawasaki disease, Krabbe Disease, IgA neuropathy, idiopathic thrombocytopenic purpura, interstitial cystitis, lupus, lupus erythematosus, mixed connective tissue disease, monomelic myotrophy, morphea, myasthenia gravis, narcolepsy, neurodegeneration with brain iron accumulation, neuromyelitis optica, neuromyotonia, neurosarcoidosis, optic neuritis, pareneoplastic syndromes, Pelizaeus-Merzbacher disease, pemphigus vulgaris, pernicious anaemia, primary biliary cirrhosis, primary lateral sclerosis, psoriatic arthritis, polymyositis, progressive supranuclear palsy, rheumatica, rheumatoid arthritis, sarcoidosis, Schilders Disease, schizophrena, scleroderma, Sjogren's syndrome, stiff person syndrome, subacute necrotizing myelopathy, susac syndrome, temporal arteritis, transverse myelitis, tumors, vasculitis, vitiligo, Wegener's granulomatosis and Zellweger's syndrome.

Dosing

The dosage forms disclosed herein, and their use for therapeutic treatment, are not limited to any particular oral dosing regimen as long as the dosing regimen achieves therapeutic blood plasma concentration levels and AUC levels. MHF or a MHF prodrug may be administered at dosage levels of about 0.001 mg/kg to about 50 mg/kg, from about 0.01 mg/kg to about 25 mg/kg, or from about 0.1 mg/kg to about 10 mg/kg of subject body weight per day, one, two, three, four or more times a day, to obtain the desired concentrations and AUC for MHF in the blood plasma.

For the treatment of multiple sclerosis and/or psoriasis, MHF concentrations in blood plasma of at least 0.5 µg/ml during the course of dosing is desired. In other embodiments, MHF concentrations in blood plasma of at least 0.7 µg/ml during the course of dosing is desired. In other embodiments, MHF concentrations in blood plasma of at least 1.2 µg/ml during the course of dosing is desired.

Similarly, for the treatment of multiple sclerosis and/or psoriasis, an area under a concentration of MHF in blood plasma versus time curve (AUC) of at least 4.0 µg·hr/ml over 24 hours of dosing is desired. In other embodiments, an area under a concentration of MHF in blood plasma versus time curve (AUC) of at least 4.8 µg·hr/ml over 24 hours of dosing is desired. In other embodiments, an area under a concentration of MHF in blood plasma versus time curve (AUC) of at least 6.0 µg·hr/ml over 24 hours of dosing is desired. In other embodiments, an area under a concentration of MHF in blood plasma versus time curve (AUC) of at least 7.0 µg·hr/ml over 24 hours of dosing is desired. In other embodiments, an area under a concentration of MHF in blood plasma versus time curve (AUC) of at least 9.0 µg·hr/ml over 24 hours of dosing is desired. In other embodiments, an area under a concentration of MHF in blood plasma versus time curve (AUC) of at least 10.5 µg·hr/ml over 24 hours of dosing is desired. In still other embodiments, an area under a concentration of MHF in blood plasma versus time curve (AUC) of at least 12.0 μg·hr/ml over 24 hours of dosing is desired.

The amount of MHF or a MHF prodrug that will be effective in the treatment of a disease in a patient will depend, in part, on the nature of the condition and can be determined by standard clinical techniques known in the art. In addition, in vitro or in vivo assays may be employed to help identify optimal dosage ranges. A therapeutically effective amount of MHF or a MHF prodrug to be administered may also depend on, among other factors, the subject being treated, the weight of the subject, the severity of the disease, the manner of administration, and the judgment of the prescribing physician.

For systemic administration, a therapeutically effective dose may be estimated initially from in vitro assays. For example, a dose may be formulated in animal models to achieve a beneficial circulating composition concentration range. Initial doses may also be estimated from in vivo data, e.g., animal models, using techniques that are known in the art. Such information may be used to more accurately determine useful doses in humans. One having ordinary skill in the art may optimize administration to humans based on animal data.

A dose may be administered in a single dosage form or in multiple dosage forms. When multiple dosage forms are used the amount of compound contained within each dosage form may be the same or different. The amount of MHF or a MHF prodrug contained in a dose may depend on whether the disease in a patient is effectively treated by acute, chronic, or a combination of acute and chronic administration.

In certain embodiments an administered dose is less than a toxic dose. Toxicity of the compositions described herein may be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. In certain embodiments, a MHF prodrug may exhibit a high therapeutic index. The data obtained from these cell culture assays and animal studies may be used in formulating a dosage range that is not toxic for use in humans. A dose of MHF or a MHF prodrug provided by the present disclosure may be within a range of circulating concentrations in for example the blood, plasma, or central nervous system, that include the effective dose and that exhibits little or no toxicity. A dose may vary within this range depending upon the dosage form employed. In certain embodiments, an escalating dose may be administered.

EXAMPLES

The following examples illustrate various aspects of the disclosure. It will be apparent to those skilled in the art that many modifications, both to materials and methods, may be practiced without departing from the scope of the disclosure.

Example 1

Delayed release tablets containing (N,N-Diethylcarbamoyl)methyl methyl (2E)but-2-ene-1,4-dioate were made having the ingredients shown in Table 1:

TABLE 1

| Component | Manufacturer | Role | Quantity (mg/tablet) | Quantity (% w/w) |
|---|---|---|---|---|
| (N,N-Diethylcarbamoyl)methyl methyl (2E)but-2-ene-1,4-dioate | XenoPort (Santa Clara, CA) | Drug substance | 200.00 | 78.38 |
| Hydroxypropyl Cellulose | Ashland (Hopewell, VA) | Binder | 6.19 | 2.42 |
| Lactose Monohydrate | Foremost (Rothschild, WI) | Filler | 38.28 | 15.00 |
| Croscarmellose Sodium | FMC BioPolymer (Philadelphia, PA) | Disintegrant | 7.66 | 3.00 |
| Silicon Dioxide | Cabot (Tuscola, IL) | Glidant | 0.51 | 0.20 |
| Magnesium Stearate | Mallinckrodt (St. Louis, MO) | Lubricant | 2.55 | 1.00 |
| | | Total Core | 255.19 | 100.00 |
| Opadry 03O19184 | Colorcon (West Point, PA) | Barrier coat | 6.80 | 2.66 |
| | | Total Barrier Coating | 6.80 | 2.66 |
| Methacrylic Acid Co-polymer Dispersion | Evonik Industries (Essen, Germany) | Enteric polymer | 21.10 | 8.27 |
| Triethyl Citrate | Vertellus (Greensboro, NC) | Plasticizer | 1.10 | 0.43 |
| PlasACRYL ™ T20 | Emerson Resources (Norristown, PA) | Anti-tacking agent | 2.10 | 0.82 |
| | | Total Enteric Coating | 24.30 | 9.52 |
| | | Total Tablet | 286.29 | 112.19 |

The tablets were made according to the following steps. The core tablets were prepared using a wet granulation process. The granulation was performed in two batches at 463.9 g per batch. The (N,N-Diethylcarbamoyl)methyl methyl (2E)but-2-ene-1,4-dioate and hydroxypropyl cellulose were passed through a conical mill with a 610 micron round holed screen. The (N,N-Diethylcarbamoyl)methyl methyl (2E)but-2-ene-1,4-dioate and hydroxypropyl cellulose were then combined in a Key KG-5 granulator bowl and mixed with water addition for approximately 9 minutes. The wet granules were dried in a Glatt GPCG-1 fluid bed dryer at 40° C. The two portions of dried granules were combined and blended with the silicon dioxide in an 8 quart (7.6 liter) V-blender for 5 minutes and then sized by passing through a conical mill with an approximately 1300 micron grater type screen. The milled granules were blended with the croscarmellose sodium and lactose monohydrate for 10 minutes in an 8 quart (7.6 l) V-blender. The magnesium stearate was passed through a 600 micron mesh screen and blended with the additional core materials in the V-blender for 5 minutes. Core tablets (254.87 mg) were compressed using a GlobePharma Minipress II rotary tablet press with 11/32 inch (8.7 mm) round concave tooling. The core tablets had a final mean hardness of approximately 15.5 kp. An aqueous suspension was prepared by mixing with an impeller 68.85 g Opadry 03O19184 with 792.0 g of purified water. The water contained in the suspension is removed during the film coating process and therefore not included in the final formulation in Table 1. The tablets were coated with the aqueous suspension in an O'Hara Technologies Labcoat M coater with a 12" (30.5 cm) diameter perforated pan until the desired weight gain of barrier coat was achieved. The coating process occurred at an inlet temperature of approximately 52° C. and an outlet temperature of 37° C. After coating, the tablets were dried for 2 hours at 40° C. An aqueous suspension was prepared by mixing with an impeller 578.7 g methacrylic acid copolymer dispersion, 9.0 g triethyl citrate, 86.5 g PlasACRYL™ T20 with 325.8 g water. The water contained in (i) the methacrylic acid copolymer dispersion and (ii) the PlasACRYL™ T20 is removed during the film coating process and therefore not included in the final formulation in Table 1. The tablets were coated with the aqueous suspension in an O'Hara Technologies Labcoat M coater with a 12" (30.5 cm) diameter perforated pan until the desired weight gain of enteric film was achieved. The coating process occurred at an inlet temperature of approximately 40° C. and an outlet temperature of 30° C. After coating, the tablets were dried for 2 hours at 40° C.

Example 2

Delayed sustained release tablets containing (N,N-Diethylcarbamoyl)methyl methyl (2E)but-2-ene-1,4-dioate were made having the ingredients shown in Table 2:

TABLE 2

| Component | Manufacturer | Role | Quantity (mg/tablet) | Quantity (% w/w) |
|---|---|---|---|---|
| (N,N-Diethylcarbamoyl)methyl methyl (2E)but-2-ene-1,4-dioate | XenoPort (Santa Clara, CA) | Drug substance | 200.00 | 66.74 |
| Hydroxypropyl Cellulose | Ashland (Hopewell, VA) | Binder | 6.19 | 2.06 |
| Lactose Monohydrate | Foremost (Rothschild, WI) | Filler | 44.95 | 15.00 |
| Hypromellose 2208 | Dow Chemical (Midland, MI) | Sustained release agent | 44.95 | 15.00 |
| Silicon Dioxide | Cabot (Tuscola, IL) | Glidant | 0.60 | 0.20 |
| Magnesium Stearate | Mallinckrodt (St. Louis, MO) | Lubricant | 3.00 | 1.00 |
| | | Total Core | 299.69 | 100.00 |
| Opadry 03O19184 | Colorcon (West Point, PA) | Barrier coat | 7.13 | 2.38 |
| | | Total Barrier Coating | 7.13 | 2.38 |
| Methacrylic Acid Co-polymer Dispersion | Evonik Industries (Essen, Germany) | Enteric polymer | 24.20 | 8.08 |
| Triethyl Citrate | Vertellus (Greensboro, NC) | Plasticizer | 1.25 | 0.42 |
| PlasACRYL™ T20 | Emerson Resources (Norristown, PA) | Anti-tacking agent | 2.41 | 0.80 |
| | | Total Enteric Coating | 27.87 | 9.30 |
| | | Total Tablet | 334.69 | 111.68 |

The tablets were made according to the following steps. The core tablets were prepared using a wet granulation process. The granulation was performed in two batches at 456 g per batch. The (N,N-Diethylcarbamoyl)methyl methyl (2E)but-2-ene-1,4-dioate and hydroxypropyl cellulose were passed through a conical mill with a 610 micron round holed screen. The (N,N-Diethylcarbamoyl)methyl methyl (2E)but-2-ene-1,4-dioate and hydroxypropyl cellulose were then combined in a Key KG-5 granulator bowl and mixed with water addition for approximately 7 minutes. The wet granules were dried in a Glatt GPCG-1 fluid bed dryer at 40° C. The two portions of dried granules were sized by passing through a conical mill with an approximately 1300 micron grater type screen. The milled granules were blended with the hypromellose 2208, silicon dioxide, and lactose monohydrate for 10 minutes in an 8 quart (7.6 l) V-blender. This blend was passed through an 850 micron mesh screen. The magnesium stearate was passed through a 600 micron mesh screen and blended with the additional core materials in the V-blender for 5 minutes. Core tablets (299.69 mg) were compressed using a GlobePharma Minipress II rotary tablet press with 8.6 mm round concave tooling. The core tablets had a final mean hardness of approximately 12 kp. An aqueous suspension was prepared by mixing with an impeller 63.8 g Opadry 03019184 with 770.7 g of purified water. The water contained in the suspension is removed during the film coating process and therefore not included in the final formulation in Table 2. The tablets were coated with the aqueous suspension in an O'Hara Technologies Labcoat M coater with a 12" (30.5 cm) diameter perforated pan until the desired weight gain of barrier coat was achieved. The coating process occurred at an inlet temperature of approximately 52° C. and an outlet temperature of 36° C. After coating, the tablets were dried for 2 hours at 40° C. An aqueous suspension was prepared by mixing with an impeller 405.1 g methacrylic acid copolymer dispersion, 6.3 g triethyl citrate, 60.6 g PlasACRYL™ T20 with 228.1 g water. The water contained in the methacrylic acid copolymer dispersion and the PlasACRYL™ T20 is removed during the film coating process and therefore not included in the final formulation in Table 1. The tablets were coated with the aqueous suspension in the O'Hara Technologies Labcoat M coater until the desired weight gain of enteric film was achieved. The coating process occurred at an inlet temperature of approximately 40° C. and an outlet temperature of 30° C. After coating, the tablets were dried for 2 hours at 40° C.

Example 3

A two-stage dissolution method was used to determine the in vitro dissolution profile of dosage forms prepared according to Examples 1 and 2. The 2-stage dissolution test was used to better approximate the pH conditions experienced by a dosage form after swallowing by a patient, i.e., low pH of the stomach followed by near neutral pH of the intestines. The dosage forms were first placed into a dissolution vessel (USP, Type I, basket) containing 750 mL of 0.1 N hydrochloric acid (pH 1.2). After 2 hours, 250 mL of 200 mM tribasic sodium phosphate was added to the vessel resulting in a pH adjustment from 1.2 to 6.8. The dissolution medium was kept at 37° C. and was agitated at 100 rpm.

For the Example 1 dosage forms, samples of the dissolution medium were withdrawn after 1 and 2 hours in the low pH stage, and at 0.25, 0.5, 0.75, and 1 hours following buffer addition. For the Example 2 dosage forms, samples of the dissolution medium were withdrawn after 1 and 2 hours in the low pH stage, and at 0.5, 2, 4, 7, 10, and 14 hours following buffer addition. The released amount of (N,N-Diethylcarbamoyl)methyl methyl (2E)but-2-ene-1,4-dioate in the samples was determined by reverse phase HPLC using a C18 column and a 7 minute gradient method according to Table 3 where Mobile Phase A is water/0.1% $H_3PO_4$ and Mobile Phase B is water/acetonitrile/$H_3PO_4$ (10/90/0.1 by volume) with UV detection at 210 nm.

TABLE 3

| Time (minute) | % Mobile Phase A | % Mobile Phase B |
| --- | --- | --- |
| 0 | 85 | 15 |
| 5 | 35 | 65 |
| 5.5 | 85 | 15 |
| 7 | 85 | 15 |

As shown in FIG. 1, for dosage forms prepared according to Example 1, drug release is delayed for approximately 2 hours, followed with near immediate release with >90% released between 2 and 3 hours.

Figure 2:
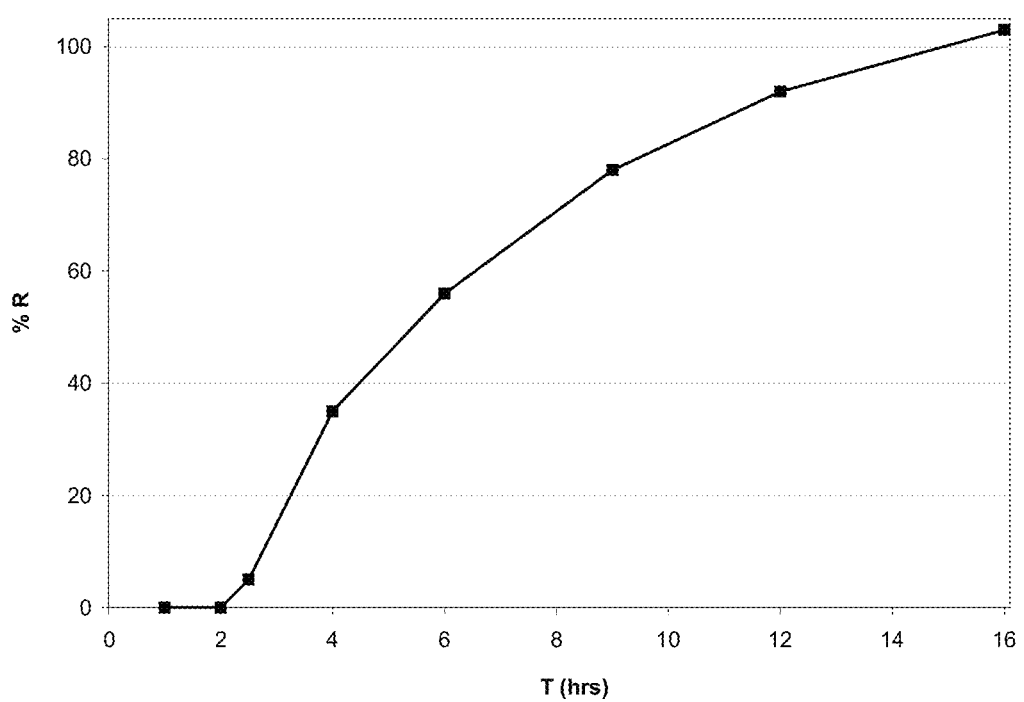
FIG. 2 is a graph showing the in vitro MHF prodrug release profile (percent MHF prodrug released over time) for the dosage forms of Example 2, tested in accordance with Example 3.

As shown in FIG. 2, for dosage forms prepared according to Example 2, drug release is delayed for approximately 2 hours, followed by sustained release reaching >90% at 12 hours.

Comparative Example 1

No Barrier Coating

Delayed sustained release tablets having no barrier coating were manufactured using substantially the same core components as the tablets of Example 2. After tablet core compression, no barrier layer coating was applied. Instead, the tablet cores were directly coated with an enteric coating as follows. An aqueous enteric coating suspension was prepared by mixing with an impeller 289.4 g methacrylic acid copolymer dispersion, 4.5 g triethyl citrate, 43.25 g PlasACRYL™ T20 with 162.9 g water. The tablet cores were coated with the aqueous suspension in the O'Hara Technologies Labcoat M coater to achieve a enteric coating weight of 27.9 mg per tablet. The coating process occurred at an inlet temperature of approximately 42° C. and an outlet temperature of 31° C. After coating, the tablets were dried for 2 hours at 40° C.

Example 4

Figure 3:
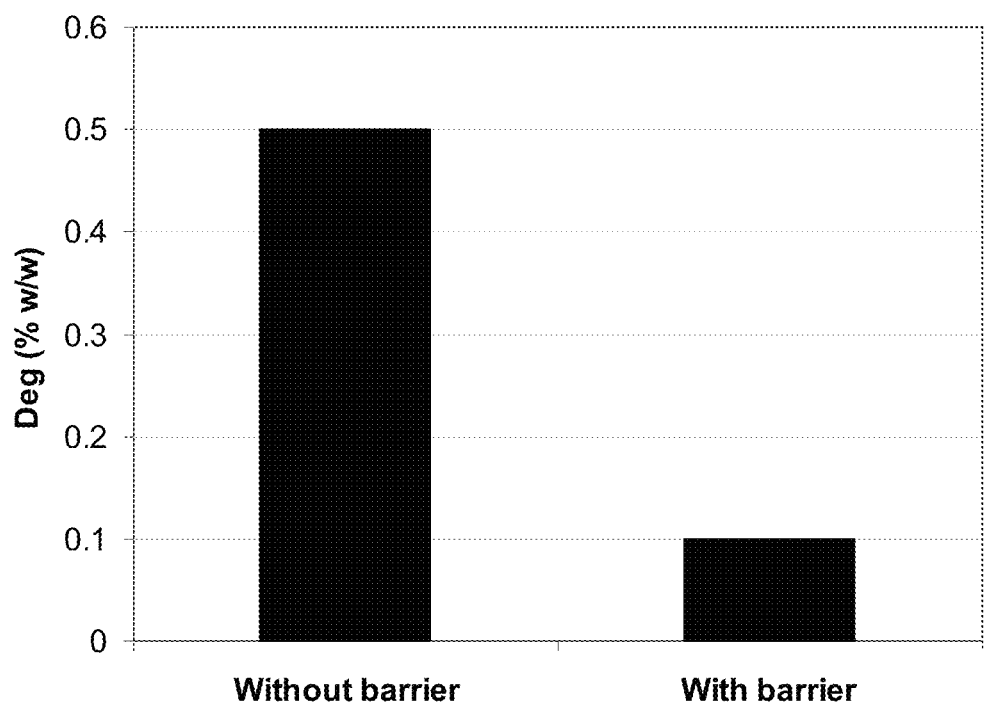
FIG. 3 is a graph showing the percent of MHF prodrug degradation over 3 months for the dosage forms of Example 2 and Comparative Example 1, tested in accordance with Example 4.

Delayed sustained release tablets manufactured as in Example 2 (with a barrier coating) and tablets manufactured as in Comparative Example 1 (with no barrier coating) were each packaged for stability testing. The packaging configuration was fifteen tablets in a 0.025 inch (0.6 mm) thick, 30 cm³ HDPE bottle with child-resistant screw cap and foil induction seal, containing a 1 g silica gel canister. The tablets were stored at 40° C. and 75% relative humidity and tested for assay/impurities at 3 months. The total degradants detected in the tablets at three months are shown in FIG. 3.

Example 5

Delayed release tablets containing (N,N-Diethylcarbamoyl)methyl methyl (2E)but-2-ene-1,4-dioate are made having the ingredients shown in Tables 4A and 4B:

TABLE 4A

| Component | Manufacturer | Role | Quantity (mg/tablet) | Quantity (% w/w of core) |
|---|---|---|---|---|
| (N,N-Diethylcarbamoyl)methyl methyl (2E)but-2-ene-1,4-dioate | XenoPort (Santa Clara, CA) | Drug substance | 200.00 | 78.47 |
| Hydroxypropyl Cellulose | Aqualon (Hopewell, VA) | Binder | 6.19 | 2.43 |
| Lactose Monohydrate | Foremost (Rothschild, WI) | Filler | 38.23 | 15.00 |
| Croscarmellose Sodium | FMC BioPolymer (Philadelphia, PA) | Disintegrant | 7.65 | 3.00 |
| Silicon Dioxide | Cabot (Tuscola, IL) | Glidant | 0.25 | 0.10 |
| Magnesium Stearate | Mallinckrodt (St. Louis, MO) | Lubricant | 2.55 | 1.00 |
| | | Total Core | 254.87 | 100.00 |
| Opadry 03O19184 | Colorcon (West Point, PA) | Barrier coat | 6.78 | 2.66 |
| | | Total Barrier Coating | 6.78 | 2.66 |
| Methacrylic Acid Co-polymer Dispersion | Evonik Industries (Essen, Germany) | Enteric polymer | 20.03 | 7.86 |
| Triethyl Citrate | Moreflex (Greensboro, NC) | Plasticizer | 1.04 | 0.41 |
| PlasACRYL ™ T20 | Emerson Resources (Norristown, PA) | Anti-tacking agent | 2.00 | 0.78 |
| | | Total Enteric Coating | 23.07 | 9.05 |
| | | Total Tablet | 284.72 | 111.71 |

TABLE 4B

| Component | Manufacturer | Role | Quantity (mg/tablet) | Quantity (% w/w of core) |
|---|---|---|---|---|
| (N,N-Diethylcarbamoyl)methyl methyl (2E)but-2-ene-1,4-dioate | Cambridge Major (Germantown, WI) | Drug substance | 200.00 | 78.38 |
| Hydroxypropyl Cellulose | Aqualon (Hopewell, VA) | Binder | 6.19 | 2.42 |
| Lactose Monohydrate | Foremost (Rothschild, WI) | Filler | 38.28 | 15.00 |
| Croscarmellose Sodium | FMC BioPolymer (Philadelphia, PA) | Disintegrant | 7.66 | 3.00 |
| Silicon Dioxide | Cabot (Tuscola, IL) | Glidant | 0.51 | 0.20 |
| Magnesium Stearate | Mallinckrodt (St. Louis, MO) | Lubricant | 2.55 | 1.00 |
| | | Total Core | 255.19 | 100.00 |
| Opadry 03O19184 | Colorcon (West Point, PA) | Barrier coat | 6.79 | 2.66 |
| | | Total Barrier Coating | 6.79 | 2.66 |
| Methacrylic Acid Co-polymer Dispersion | Evonik Industries (Essen, Germany) | Enteric polymer | 17.30 | 6.78 |
| Triethyl Citrate | Moreflex (Greensboro, NC) | Plasticizer | 0.89 | 0.35 |
| PlasACRYL ™ T20 | Emerson Resources (Norristown, PA) | Anti-tacking agent | 1.74 | 0.68 |
| | | Total Enteric Coating | 19.93 | 7.81 |
| | | Total Tablet | 281.91 | 110.47 |

The cores of the Table 4A tablets are made according to the following steps. The core tablets are prepared using a wet granulation process. The granulation batch size is 680 g. The (N,N-Diethylcarbamoyl)methyl methyl (2E)but-2-ene-1,4-dioate is passed through a Quadro Comil U5 with an 813 micron screen at 2000 rpm. Hydroxypropyl cellulose is passed through a 600 micron mesh screen. The (N,N-Diethylcarbamoyl)methyl methyl (2E)but-2-ene-1,4-dioate and hydroxypropyl cellulose are granulated with purified water using a Diosna P1/6 equipped with a 4 L bowl. The wet granules are screened through an 1180 micron mesh screen and are dried on trays in an oven at 30° C. for 6 hours. The core blend batch size is 15.0 g. The dried granules, lactose monohydrate, croscarmellose sodium, and the silicon dioxide are combined in a glass jar and are blended in a Turbula mixer for 2 minutes. The magnesium stearate is added and the entire blend is then passed through a 600 micron mesh screen, returned to the glass jar, and blended in a Turbula mixer for 2 additional minutes. Core tablets are compressed using a Carver Press with $^{11}\!/_{32}$ inch (8.7 mm) round standard concave tooling at 1.2 metric ton (MT) force. The core tablets have a final hardness of approximately 13.1 kp (~128 Newtons).

The cores of the Table 4B tablets are made according to the following steps. The tablet cores are prepared using a wet granulation process. Two granulations of batch size 170.0 g each are prepared. The (N,N-Diethylcarbamoyl)methyl methyl (2E)but-2-ene-1,4-dioate is passed through a Quadro Comil U5 with a 610 or 813 micron screen at 2000 rpm. Hydroxypropyl cellulose is passed through a 500 micron mesh screen. The (N,N-Diethylcarbamoyl)methyl methyl (2E)but-2-ene-1,4-dioate and hydroxypropyl cellulose are granulated with purified water using a Diosna P1/6 equipped with a 1 L bowl. The wet granules are dried on trays in an oven at 30° C. The core blend batch size is 300.0 g. The dried granules, lactose monohydrate, croscarmellose sodium, and the silicon dioxide are screened through a 600 micron mesh screen and then blended in a V-blender for 5 minutes. The magnesium stearate is screened through a 425 micron mesh screen and blended with the other tablet core formulation components in a V-blender for 2 minutes. The tablet cores are compressed using a Korsch XL100 rotary press with $^{11}\!/_{32}$ inch (8.7 mm) round standard concave tooling at approximately 6-7 kN force. The cores have a final hardness of approximately 12 kp.

The tablet cores from Tables 4A and 4B are film-coated according to the following process. An aqueous suspension is prepared by mixing with an impeller 68.85 g Opadry 03019184 with 792.0 g of purified water. The water contained in the suspension is removed during the film coating process and is therefore not included in the formulations in Tables 4A and 4B. The tablets are coated with the aqueous suspension in an O'Hara Technologies Labcoat M coater with a 12" (30.5 cm) diameter perforated pan until the desired weight gain of barrier coat is achieved. The coating process occurs at an inlet temperature of approximately 52° C. and an outlet temperature of 37° C. After coating, the tablets are dried for 2 hours at 40° C. An aqueous suspension is prepared by mixing with an impeller methacrylic acid copolymer dispersion, triethyl citrate, PlasACRYL™ T20 with water. The water contained in the methacrylic acid copolymer dispersion and the PlasACRYL™ T20 is removed during the film coating process and therefore is not included in the formulations in Tables 4A and 4B. The tablets are coated with the aqueous suspension in an O'Hara Technologies Labcoat M coater with a 12 inch (30.5 cm) diameter perforated pan until the desired weight gain of enteric film is achieved. The coating process occurs at an inlet temperature of approximately 36° C. and an outlet temperature of 29° C.

Example 6

Delayed sustained release tablets containing (N,N-Diethylcarbamoyl)methyl methyl (2E)but-2-ene-1,4-dioate are made having the ingredients shown in Table 5:

TABLE 5

| Component | Manufacturer | Role | Quantity (mg/tablet) | Quantity (% w/w of core) |
|---|---|---|---|---|
| (N,N-Diethylcarbamoyl)methyl methyl (2E)but-2-ene-1,4-dioate | XenoPort (Santa Clara, CA) | Drug substance | 200.00 | 66.93 |
| Hydroxypropyl Cellulose | Aqualon (Hopewell, VA) | Binder | 6.19 | 2.07 |
| Lactose Monohydrate | Foremost (Rothschild, WI) | Filler | 44.83 | 15.00 |
| Hypromellose 2208 | Dow Chemical (Midland, MI) | Sustained release agent | 44.83 | 15.00 |
| Magnesium Stearate | Mallinckrodt (St. Louis, MO) | Lubricant | 2.99 | 1.00 |
| | | Total Core | 298.84 | 100.00 |
| Opadry 03O19184 | Colorcon (West Point, PA) | Barrier coat | 7.11 | 2.38 |
| | | Total Barrier Coating | 7.11 | 2.38 |
| Methacrylic Acid Co-polymer Dispersion | Evonik Industries (Essen, Germany) | Enteric polymer | 20.27 | 6.78 |
| Triethyl Citrate | Moreflex (Greensboro, NC) | Plasticizer | 1.05 | 0.35 |
| PlasACRYL ™ T20 | Emerson Resources (Norristown, PA) | Anti-tacking agent | 2.02 | 0.68 |
| | | Total Enteric Coating | 23.34 | 7.81 |
| | | Total Tablet | 329.29 | 110.19 |

The tablets are made according to the following steps. The core tablets are prepared using a wet granulation process. The granulation batch size is 170 g. The (N,N-Diethylcarbamoyl)methyl methyl (2E)but-2-ene-1,4-dioate is passed through a Quadro Comil U5 with an 813 micron screen at 2000 rpm. Hydroxypropyl cellulose is passed through a 500 micron mesh screen. The (N,N-Diethylcarbamoyl)methyl methyl (2E)but-2-ene-1,4-dioate and hydroxypropyl cellulose are granulated with purified water using a Diosna P1/6 equipped with a 1 L bowl. The wet granules are screened through an approximately 1180 micron mesh screen and are dried on trays in an oven at 30° C. for approximately 4 hours. The core blend batch size is 80.0 g. The tablet core materials are blended in a Turbula mixer. Core tablets (298.84 mg) are compressed using a Manesty Flexitab with $^{11}/_{32}$" round standard concave tooling at approximately 15 kN force. The core tablets have a final hardness of approximately 11 kp. An aqueous suspension is prepared by mixing with an impeller 68.85 g Opadry 03019184 with 792.0 g of purified water. The water contained in the suspension is removed during the film coating process and is therefore not included in the formulation in Table 5. The tablets are coated with the aqueous suspension in an O'Hara Technologies Labcoat M coater with a 12" (30.5 cm) diameter perforated pan until the desired weight gain of barrier coat is achieved. The coating process occurs at an inlet temperature of approximately 52° C. and an outlet temperature of 37° C. After coating, the tablets are dried for 2 hours at 40° C. An aqueous suspension is prepared by mixing with an impeller 405.1 g methacrylic acid copolymer dispersion, 6.3 g triethyl citrate, 60.6 g PlasACRYL™ T20 with 228.1 g water. The water contained in the methacrylic acid copolymer dispersion and the PlasACRYL™ T20 is removed during the film coating process and therefore not included in the formulation in Table 5. The tablets are coated with the aqueous suspension in an O'Hara Technologies Labcoat M coater with a 12 inch (30.5 cm) diameter perforated pan until the desired weight gain of enteric film is achieved. The coating process occurs at an inlet temperature of approximately 36° C. and an outlet temperature of 29° C.

Example 7

Figure 4:
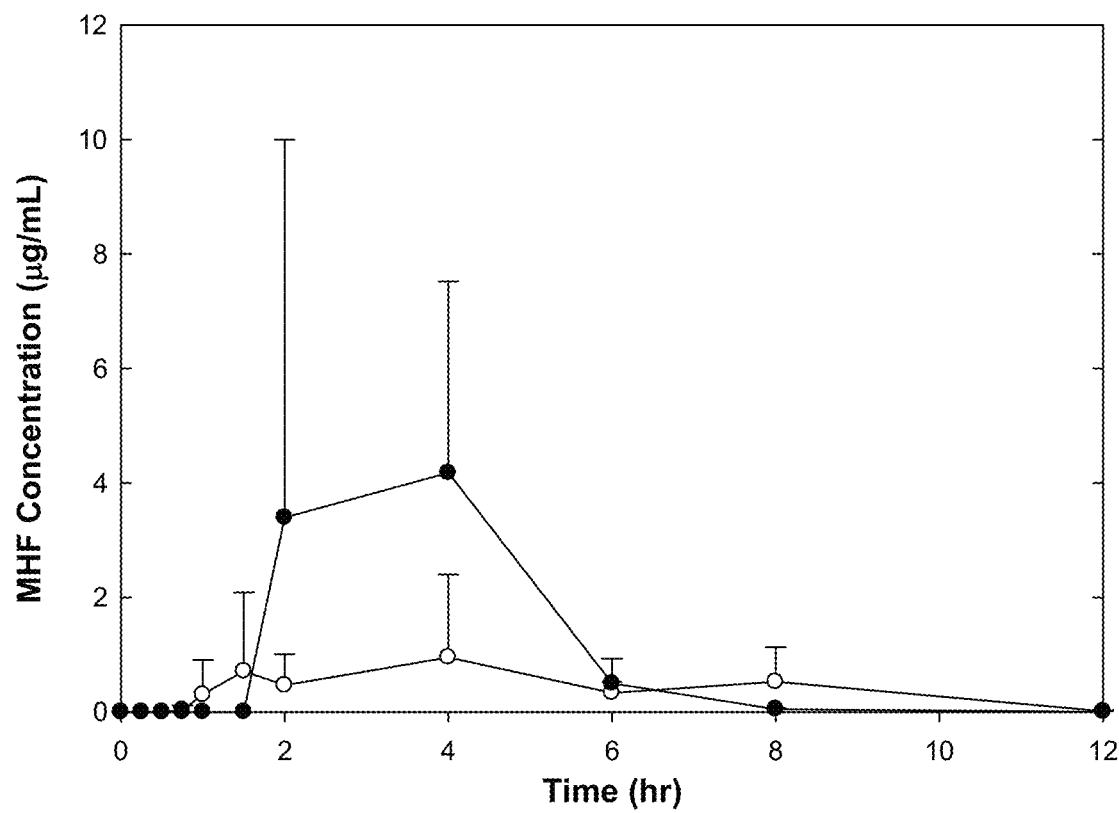
FIG. 4 is a graph showing the concentration of MHF in the blood of fed monkeys following administration of the oral dosage forms similar to those of Examples 5 and 6.
Figure 5:
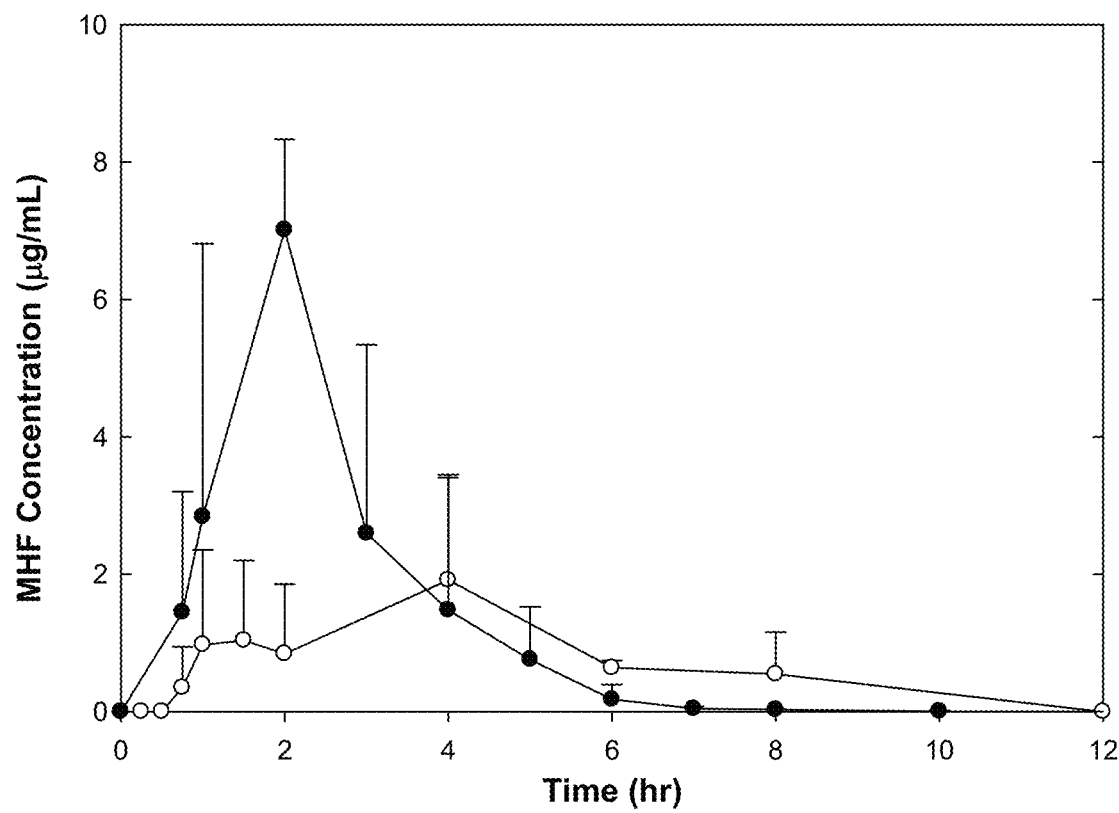
FIG. 5 is a graph showing the concentration of MHF in the blood of fasted monkeys following administration of the oral dosage forms similar to those of Examples 5 and 6.

The concentration±1 SD of MHF in the blood of Cynomologous monkeys following oral dosing of delayed release enteric coated tablets, which have the same formulation as the tablets of Examples 5 and 6, except that no Opadry barrier layer was present in the tested tablets, is shown in FIGS. 4 and 5. The data in FIG. 4 is from animals that were dosed in a fed state and the data in FIG. 5 is from animals that were dosed in a fasted state. Two groups of tablets were tested. Tablets having the same formulation as described in Table 4A tablets, except that the Opadry barrier layer was not present, produced the pharmacokinetic curve shown with ●—● symbols in FIG. 4. Tablets having the same formulation as described in Table 4B, except that the Opadry barrier layer was not present, produced the pharmacokinetic curve shown with ●—● symbols in FIG. 5. In these Figures, the MHF concentrations following dosing with tablets having the formulation of Example 6 tablets are shown with ○—○ symbols. It is believed that tablets made according to the exact formulations of Examples 5 and 6, with the Opadry barrier layer present, would exhibit substantially the same pharmacokinetic profiles as are shown in FIGS. 4 and 5 since the Opadry barrier layer is quickly dissolved in the gut and does not substantially affect the rate or timing of MHF prodrug release from the tablet core.

Administration Protocol

Tablets having the same formulations as the tablets disclosed in Examples 5 and 6 (200 mg of (N,N-Diethylcarbamoyl)methyl methyl (2E)but-2-ene-1,4-dioate per tablet), but without any Opadry barrier layer present, were administered by oral dosing to groups of four adult male Cynomologous (*Macaca fascicularis*) monkeys (each monkey weighs about 4 to 5 kg). Each monkey was administered one tablet while in a fasted state or while in a fed state. All animals were fasted overnight before the study. For the fed leg, animals were administered blended food via oral gavage in the morning 30 minutes prior to administration of each test formulation. For the fasted leg, the animals remain fasted for 4 hours post-dosing. Blood samples (1.0 mL) were obtained from all animals via the femoral vein at pre-dose and intervals over 24 hours after oral dosing. Blood was collected in pre-chilled $K_2$EDTA, quenched with acetonitrile and stored at −50° C. to −90° C. until analysis. There was a minimum of 7 day wash out period between dosing sessions.

Sample Preparation for Absorbed Drug

300 μL of acetonitrile was added to 1.5 mL Eppendorf tubes for the preparation of samples and standards.
Sample Preparation: Blood was collected at different time points and immediately 100 μL of blood was added into Eppendorf tubes containing 300 μL of methanol and mixed by vortexing.
Standard Preparation: One hundred μL of blood was added to 290 μL of acetonitrile in Eppendorf tubes. 10 μL of MHF standard solution (0.2, 0.5, 1, 2.5, 5, 10, 25, 50 and 100 μg/mL) was added to each tube to make up the final calibration standards (0.02, 0.05, 0.1, 0.25, 0.5, 1, 2.5, 5 and 10 μg/mL).
A 150 μL aliquot of supernatant from quenched blood standards, QCs and samples was transferred to a 96-well plate and 20 μL of the internal standard solution was added to each well, the plate was capped and vortexed well. The supernatant was injected onto the API 4000 LC/MS/MS system for analysis LC/MS/MS Analysis
The concentration of MHF in monkey blood was determined using an API 4000 LC/MS/MS instrument equipped with Agilent Binary pump and autosampler. The column was a Luna C8 (2) 4.6×150 mm, 5μ column operating at 2 to 8° C. temperature. The mobile phases were (A) 0.1% formic acid in water, and (B) 0.1% formic acid in acetonitrile. The gradient condition was: 2% B for 1 min, increasing to 95% B in 3.5 min and maintained for 2 min, then decreasing to 2% B in 5.6 min and maintained for 2.3 min. 30 μL of sample was injected into the column. A Turbo-Ion Spray source was used, and was detected in negative ion mode for the MRM transition of 128.95/84.8. Peaks were integrated using Analyst 1.5 quantitation software.

Example 8

A randomized, double-blind crossover, food effect, single-dose study of the safety, tolerability, and pharmacokinetics of two oral dosage forms of (N,N-Diethylcarbamoyl)methyl methyl (2E)but-2-ene-1,4-dioate in healthy adult subjects was conducted. Twenty-four healthy adult volunteers (males and females) participated in the study. Twelve of the subjects received a dosage form of Example 1, once in a fed condition and once in a fasted condition, with a two-week washout between treatments. Twelve other subjects received a dosage form of Example 2, once in a fed condition and once in a fasted condition, with a two-week washout between treatments. The fasted dosing was achieved by dosing the subject following an overnight fast while the fed dosing was achieved by dosing the subject after consuming a high fat-content breakfast. Each of the two tested dosage forms contained 200 mg of (N,N-Diethylcarbamoyl)methyl methyl (2E)but-2-ene-1,4-dioate (107 mg equivalents of methyl hydrogen fumarate).

Blood samples were collected from all subjects prior to dosing, and at 0.5, 1, 1.5, 2, 3, 4, 5, 6, 7, 8, 10, 12, 16, 24, 30, 36, 48, 60, 72, 84, 96, 108 and 120 hours after dosing. Urine samples were collected from all subjects prior to dosing, and complete urine output was obtained at the 0-4, 4-8, 8-12, 12-24, 24-36, 36-48, 48-72, 72-96 and 96-120 hour intervals after dosing. Blood samples were quenched immediately with acetonitrile and frozen. Sample aliquots were prepared for analysis of (i) methyl hydrogen fumarate, (ii) (N,N-Diethylcarbamoyl)methyl methyl (2E)but-2-ene-1,4-dioate, (iii) N,N diethyl-2-hydroxy acetamide and (iv) (2S,3S,4S,5R,6R)-6-[(N, N-diethylcarbamoyl)methoxy]-3,4,5-trihydroxy-2H-3,4,5,6-tetrahydropyran-2-carboxylic acid, the latter two being other potential metabolites of (N,N-Diethylcarbamoyl)methyl methyl (2E)but-2-ene-1,4-dioate, using sensitive and specific LC/MS/MS methods.

Figure 6:
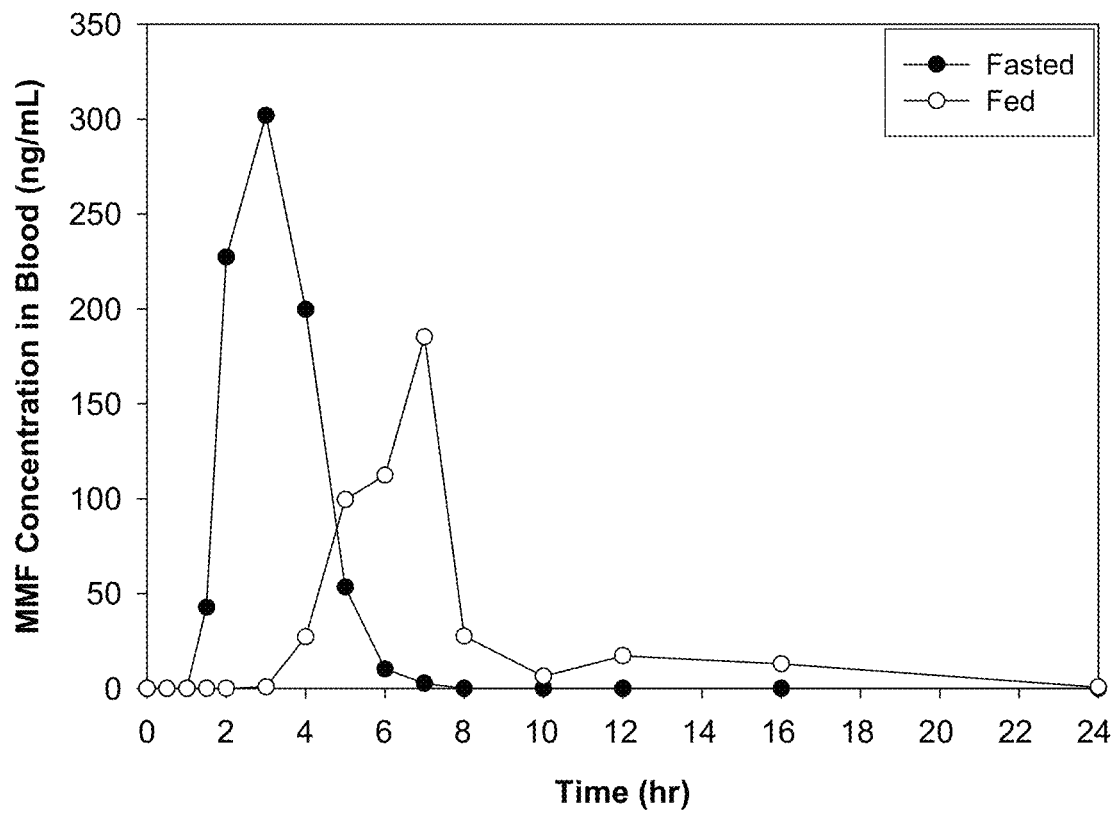
FIG. 6 is a graph showing the concentration of MMF in the blood in fed and fasted healthy human patients following administration of the oral dosage form of Example 1.

The plasma concentration of MMF following oral dosing of the formulation prepared according to Example 1 to fasted and fed healthy adult patients is shown in FIG. 6. Table 6 shows the preliminary mean (SD) pharmacokinetic data for (N,N-Diethylcarbamoyl)methyl methyl (2E)but-2-ene-1,4-dioate in fed and fasted patients.

TABLE 6

| N | Food | $C_{max}$ (ng/mL) | $T_{max}$ (hr) | $AUC_{inf}$ (ng · hr/mL) |
| --- | --- | --- | --- | --- |
| 12 | Fasted | 529 (233) | 2.83 (0.84) | 762 (248) |
| 12*/11**/7*** | Fed | 366* (320) | 8.82** (4.40) | 807*** (445) |

The formulation produced mean (SD) maximum MMF concentrations (Cmax) of 529 (233) ng/mL fasted and 366 (320) ng/mL fed. MMF AUC was 762 (248) ng*h/mL fasted and 807 (445) ng*h/mL fed. The time to peak concentration (Tmax) was 2.83 (0.84) hr fasted and 8.82 (4.40) hr fed. (N,N-Diethylcarbamoyl)methyl methyl (2E)but-2-ene-1,4-dioate was well tolerated during the trial. All 12 subjects completed the dosing period. All adverse events were mild. Adverse events reported in more than one subject and more frequently for (N,N-Diethylcarbamoyl)methyl methyl (2E)but-2-ene-1,4-dioate than for placebo were flushing and feeling hot. A comparison of these adverse events of the formulation to placebo is shown in Table 7.

TABLE 7

| | Flushing | | Feeling Hot | |
| --- | --- | --- | --- | --- |
| | Fasted | Fed | Fasted | Fed |
| Placebo | 0 | 1 | 0 | 0 |
| Example 1 Formulation | 7 | 5 | 0 | 3 |

Figure 7:
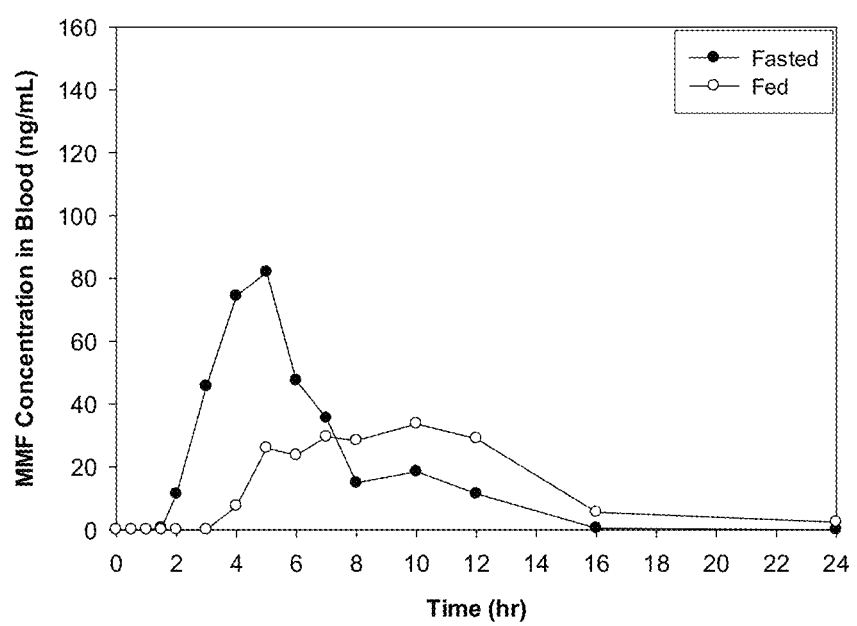
FIG. 7 is a graph showing the concentration of MMF in the blood in fed and fasted healthy human patients following administration of the oral dosage form of Example 2.

The plasma concentration of MMF following oral dosing of the formulation prepared according to Example 2 to fasted and fed healthy adult patients is shown in FIG. 7. Table 8 shows the preliminary mean (SD) pharmacokinetic data for (N,N-Diethylcarbamoyl)methyl methyl (2E)but-2-ene-1,4-dioate in fed and fasted patients.

TABLE 8

| N | Food | $C_{max}$ (ng/mL) | $T_{max}$ (hr) | $AUC_{inf}$ (ng · hr/mL) |
| --- | --- | --- | --- | --- |
| 12*/8** | Fasted | 95* (26) | 4.17* (0.84) | 400** (166) |
| 12*/5*** | Fed | 80* (39) | 9.92* (5.50) | 377*** (132) |

The formulation produced mean (SD) maximum MMF concentrations (Cmax) of 95 (26) ng/mL fasted and 80 (39) ng/mL fed. MMF AUC was 400 (160) ng*h/mL fasted and 377 (132) ng*h/mL fed. The time to peak concentration (Tmax) was 4.17 (0.84) hr fasted and 9.92 (5.50) hr fed. Promoiety was cleared from blood with a half life around 3 hours.

The (N,N-Diethylcarbamoyl)methyl methyl (2E)but-2-ene-1,4-dioate was well tolerated during the trial. All 12 subjects completed the dosing period. All adverse events were mild. One subject in the (N,N-Diethylcarbamoyl)methyl methyl (2E)but-2-ene-1,4-dioate fed group reported flushing more frequently than in the fed placebo group. No subjects in the fasted (N,N-Diethylcarbamoyl)methyl methyl (2E)but-2-ene-1,4-dioate group reported flushing, and no subjects in either the fed or fasted (N,N-Diethylcarbamoyl)methyl methyl (2E)but-2-ene-1,4-dioate groups reported feeling hot more than for placebo. A comparison of these adverse events of the formulation to placebo is shown in Table 9.

TABLE 9

| | Flushing | | Feeling Hot | |
| --- | --- | --- | --- | --- |
| | Fasted | Fed | Fasted | Fed |
| Placebo | 0 | 1 | 0 | 0 |
| Example 2 Formulation | 1 | 1 | 0 | 0 |

Example 9

Size 00 gelatin capsules containing 477 mg of extended-release (N,N-Diethylcarbamoyl)methyl methyl (2E)but-2-ene-1,4-dioate-containing pellets were manufactured with the formulation shown in Table 10:

TABLE 10

| Component | Manufacturer | Role | Quantity (mg/capsule) | Quantity (% w/w) |
|---|---|---|---|---|
| (N,N-Diethylcarbamoyl)methyl methyl (2E)but-2-ene-1,4-dioate | Cambridge (Germantown, WI) | Drug substance | 200.00 | 60.00 |
| Microcrystalline Cellulose | FMC (Newark, DE) | Filler | 133.33 | 40.00 |
| | | Total Pellet Core | 333.33 | 100.00 |
| Ethylcellulose | Ashland (Hopewell VA) | Water-insoluble coating agent | 20.56 | 6.17 |
| Hydroxypropyl Cellulose | Ashland (Hopewell VA) | Water soluble coating agent | 5.00 | 1.50 |
| Talc | Luzenac (Houston TX) | Anti-tacking agent | 5.00 | 1.50 |
| Dibutyl sebacate | Vertellus (Greensboro, NC) | Plasticizer | 2.78 | 0.83 |
| | | Total Barrier/Sustained Release Coating | 33.33 | 10.00 |
| Methacrylic Acid Co-polymer Dispersion | Evonik (Darmstadt, Germany) | Enteric coating agent | 88.55 | 24.15 |
| Triethyl Citrate | Vertellus (Greensboro, NC) | Plasticizer | 14.30 | 3.90 |
| PlasACRYL T20 | Emerson (Norristown, PA) | Anti-tacking agent | 7.15 | 1.95 |
| | | Total Enteric Coating | 110.00 | 30.00 |
| VCaps Plus Size 00 Capsule | Capsugel (Puebla, Mexico) | Capsule | 111-125 | 23.29-26.22 |

The capsules were manufactured according to the following process. An extrusion/spheronization process was selected for the manufacture of the core pellets for the capsules. The (N,N-Diethylcarbamoyl)methyl methyl (2E)but-2-ene-1,4-dioate was first screened then mixed with microcrystalline cellulose. This blend was then formed into a wet mass with the addition of aqueous acetate buffer (pH 3.5) and the mass then extruded through a 1.0 mm screen and the extrudates were spheronized (at 1200 rpm for 3 minutes) to form the core pellets. These core pellets are then classed to retain the pellets within 0.85 mm to 1.4 mm before the next processing step. The pellets were then coated with the target amount of the sustained release membrane using a hydroalcoholic mixture of ethylcellulose and hydroxypropyl cellulose. This coating was performed in a Wurster-type coater (product temperature at 30° C. and spray rate at 10 g/minute). The overall coating time was approximately 2 hours. The coated pellets were dried further in an oven to remove any residual solvent. The dried sustained release film-coated pellets were then enteric coated to the target amount by aqueous film coating in a Wurster-type coater (product temperature at 30° C. and a spray rate at 10 g/min). The overall coating time was approximately 2 hours. The capsules were then filled with the appropriate amount of pellets to achieve the desired dose strength.

Example 10

Size 0 gelatin capsules containing 469 mg of extended-release (N,N-Diethylcarbamoyl)methyl methyl (2E)but-2-ene-1,4-dioate-containing pellets were manufactured according to the formulation shown in Table 11:

TABLE 11

| Component | Manufacturer | Role | Quantity (mg/capsule) | Quantity (% w/w) |
|---|---|---|---|---|
| (N,N-Diethylcarbamoyl)methyl methyl (2E)but-2-ene-1,4-dioate | Cambridge (Germantown, WI) | Drug substance | 200.00 | 60.00 |
| Microcrystalline Cellulose | FMC (Little Island, Ireland) | Filler | 112.47 | 33.74 |
| Hydroxypropyl Cellulose | Ashland (Hopewell VA) | Binder | 16.67 | 5.00 |
| Croscarmellose Sodium | FMC (Little Island, Ireland) | Disintegrant | 4.20 | 1.26 |
| | | Total Pellet Core | 333.33 | 100.00 |
| Ethylcellulose | Dow Chemical (Midland, MI) | Water-insoluble coating agent | 25.00 | 7.50 |

TABLE 11-continued

| Component | Manufacturer | Role | Quantity (mg/capsule) | Quantity (% w/w) |
|---|---|---|---|---|
| Hydroxypropyl Cellulose | Ashland (Hopewell VA) | Water soluble coating agent | 8.33 | 2.50 |
| Talc | Imerys (Porte, Italy) | Anti-tacking agent | 6.67 | 2.00 |
| Dibutyl sebacate | Vertellus (Greensboro, NC) | Plasticizer | 1.67 | 0.50 |
| | | Total Barrier/ Sustained Release Coating | 41.67 | 12.50 |
| Hypromellose Acetate Succinate | ShinEtsu (Niigata, Japan) | Enteric coating agent | 93.75 | 25.00 |
| | | Total Enteric Coating | 93.75 | 25.00 |
| VCap Plus Size 0 Capsule | Capsulgel (Colmar, France) | Capsule | 88-104 | 18.8-22.2 |

An extrusion/spheronization process was selected for the manufacture of the core active drug substance pellets. The manufacturing process consisted of first screening or milling the (N,N-Diethylcarbamoyl)methyl methyl (2E)but-2-ene-1,4-dioate API. The screened API was then mixed with microcrystalline cellulose, croscarmellose sodium and hydroxypropyl cellulose. These materials were then formed into a wet mass with the addition of purified water. The wet mass was extruded through a 1.0 mm screen and the extrudates were spheronized (800 rpm for 2 minutes) to form the core pellets. These core pellets were then classed to retain the pellets with particle size within 0.71 mm to 1.25 mm before the next processing step. The pellets were then coated with the target amount of the sustained release membrane which was based on a mixture of ethylcellulose and hydroxypropyl cellulose. This coating was performed in a Wurster-type coater (product temperature at 31° C. and spray rate at 12 g/min. The total coating time was approximately 3 hours. The dried sustained release film-coated pellets were then enteric coated to the target amount by film coating in a Wurster-type coater (product temperature at 34° C. and spray rate at 7 g/min). The total coating time was approximately 12 hours. The coated pellets were dried in an oven to remove any residual solvent. Capsules were then filled with the appropriate amount of pellets to achieve the desired dose strength.

Example 11

11a Pellets

Pellets having the same formulation as those described in Example 9, but which do not contain hydroxypropyl cellulose nor croscarmellose sodium in the core formulation, were manufactured according to the method described in Example 9. The particle size distribution was measured by passing approximately 100 g of raw pellets through sieves with mesh size range from 0.50 mm to 1.4 mm. The amount of pellets retained on each screen was then calculated. A pellet yield of 53% was observed in a formulation that contains only (N,N-Diethylcarbamoyl)methyl methyl (2E) but-2-ene-1,4-dioate and microcrystalline cellulose.

| Undersized Pellets (%) | Target-sized Pellets (%) (0.85 to 1.4 mm size range) | Oversized Pellets (%) |
|---|---|---|
| 15 | 53 | 32 |

11 b Pellets

Pellets having the same formulation as those described in Example 10 were manufactured according to the method described in Example 10. The particle size distribution was measured by passing approximately 100 g of raw pellets through sieves with mesh size range from 0.5 mm to 1.4 mm. The amount of pellets retained on each screen was then calculated. A yield of 93% was observed in a formulation that contains a binder (hydroxypropyl cellulose) and a disintegrant (croascarmellose sodium) in addition to the (N,N-Diethylcarbamoyl)methyl methyl (2E)but-2-ene-1,4-dioate and microcrystalline cellulose.

| Undersized Pellets (%) | Target-sized Pellets (%) (0.71 to 1.25 mm size range) | Oversized Pellets (%) |
|---|---|---|
| 2 | 93 | 5 |

Comparing the pellet size distribution of the 11b pellets with that of 11a pellets shows that the presence of hydroxypropyl cellulose provides a higher percentage of target-sized pellets, which gives a more consistent total surface area, which leads to a more uniform coating and prodrug release.

Example 12

A two-stage dissolution method was used to determine the in vitro dissolution profile of dosage forms prepared according to Examples 9 and 10 in order to mimic the conditions of a dosage form as it transits the gastrointestinal tract. Thus, the dosage forms were first placed into a dissolution medium having a pH of 1.2, to mimic the conditions of the stomach, and then placed into a dissolution medium of pH 6.8, to mimic the conditions of the intestines. The dissolution vessel (USP, Type I, basket) initially contained 750 mL of 0.1 N hydrochloric acid (pH 1.2). After 2 hours of dissolution, 250 mL of 200 mM tribasic sodium phosphate was added to the vessel resulting in a pH adjustment from 1.2 to 6.8. The dissolution medium was kept at 37° C. and was agitated at 100 rpm.

Samples of the dissolution medium were withdrawn at 1 and 2 hours following the start of the low pH stage, and at 0.5, 2, 4, 7, 10, 14, and 20 hours (only the Example 10 dosage forms were tested at time 20 hours) following start of the near-neutral pH stage. The concentration of (N,N-

Diethylcarbamoyl)methyl methyl (2E)but-2-ene-1,4-dioate in solution was determined using reverse phase HPLC using a C18 column and a phosphoric acid/acetonitrile/water isocratic mobile phase with photodiode detection at 210 nm.

Figure 8:
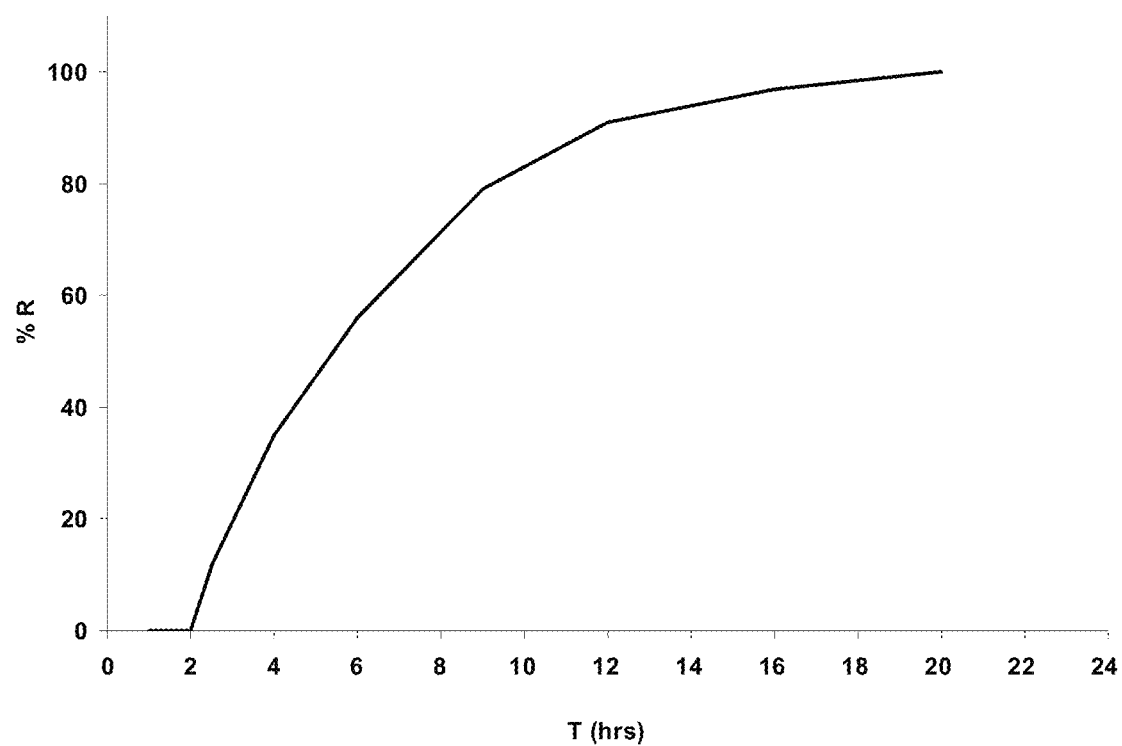
FIG. 8 is a graph showing the in vitro MHF prodrug release profile (percent MHF prodrug released over time) for the dosage forms of Example 9, tested in accordance with Example 12.

The percent of prodrug released from the Example 9 dosage forms over time is shown in FIG. 8. These dosage forms showed no prodrug release in the first 2 hours (acid stage) of testing. Slow prodrug release was observed after the dissolution medium pH was adjusted to 6.8. Full prodrug release was achieved after about 20 hours in pH 6.8.

Figure 9:
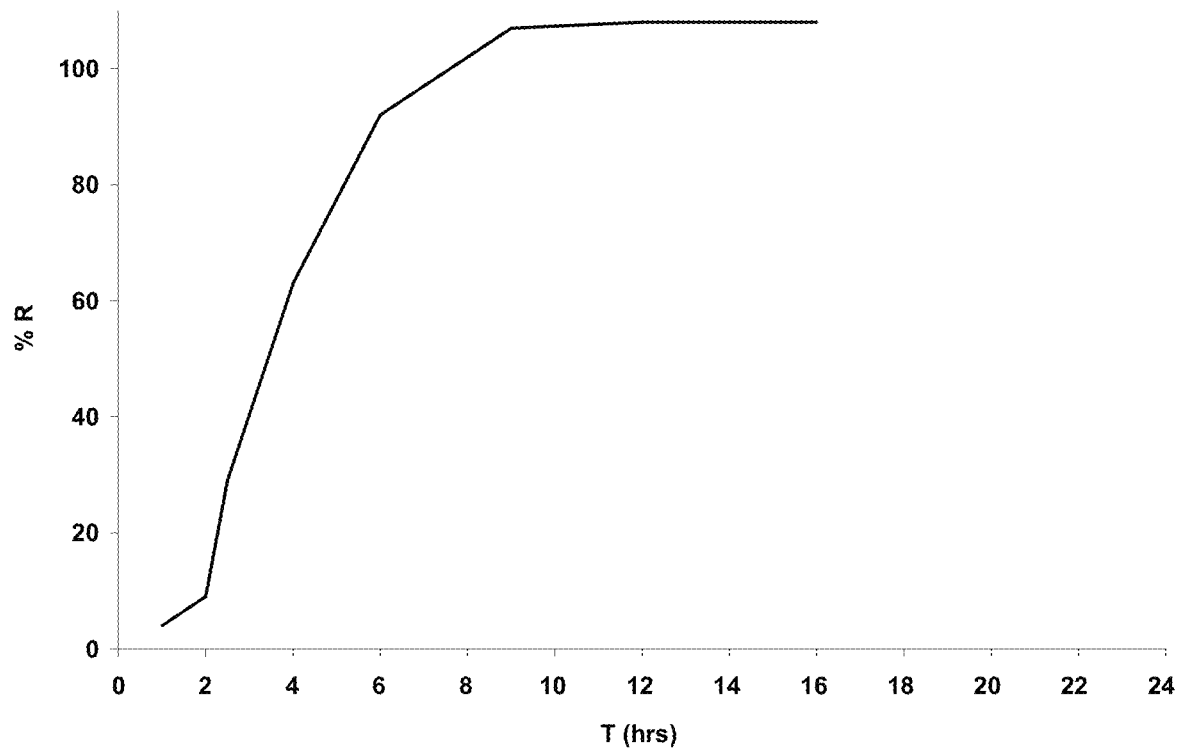
FIG. 9 is a graph showing the in vitro MHF prodrug release profile (percent MHF prodrug released over time) for the dosage forms of Example 10, tested in accordance with Example 12.

The percent of prodrug released from the Example 10 dosage forms over time is shown in FIG. 9. These dosage forms showed 9% prodrug release in the first 2 hours (acid stage) of testing. The prodrug release rate increased after the pH of the dissolution medium was adjusted to 6.8. Full prodrug release was achieved in about 9 hours.

Example 13

Figure 10:
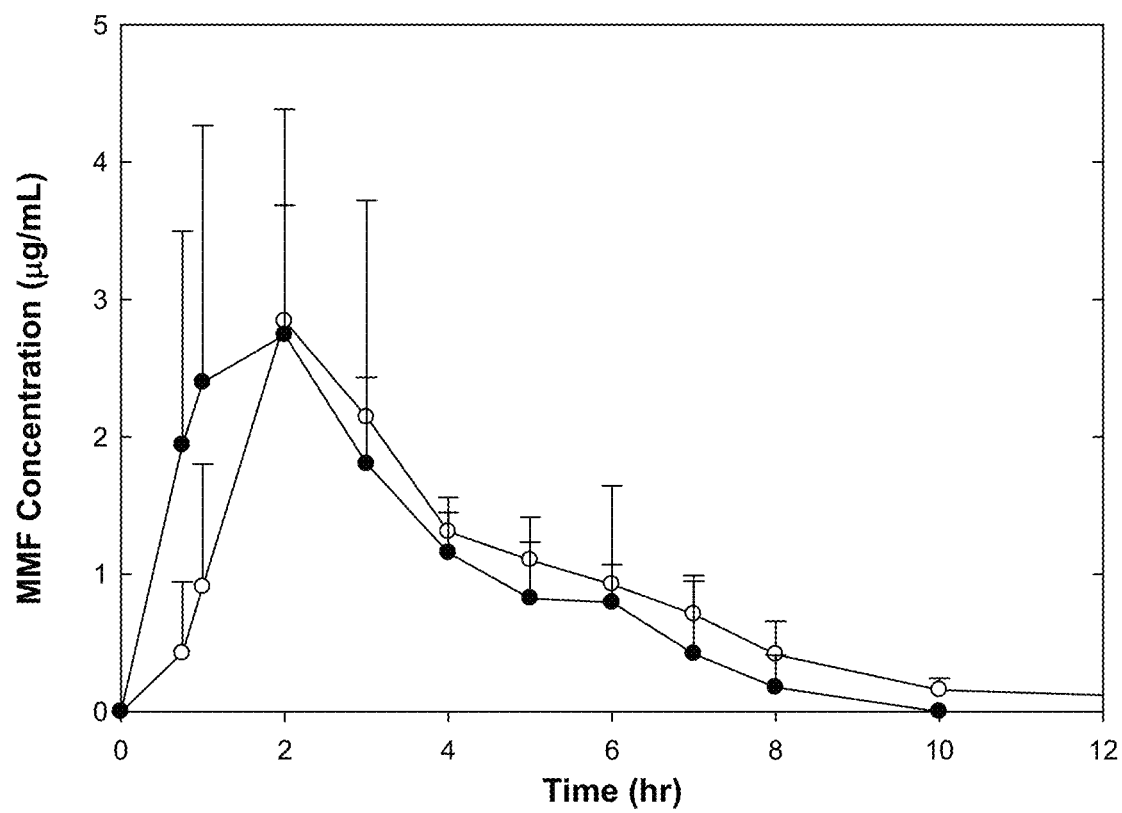
FIG. 10 is a graph showing the concentration of MHF in the blood of fasted monkeys following administration of the oral dosage forms of Example 9.
Figure 11:
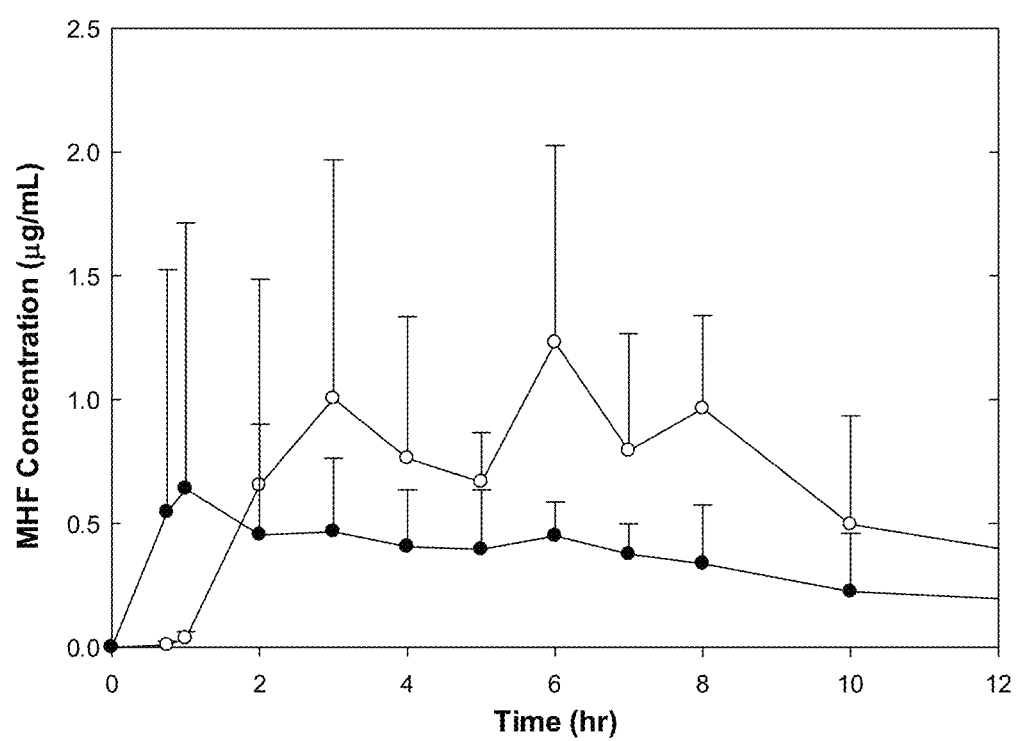
FIG. 11 is a graph showing the concentration of MHF in the blood of fed monkeys following administration of the oral dosage forms of Example 9.

The concentration±1 SD of MHF in the blood of Cynomologous monkeys following oral dosing of delayed release dosage forms (enteric coated pellets loaded into a capsule) prepared according to Examples 9 and 10 is shown in FIGS. 10 and 11. In these Figures, the MHF concentrations following dosing with the Example 10 dosage forms are shown with ●—● symbols and the MHF concentrations following dosing with the Example 9 dosage forms are shown with ○—○ symbols. The data in FIG. 10 is from animals dosed in a fasted state and the data in FIG. 11 is from animals dosed in a fed state.

Administration Protocol

Capsules prepared according to Example 9 (200 mg (N,N-Diethylcarbamoyl)methyl methyl (2E)but-2-ene-1,4-dioate per capsule) were administered by oral dosing to groups of four adult male Cynomologous (*Macaca fascicularis*) monkeys (each monkey weighed about 4 to 5 kg). Each monkey was administered one tablet in either a fasted or in a fed state. All animals were fasted overnight before the study. For the fed leg, animals were administered blended food via oral gavage in the morning 30 minutes prior to administration of each test formulation. For the fasted leg, the animals remained fasted for 4 hours post-dosing. Blood samples (1.0 mL) were obtained from all animals via the femoral vein at pre-dose and intervals over 24 hours after oral dosing. Blood was collected in pre-chilled K₂EDTA, quenched with acetonitrile and stored at −50° C. to −90° C. until analyzed. There was a minimum 7 day wash out period between dosing sessions.

Sample Preparation for Absorbed Drug

300 μL of acetonitrile was added to 1.5 mL Eppendorf tubes for the preparation of samples and standards.

Sample Preparation: Blood was collected at different time points and immediately 100 μL of blood was added into Eppendorf tubes containing 300 μL of methanol and mixed by vortexing.

Standard Preparation: One hundred μL of blood was added to 290 μL of acetonitrile in Eppendorf tubes. 10 μL of MMF standard solution (0.2, 0.5, 1, 2.5, 5, 10, 25, 50 and 100 μg/mL) was added to each tube to make up the final calibration standards (0.02, 0.05, 0.1, 0.25, 0.5, 1, 2.5, 5 and 10 μg/mL).

A 150 μL aliquot of supernatant from quenched blood standards, QCs and samples was transferred to a 96-well plate and 20 μL of the internal standard solution was added to each well, the plate was capped and vortexed well. The supernatant was injected onto the API 4000 LC/MS/MS system for analysis.

LC/MS/MS Analysis

The concentration of MHF in monkey blood was determined using an API 4000 LC/MS/MS instrument equipped with Agilent Binary pump and autosampler. The column was a Luna C8 (2) 4.6×150 mm, 5μ column operating at 2 to 8° C. temperature. The mobile phases were (A) 0.1% formic acid in water, and (B) 0.1% formic acid in acetonitrile. The gradient condition was: 2% B for 1 min, increasing to 95% B in 3.5 min and maintained for 2 min, then decreasing to 2% B in 5.6 min and maintained for 2.3 min. 30 μL of sample was injected into the column. A Turbo-Ion Spray source was used, and was detected in negative ion mode for the MRM transition of 128.95/84.8. Peaks were integrated using Analyst 1.5 quantitation software.

Example 14

Figure 12:
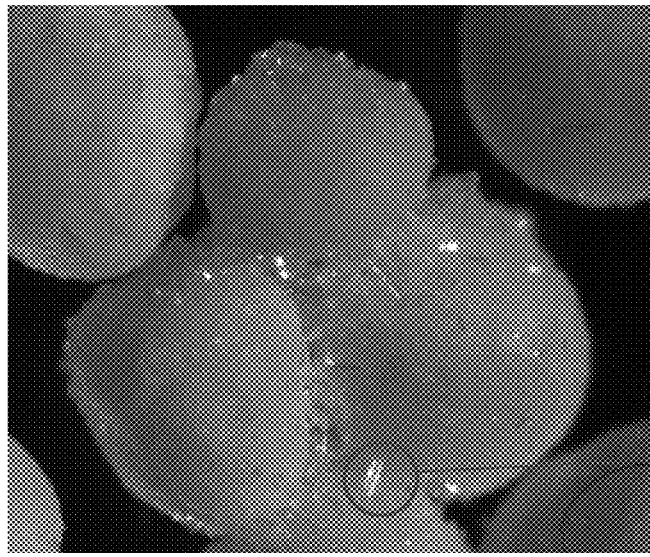
FIG. 12 is an electron micrograph of (N,N-Diethylcarbamoyl)methyl methyl (2E)but-2-ene-1,4-dioate-containing pellets prepared at pH 4.1 as described in Example 14.

This example describes the use of certain buffers to control surface crystallization of (N,N-Diethylcarbamoyl)methyl methyl (2E)but-2-ene-1,4-dioate on prodrug-containing pellets made in accordance with a process similar to that disclosed in Example 10, but where the acetate buffer is at pH 4.1. When the wet (N,N-Diethylcarbamoyl)methyl methyl (2E)but-2-ene-1,4-dioate-containing pellets are dried, it was observed that large crystals of (N,N-Diethylcarbamoyl)methyl methyl (2E)but-2-ene-1,4-dioate appear on the surface of the pellets as shown in FIG. 12. It was observed that large crystals migrate to the surface of the pellets and through drying and handling, these prodrug crystals tend to fall off the pellets, thereby reducing the prodrug content of the final product. Also, the crystals can serve to bridge individual pellets, leading to pellet agglomeration, which can compromise the subsequent coating processes.

In order to alter the crystallization condition, the pH of the acetate buffer was reduced from 4.1 to 3.5 (used in Example 10), so that a vast majority of the buffer existed as neutral acetic acid form, which can serve as a good hydrogen bonding donor to disrupt the intermolecular hydrogen bonding pattern of the crystal.

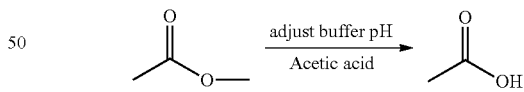

Figure 13:
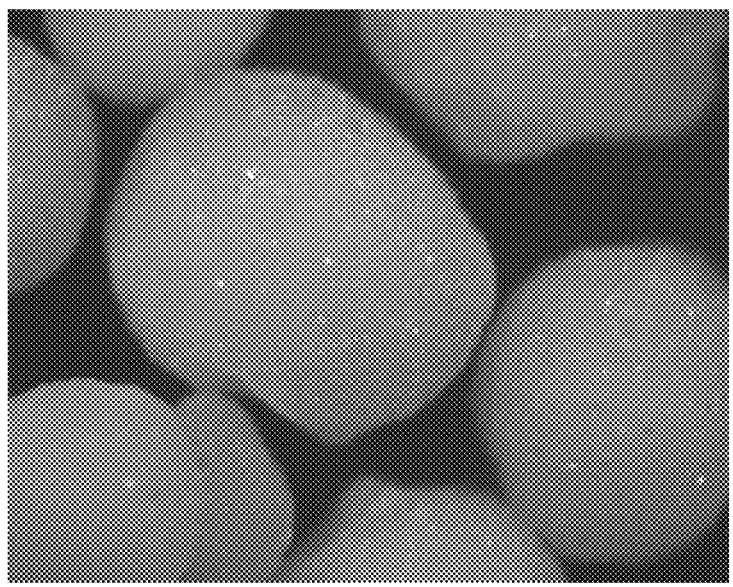
FIG. 13 is an electron micrograph of (N,N-Diethylcarbamoyl)methyl methyl (2E)but-2-ene-1,4-dioate-containing pellets prepared at pH 3.5 as described in Example 14.

Change of the acetate buffer from pH 4.1 to 3.5 was shown to significantly reduce the presence of large prodrug crystals on the surface of the resulting pellets as demonstrated in FIG. 13.

Example 15

A randomized, double-blind crossover, food effect, single-dose study of the safety, tolerability, and pharmacokinetics of a sustained release oral dosage form of (N,N-Diethylcarbamoyl)methyl methyl (2E)but-2-ene-1,4-dioate in healthy adult subjects was conducted. Twelve healthy adult volunteers (males and females) participated in the study. All twelve subjects received a dosage form of Example 9, once in a fed condition and once in a fasted condition, with a two-week washout between treatments. The fasted dosing was achieved by dosing the subject following an overnight fast while the fed dosing was achieved by dosing the subject after consuming a high fat-content breakfast. The dosage form contains 200 mg of (N,N-Diethylcarbamoyl)methyl methyl (2E)but-2-ene-1,4-dioate (107 mg equivalents of methyl hydrogen fumarate).

Blood samples were collected from all subjects prior to dosing, and at 0.5, 1, 1.5, 2, 3, 4, 5, 6, 7, 8, 10, 12, 16, 24, 30, 36, 48, 60, 72, 84, 96, 108 and 120 hours after dosing. Urine samples were collected from all subjects prior to dosing, and complete urine output was obtained at the 0-4, 4-8, 8-12, 12-24, 24-36, 36-48, 48-72, 72-96 and 96-120 hour intervals after dosing. Blood samples were quenched immediately with acetonitrile and frozen. Sample aliquots were prepared for analysis of (i) methyl hydrogen fumarate, (ii) (N,N-Diethylcarbamoyl)methyl methyl (2E)but-2-ene-1,4-dioate, (iii) N,N diethyl-2-hydroxy acetamide and (iv) (2S,3S,4S,5R,6R)-6-[(N, N-diethylcarbamoyl)methoxy]-3,4,5-trihydroxy-2H-3,4,5,6-tetrahydropyran-2-carboxylic acid, the latter two being other potential metabolites of (N,N-Diethylcarbamoyl)methyl methyl (2E)but-2-ene-1,4-dioate, using sensitive and specific LC/MS/MS methods.

Figure 14:
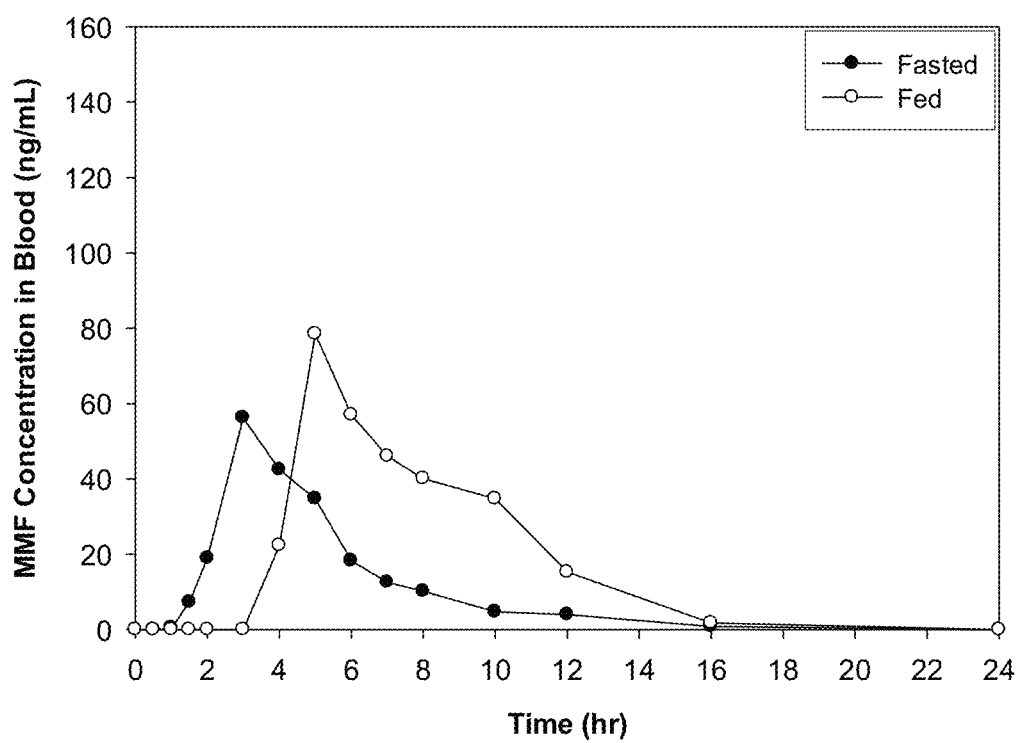
FIG. 14 is a graph showing the concentration of MMF in the blood in fed and fasted healthy human patients following administration of the oral dosage form of Example 10.

The plasma concentration of MMF following oral dosing of the formulation prepared according to Example 10 to fasted and fed healthy adult patients is shown in FIG. 14. Table 12 shows the preliminary mean (SD) pharmacokinetic data for (N,N-Diethylcarbamoyl)methyl methyl (2E)but-2-ene-1,4-dioate in fed and fasted patients.

TABLE 12

| N | Food | $C_{max}$ (ng/mL) | $T_{max}$ (hr) | $AUC_{inf}$ (ng · hr/mL) |
|---|---|---|---|---|
| 12*/10** | Fasted | 64* (34) | 3.08* (0.79) | 257** (116) |
| 12 | Fed | 106 (37) | 6.42 (1.98) | 398 (123) |

The formulation produced mean (SD) maximum MMF concentrations (Cmax) of 64 (34) ng/mL fasted and 106 (37) ng/mL fed. MMF AUC was 257 (116) ng*h/mL fasted and 398 (123) ng*h/mL fed. The time to peak concentration (Tmax) was 3.08 (0.79) hr fasted and 6.42 (1.98) hr fed. Promoiety was cleared from blood with a half life around 3 hours. (N,N-Diethylcarbamoyl)methyl methyl (2E)but-2-ene-1,4-dioate was well tolerated during the trial. All 12 subjects completed the dosing period. All adverse events were mild. Two subjects in the (N,N-Diethylcarbamoyl)methyl methyl (2E)but-2-ene-1,4-dioate fed group reported flushing more frequently than in the fed placebo group. No subjects in the fasted (N,N-Diethylcarbamoyl)methyl methyl (2E)but-2-ene-1,4-dioate group reported flushing, and no subjects in either the fed or fasted (N,N-Diethylcarbamoyl)methyl methyl (2E)but-2-ene-1,4-dioate groups reported feeling hot more than for placebo. A comparison of these adverse events of the formulation to placebo is shown in Table 13.

TABLE 13

| | Flushing | | Feeling Hot | |
|---|---|---|---|---|
| | Fasted | Fed | Fasted | Fed |
| Placebo | 0 | 1 | 0 | 0 |
| Example 10 Formulation | 2 | 0 | 0 | 0 |

Example 16

This example studied the degradation of an MHF prodrug ((N,N-Diethylcarbamoyl)methyl methyl (2E)but-2-ene-1,4-dioate) in the presence of eighteen potential dosage form polymeric excipients in order to assess their compatibilities. The polymeric excipients were grouped into carboxylic acid-containing (acidic) and carboxylic acid-free (non-acidic) categories, The excipients tested were four sustained release polymers (methyl cellulose (Methocel K4M), carbomer homopolymer type A (Carbopol 971P), ethylcellulose (Ethocel 10) and polyethylene oxide (Polyox WSR-N10)), two granulation binders (hydroxypropyl cellulose (HPC EXF) and polyvinylpyrrolidone (Plasdone K29/32), a diluent (microcrystalline cellulose (Avicel PH102)), two disintegrants (cross-linked sodium carboxymethylcellulose (Crosscarmellose sodium) and cross-linked polyvinylpyrrolidone (Polyplasdone XL-10)), eight polymers for enteric coating and sustained release coating (copolymer of methacrylic acid and methyl methacrylate (Eudragit L100), anionic copolymer of methacrylic acid and ethyl acrylate (Eudragit L100-55), polyvinyl acetate phthalate (PVA-P), cellulose acetate, copolymers of ethyl acrylate, methyl methacrylate and a low content of methacrylic acid ester with quaternary ammonium groups (Eudragit RSPO and Eudragit RLPO, hydroxypropylmethyl cellulose acetate succinate (HPMC-AS) and hydroxypropylmethyl cellulose phthalate (HPMC-P)), and a plasticizer/pore former (Pluronic F68). Approximately 5 mg of (N,N-Diethylcarbamoyl)methyl methyl (2E)but-2-ene-1,4-dioate was weighed into each 4 ml glass vial and mixed with the individual excipient at a ratio of 1:1 or 1:5, as listed in the table below. All acidic polymers were mixed with drug in 1:1 wt/wt ratio, except Carbopol 971P which was mixed in a 5:1 wt ratio.

The acid content of each of the acidic polymers tested is based on the reported acid content of the polymer (reported in US Pharmacopeia), corrected for the portion of the acid content that is the carboxylic acid moiety.

Each sample was stored under open-dish condition with loose caps at 35° C. and 65% relative humidity. This storage condition was selected to expose the samples to elevated temperature and humidity without causing deliquescence of the drug and excipient mixtures. The chemical and physical stability were tested at initial, 1 week, 2 weeks, and 4 weeks.

Figure 15:
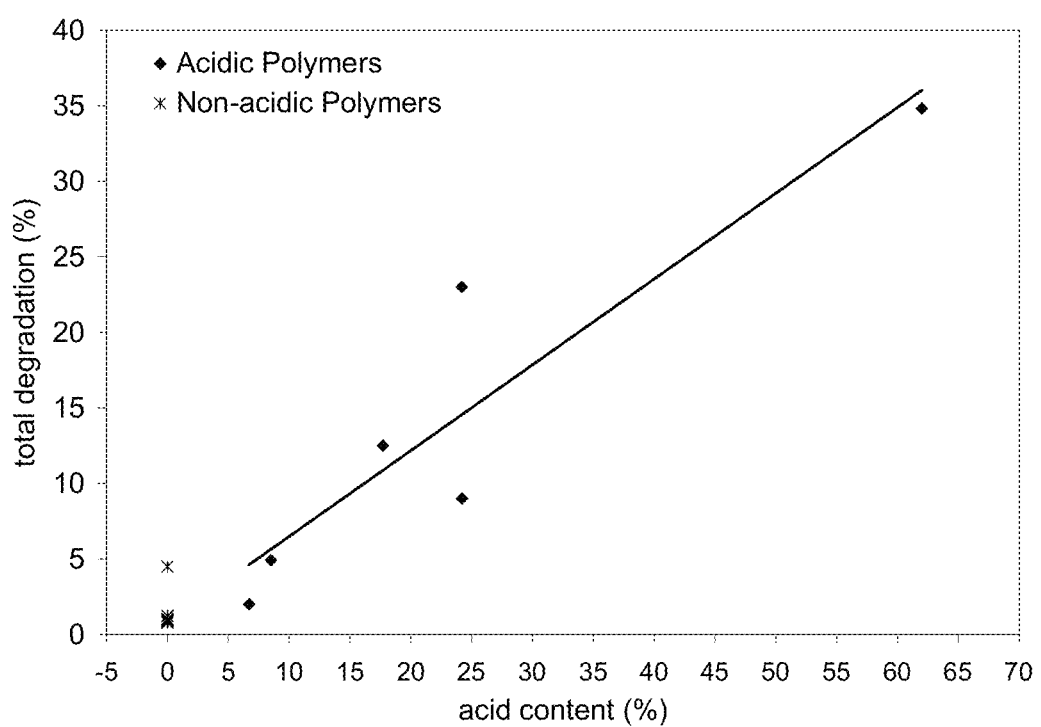
FIG. 15 is a graph showing percent MHF prodrug degradation as a function of enteric polymer carboxylic moiety content, as tested in Example 16.

The percent prodrug degradation data in Table 14 was from the 4-week time point. This data is also plotted in FIG. 15 The percent prodrug degradation was determined as the sum of the fumaric acid, N,N diethyl-2hydroxy acetamide, methyl hydrogen fumarate and (2E)-3-{[(N,N-diethylcarbamoyl)methyl]oxycarbonyl}prop-2-enoic acid contents, expressed as a weight percent of the total initial weight of prodrug.

TABLE 14

| Polymer Type | Polymer Name | Acid Content (%) | Prodrug Degradation (%) |
|---|---|---|---|
| Acidic | Carbopol 971P | 62.0 | 34.8 |
| | Eudragit L100-55 | 24.2 | 23.0 |
| | Eudragit L100 | 24.2 | 9.0 |
| | PVA-P | 17.7 | 12.5 |
| | HPMC-P | 8.5 | 4.9 |
| | HPMC-AS | 6.7 | 2.0 |
| Non-Acidic | Polyox WSR-N10 | 0.0 | 4.5 |
| | Pluronic F68 | 0.0 | 1.2 |
| | Ethocel 10 | 0.0 | 1.2 |
| | Methocel K4M | 0.0 | 1.0 |
| | Eudragit RLPO | 0.0 | 1.0 |

TABLE 14-continued

| Polymer Type | Polymer Name | Acid Content (%) | Prodrug Degradation (%) |
|---|---|---|---|
| | Eudragit RSPO | 0.0 | 1.0 |
| | Crosscarmellose Na | 0.0 | 1.0 |
| | Avicel PH102 | 0.0 | 0.9 |
| | Plasdone K39/32 | 0.0 | 0.9 |
| | Polyplasdone XL10 | 0.0 | 0.9 |
| | HPC EXF | 0.0 | 0.8 |
| | Cellulose acetate | 0.0 | 0.8 |

Example 17

Figure 16:
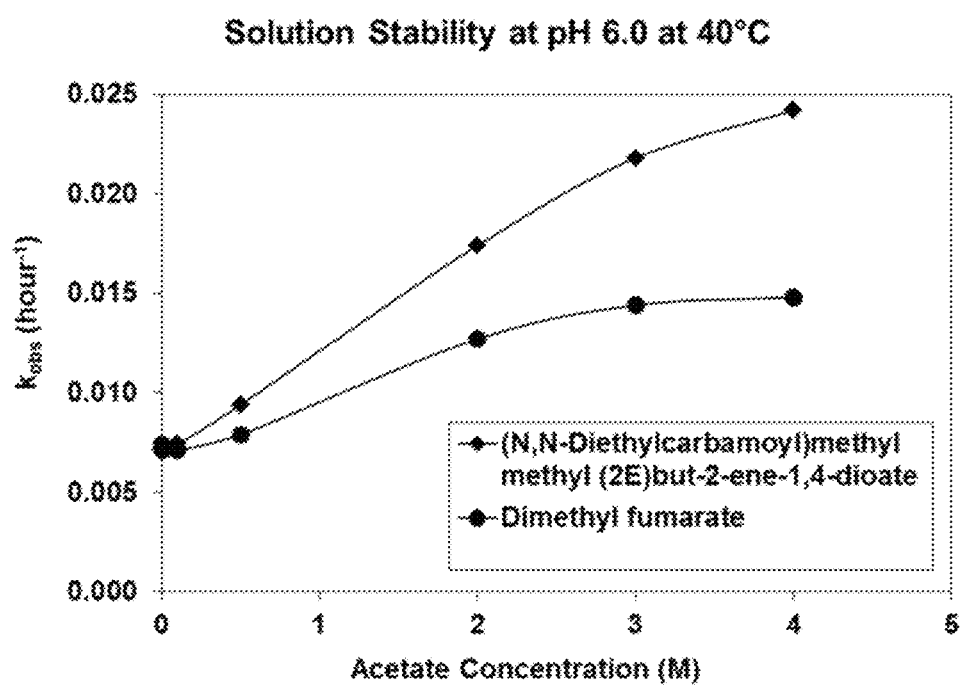
FIG. 16 is a graph showing the rate of degradation of two MHF prodrugs as a function of acetate concentration as tested in Example 17.

This example studied the degradation of two MHF prodrugs, (N,N-Diethylcarbamoyl)methyl methyl (2E)but-2-ene-1,4-dioate and DMF, in the presence of varying quantities of acetic acid. Each prodrug was placed in a pH 6.0 phosphate buffer with multiple concentrations of sodium acetate (0.0 M, 0.1 M, 0.5 M, 2.0 M, 3.0 M, and 4.0 M) at 40° C. The presence of prodrug was measured over time up to 42 hours. The rate of prodrug degradation can be expressed according to the following formula: ln (A)=ln (A$_0$)−K$_{obs}$·t, wherein A is the prodrug concentration, A$_0$ is the prodrug concentration at time zero and K$_{obs}$ is the observed slope of the curve plotting ln (A) versus time (t). Thus, the higher the K$_{obs}$, the more quickly the prodrug is degrading. Thus, K$_{obs}$ is a measure of prodrug stability, with prodrugs having a lower K$_{obs}$ being more stable than prodrugs having a higher K$_{obs}$. The K$_{obs}$ for (N,N-Diethylcarbamoyl)methyl methyl (2E)but-2-ene-1,4-dioate and DMF are plotted as a function of acetate concentration in FIG. 16.

Figure 17:
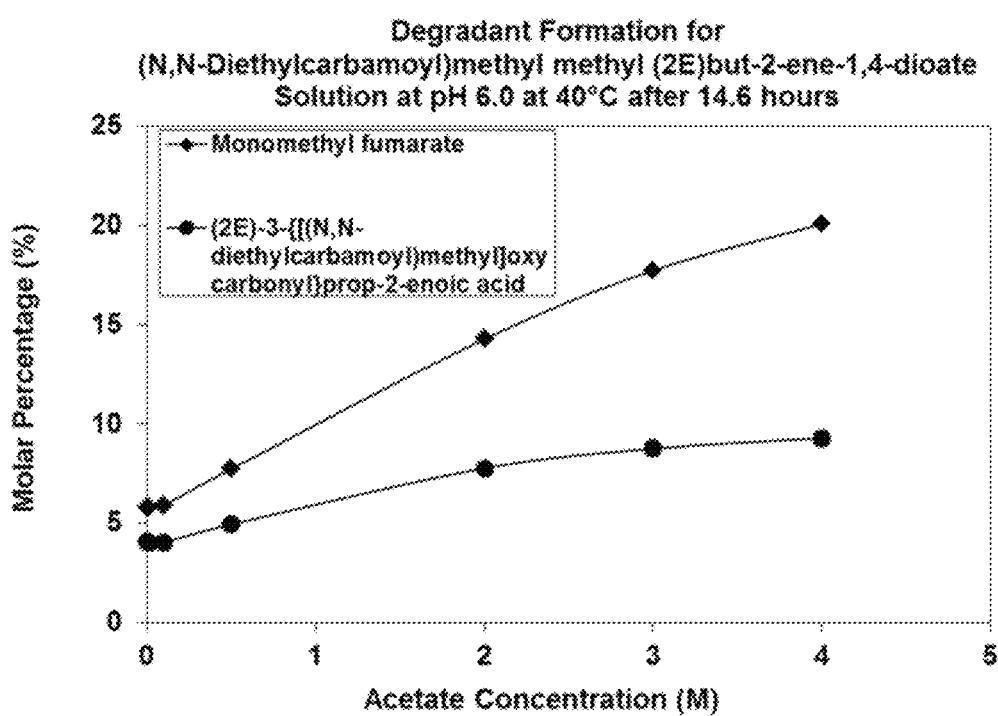
FIG. 17 is a graph showing the amounts of MHF and another primary degradant formed upon degradation of an MHF prodrug as a function of acetate concentration, as tested in Example 17.

The amounts of the two primary degradation products for prodrug (N,N-Diethylcarbamoyl)methyl methyl (2E)but-2-ene-1,4-dioate were measured after a 14.6 hour exposure to acetate solutions of varying concentrations, all at pH 6.0 and 40° C. The data are shown in FIG. 17. Thus, FIG. 17 depicts the amount of each of the two primary degradation products of (N,N-Diethylcarbamoyl)methyl methyl (2E)but-2-ene-1,4-dioate as a mole % of the initial amount of prodrug, at the varying acetate concentrations.

The degradation rates of both MHF prodrugs increased with increasing concentrations of acetate. Without wishing to be limited to a specific mechanism or mode of action, increased carboxyl concentration independent of pH causes increased degradation of the MHF prodrugs. It is believed that selection of pharmaceutical excipient and barrier layer components that are substantially free of carboxylic acid moieties reduces the degradation of the MHF prodrugs.

Finally, it should be noted that there are alternative ways of implementing the subject matter of the present disclosure. Accordingly, the present embodiments are to be considered as illustrative and not restrictive, and the present disclosure is not to be limited to the details given herein, but may be modified within the scope and equivalents of the claim(s) issuing here from.

The invention claimed is:

1. An oral dosage form comprising:
a core comprising a therapeutically effective amount of (N,N-Diethylcarbamoyl)methyl methyl(2E)but-2-ene-1,4-dioate;
a barrier layer directly coating said core, the barrier layer comprising a non-ionizable polymer; the barrier layer preventing direct contact between the core and an enteric coating; and
the enteric coating directly surrounding said barrier layer and comprising an enteric polymer having carboxylic acid moieties, the enteric polymer (i) being soluble in aqueous solutions having a pH above 7.5 and (ii) starting to become soluble in an aqueous solution at a pH in the range of 4.5 to 7.5.

2. The oral dosage form of claim 1, wherein the barrier layer material is selected from non-ionizable cellulosic polymers, non-ionizable vinyl polymers, and non-ionizable polyvinyl alcohol polymers.

3. The oral dosage form of claim 1, wherein the barrier layer material is a sugar.

4. The oral dosage form of claim 1, wherein the barrier layer comprises at least 5 wt % of the coated core for cores having a size of 2 mm or less.

5. The oral dosage form of claim 1, wherein the barrier layer comprises at least 0.5 wt % of the coated core for cores having a size greater than 6 mm.

6. The oral dosage form of claim 1, wherein the barrier layer has an average thickness of at least 5 μm.

7. The oral dosage form of claim 1, wherein the barrier layer has an average thickness of at least 15 μm.

8. The oral dosage form of claim 1, wherein the core is a compressed tablet and the barrier layer and enteric coating are each a coating on the tablet.

9. The oral dosage form of claim 8, wherein the tablet contains from 100 to 1200 mg of (N,N-Diethylcarbamoyl)methyl methyl(2E)but-2-ene-1,4-dioate and one or more tableting excipients.

10. The oral dosage form of claim 9, wherein the tableting excipients are selected from binders, diluents, disintegrants, glidiants and lubricants.

11. The oral dosage form of claim 1, wherein the dosage form is a capsule containing a multiplicity of said enteric coated cores.

12. The oral dosage form of claim 1, wherein the core comprises an immediate release dosage form.

13. The oral dosage form of claim 1, wherein the core comprises a sustained release dosage form.

14. The oral dosage form of claim 1, wherein the enteric polymer is selected from methyacrylic acid polymers, cellulose acetate phthalate polymers, hydroxypropylmethyl cellulose acetate succinate polymers, hydroxypropylmethyl cellulose phthalate polymers and polyvinyl acetate phthalate polymers.

15. A method of treating a disease selected from the group consisting of multiple sclerosis and psoriasis in a patient, comprising orally administering to a patient in need thereof a dosage form of claim 1.

16. The method of claim 15, wherein the oral administration is sufficient to obtain a therapeutic concentration of methyl hydrogen fumarate in blood plasma of the patient of at least 0.7 μg/ml at a time within 24 hours after said oral administration.

17. The method of any one of claim 15, wherein the oral administration is sufficient to obtain an area under a concentration of methyl hydrogen fumarate in the blood plasma versus time curve (AUC) of at least 12.0 μg·hr/ml over 24 hours after start of the oral administration.

18. The oral dosage form of claim 14, wherein the enteric coating is selected form the group consisting of hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxymethyl cellulose, carboxymethyl cellulose, cellulose acetate phthalate, methyl cellulose acetate phthalate, ethyl cellulose acetate phthalate, hydroxypropyl cellulose acetate phthalate, hydroxypropyl methyl cellulose acetate succinate phthalate, hydroxypropyl cellulose succinate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

\* \* \* \* \*